United States Patent
Pojasek et al.

(10) Patent No.: US 7,129,335 B2
(45) Date of Patent: Oct. 31, 2006

(54) METHODS FOR PURIFYING AND ISOLATING RECOMBINANT CHONDROITINASES

(75) Inventors: Kevin Pojasek, Boston, MA (US); Rahul Raman, Cambridge, MA (US); Ram Sasisekharan, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/966,671

(22) Filed: Oct. 14, 2004

(65) Prior Publication Data

US 2005/0227320 A1 Oct. 13, 2005

Related U.S. Application Data

(62) Division of application No. 10/454,816, filed on Jun. 3, 2003, now Pat. No. 6,962,699.

(60) Provisional application No. 60/385,509, filed on Jun. 3, 2002.

(51) Int. Cl.
*A23J 1/00* (2006.01)
*C12N 9/88* (2006.01)
*C07H 21/04* (2006.01)

(52) U.S. Cl. ............... 530/412; 435/232; 536/23.2

(58) Field of Classification Search ............ 530/412; 435/232; 536/23.2
See application file for complete search history.

(56) References Cited

U.S. PATENT DOCUMENTS

| | | | |
|---|---|---|---|
| 4,341,869 A | 7/1982 | Langer et al. | |
| 5,145,778 A | 9/1992 | Bellamy et al. | |
| 5,169,772 A | 12/1992 | Zimmerman et al. | |
| 5,198,355 A | 3/1993 | Kikuchi et al. | |
| 5,198,855 A | 3/1993 | Iwai | |
| 5,290,695 A | 3/1994 | Morikawa et al. | |
| 5,338,677 A | 8/1994 | Zimmerman et al. | |
| 5,389,539 A | 2/1995 | Sasisekharan et al. | |
| 5,496,718 A | 3/1996 | Hashimoto et al. | |
| 5,498,536 A | 3/1996 | Khandke | |
| 5,525,500 A | 6/1996 | Khandke et al. | |
| 5,567,417 A | 10/1996 | Sasisekharan et al. | |
| 5,569,600 A | 10/1996 | Sasisekharan et al. | |
| 5,578,480 A | 11/1996 | Khandke | |
| 5,619,421 A | 4/1997 | Venkataraman et al. | |
| 5,668,274 A | 9/1997 | Petitou et al. | |
| 5,681,733 A | 10/1997 | Su et al. | |
| 5,714,376 A | 2/1998 | Sasisekharan et al. | |
| 5,716,617 A | 2/1998 | Khandke et al. | |
| 5,741,692 A * | 4/1998 | Khandke et al. ............ | 435/200 |
| 5,763,205 A | 6/1998 | Hashimoto et al. | |
| 5,773,277 A | 6/1998 | Hashimoto et al. | |
| 5,801,162 A | 9/1998 | Takada et al. | |
| 5,817,645 A | 10/1998 | Zamboni et al. | |
| 5,830,726 A | 11/1998 | Sasisekharan et al. | |
| 5,866,120 A | 2/1999 | Karageozian et al. | |
| 5,919,693 A | 7/1999 | Su et al. | |
| 5,965,507 A | 10/1999 | Thoen et al. | |
| 5,968,822 A | 10/1999 | Pecker et al. | |
| 5,997,863 A | 12/1999 | Zimmermann et al. | |
| 6,001,630 A | 12/1999 | Ichikawa | |
| 6,007,810 A | 12/1999 | Ishikawa et al. | |
| 6,039,943 A | 3/2000 | Karageozian et al. | |
| 6,054,569 A | 4/2000 | Bennett et al. | |
| 6,063,378 A | 5/2000 | Nohara et al. | |
| 6,093,563 A * | 7/2000 | Bennett et al. ............. | 435/232 |
| 6,184,023 B1 | 2/2001 | Hashimoto et al. | |
| 6,190,875 B1 | 2/2001 | Ben-Artzi et al. | |
| 6,217,863 B1 | 4/2001 | Godavarti et al. | |
| 6,378,527 B1 | 4/2002 | Hungerford et al. | |
| 6,597,996 B1 | 7/2003 | Venkatamaran et al. | |
| 6,869,789 B1 | 3/2005 | Liu et al. | |
| 6,962,699 B1 | 11/2005 | Pojasek et al. | |
| 2002/0122793 A1 | 9/2002 | Liu et al. | |
| 2002/0128225 A1 | 9/2002 | Liu et al. | |
| 2002/0169143 A1 | 11/2002 | Sasisekharan et al. | |
| 2003/0008820 A1 | 1/2003 | Kwan et al. | |
| 2003/0096281 A1 | 5/2003 | Venkataraman et al. | |
| 2003/0099628 A1 | 5/2003 | Liu et al. | |
| 2003/0191587 A1 | 10/2003 | Venkataraman et al. | |
| 2003/0203385 A1 | 10/2003 | Venkataraman et al. | |
| 2003/0219830 A1 | 11/2003 | Venkataraman et al. | |
| 2004/0087543 A1 | 5/2004 | Shriver et al. | |
| 2004/0091471 A1 | 5/2004 | Myette et al. | |
| 2004/0091472 A1 | 5/2004 | Pojasek et al. | |

(Continued)

FOREIGN PATENT DOCUMENTS

EP 0355831 A2 2/1990

(Continued)

OTHER PUBLICATIONS

Achur et al., "Characterization of Proteoglycans of Human Placenta and Identification of Unique Chondroitin Sulfate Proteoglycans of the Intervillous Spaces that Mediate the Adherence of *Plasmodium falciparum*-infected Erythrocytes to the Placenta," *The Journal of Biological Chemistry*, vol. 275(51), Dec. 22, 2000, pp. 40344-40356.

(Continued)

*Primary Examiner*—Tekchand Saidha
(74) *Attorney, Agent, or Firm*—Wolf, Greenfield & Sacks, P.C.

(57) ABSTRACT

The invention relates to rationally designed polysaccharide lyases and uses thereof. In particular, the invention relates to modified chondroitinase B. The modified chondroitinase B enzymes of the invention are useful for a variety of purposes, including cleaving and sequencing polysaccharides such as glycosaminoglycans (GAGs) as well as removing polysaccharides from a solution. The invention also includes methods of inhibiting anticoagulant activity, inhibiting angiogenesis, treating cancer, and inhibiting maternal malarial infection.

8 Claims, 11 Drawing Sheets

U.S. PATENT DOCUMENTS

| | | |
|---|---|---|
| 2004/0092037 A1 | 5/2004 | Sasisekharan et al. |
| 2004/0147033 A1 | 7/2004 | Shriver et al. |
| 2004/0197933 A1 | 10/2004 | Venkataraman et al. |
| 2004/0204869 A1 | 10/2004 | Venkataraman et al. |
| 2004/0214228 A9 | 10/2004 | Venkataraman et al. |
| 2005/0037376 A1 | 2/2005 | Sasisekharan et al. |
| 2005/0065738 A1 | 3/2005 | Raguram |
| 2005/0214276 A9 | 9/2005 | Myette et al. |
| 2005/0227320 A1 | 10/2005 | Pojasek et al. |
| 2005/0233401 A1 | 10/2005 | Liu et al. |
| 2005/0233402 A1 | 10/2005 | Liu et al. |
| 2005/0233419 A1 | 10/2005 | Pojasek et al. |
| 2005/0266067 A1 | 12/2005 | Sengupta et al. |
| 2006/0024664 A1 | 2/2006 | Sasisekharan et al. |

FOREIGN PATENT DOCUMENTS

| | | |
|---|---|---|
| EP | 0 613 949 B1 | 9/1994 |
| EP | 1 607 478 A2 | 12/2005 |
| JP | 54107586 A | 8/1979 |
| JP | 2000044601 A | 2/2000 |
| WO | WO 91/16070 A1 | 10/1991 |
| WO | WO 93/08289 | 4/1993 |
| WO | WO 94/12618 | 6/1994 |
| WO | WO 95/13830 | 5/1995 |
| WO | WO 95/34635 | 12/1995 |
| WO | WO 96/01648 A1 | 1/1996 |
| WO | WO 96/01894 A1 | 1/1996 |
| WO | WO 97/16556 A1 | 5/1997 |
| WO | WO 97/18835 A1 | 5/1997 |
| WO | WO 99/58650 A1 | 11/1999 |
| WO | WO 200139795 A2 | 2/2000 |
| WO | WO 01/34781 A2 | 5/2001 |
| WO | WO 01/35977 A2 | 5/2001 |
| WO | WO 01/38399 A1 | 5/2001 |
| WO | WO 01/53474 A2 | 7/2001 |
| WO | WO 03/074080 A1 | 9/2003 |
| WO | WO 2004/110360 A2 | 12/2004 |
| WO | WO 2005/112986 | 12/2005 |

OTHER PUBLICATIONS

Alkhalil et al., "Structural Requirements for the Adherence of *Plasmodium falciparum*-infected Erythrocytes to Chondroitin Sulfate Proteoglycans of Human Placenta," *The Journal of Biological Chemistry*, vol. 275(51), Dec. 22, 2000, pp. 40357-40364.

Baker, J. R. et al., "Action Pattern and Substrate Specificity of the Hyaluronan Lyase from Group B Streptococci", *Biochem. J.*, vol. 348, 2000, pp. 465-471.

Catlow et al., "Hepatocyte Growth Factor/scatter Factor and its Interaction With Heparan Sulphate and Dermatan Sulphate", *Biochemical Society Transactions*, 2003, vol. 31(Part 2), pp. 352-353.

Daidouji et al., "Neoplastic Changes in Saccharide Sequence of Dermatan Sulfate Chains Derived from Human Colon Cancer," *Digestive Diseases and Sciences*, vol. 47(2) Feb. 2002, pp. 331-337.

Denholm et al., "Anti-Tumor Activities of Chondroitinase AC and Chondroitinase B: Inhibition of Angiogenesis, Proliferation and Invasion," *European Journal of Pharmacology*, vol. 416, 2001, pp. 213-221.

Denholm et al., "Inhibition of Human Dermal Fibroblast Proliferation by Removal of Dermatan Sulfate," *European Journal of Pharmacology*, vol. 400, 2000, pp. 145-153.

Dierks et al., "Posttranslational Formation of Formylglycine in Prokaryotic Sulfatases by Modification of Either Cysteine or Serine", *The Journal of Biological Chemistry*, vol. 273(40), Oct. 2, 1998, pp. 25560-25564.

Ernst, S. et al., "Enzymatic Degradation of Glycosaminoglycans" *Critical Reviews in Biochemistry and Molecular Biology*, vol. 30(5), 1995, pp. 387-444.

Ernst, S. et al., "Direct Evidence for a Predominantly Exolytic Processive Mechanism for Depolymerization of Heparin-like Glycosaminoglycans by Heparinase I", *Proceedings of the National Academy of Sciences of the United States of America*, vol. 95, Apr. 1998, pp. 4182-4187.

Gacesa et al., "Enzymic Degradation of Alginates", *International Journal of Biochemistry*, vol. 24(4), 1992, pp. 545-552.

Gandra et al., "Anticoagulant Sulfated Glycosaminoglycans in the Tissues of the Primitive Chordate *Styela plicata* (Tunicata)", *Glycobiology*, vol. 10(12), 2000, pp. 1333-1340.

Gerit et al., "Understanding the Rates of Certain Enzyme-Catalyzed Reactions: Proton Abstraction from Carbon Acids, Acyl-Transfer Reactions and Displacement Reactions of Phosphodiesters", *Biochemistry*, vol. 32(45), Nov. 16, 2003, pp. 11943-11952.

Gu, K. et al., "Purification, Characterization and Specificity of Chondroitin Lyases and Glycuronidase from *Flavobacterium heparinum*" *Biochemistry Journal*, vol. 312, 1995, pp. 569-577.

Habuchi, O., "Diversity and Functions of Glycosaminoglycan Sulfotransferases", *Biochimica Et Biophysica Acta*, vol. 1474, 2000, pp. 115-127.

Homans, S. W., "A Molecular Mechanical Force Field for the Conformational Analysis of Oligosaccharides: Comparison of Theoretical and Crystal Structures of Manα1-3Manβ1-4GlcNAc", *Biochemistry*, vol. 29, 1990, pp. 9110-9118.

Huang et al., "Crystal Structure of Chondroitinase B from *Flavobacterium heparinum* and Its Complex with a Disaccharide Product at 1.7 Å Resolution," *The Journal of Molecular Biology*, vol. 294, 1999, pp. 1257-1269.

Huang, W. et al., "Active Site of Chondroitin AC Lyase Revealed by the Structure of Enzyme-Oligosaccharide Complexes and Mutagenesis", *Biochemistry*, vol. 40, 2001, pp. 2359-2372.

Huige, C. J. M. et al., "Force Field Parameters for Sulfates and Sulfamates Based on *Ab Initio* Calculations: Extensions of AMBER and CHARMm Fields", *Journal of Computational Chemistry*, vol. 16(1), 1995, pp. 56-79.

Jandik, K. A., et al., "Action Pattern of Polysaccharide Lyases on Glycosaminoglycans", *Glycobiology*, vol. 4(3), 1994, pp. 289-296.

Jenkins et al., "The Architecture of Parallel β-Helices and Related Folds", *Progress in Biophysics & Molecular Biology*, vol. 77, 2001, pp. 111-175.

Karamanos et al., "Identify of Dermatan and Chondroitin Sequences in Dermatan Sulfate Chains Determined by Using Fragmentation with Chondroitinases and Ion-Pair High-Performance Liquid Chromatography," *Analytical Biochemistry*, vol. 225, 1995, pp. 220-230.

Lin, B. et al., "Identification of a Histidine Residue Essential for Enzymatic Activity of Group B Streptococcal Hyaluronate Lyase", *Biochemical and Biophysical Research Communications*, vol. 231, 1997, pp. 379-382.

Liu, D. et al., "Tumor Cell Surface Heparan Sulfates as Cryptic Promoters or Inhibitors or Tumor Growth and Metastasis", *Proceedings of the National Academy of Sciences of the United States of America*, vol. 99(2), Jan. 22, 2002, pp. 568-573.

Lyon et al., "Hepatocyte Growth Factor/Scatter Factor Binds with High Affinity to Dermatan Sulfate," *The Journal of Biological Chemistry*, vol. 273(1), Jan. 2, 1998, pp. 271-278.

Lyon et al., "The Mode of Action of Heparan and Dermatan Sulfates in the Regulation of Hepatocyte Growth Factor/Scatter Factor," *The Journal of Biological Chemistry*, vol. 277(2), Jan. 11, 2002, pp. 1040-1046.

Maimone, M. M. et al., "Structure of a Dermatan Sulfate Hexasaccharide that Binds to Heparin Cofactor II with High Affinity", *The Journal of Biological Chemistry*, vol. 265, 1990, p. 14830.

Mascellani, G. et al., "Structure and Contribution to the Heparin Cofactor II-mediated Inhibition of Thrombin of Naturally Oversulphated Sequences of Dermatan Sulphate", *Biochemical Journal*, vol. 296, 1993, pp. 639-648.

Michel et al., "The Structure of Chondroitin B Lyase Complexed with Glycosaminoglycan Oligosaccharides Unravels a Calcium-dependent Catalytic Machinery", *The Journal of Biological Chemistry*, vol. 279(31), Jul. 30, 2004, pp. 32882-32896.

Mitropoulou et al., "Identification of Oligomeric Domains within Dermatan Sulfate Chains Using Differential Enzymic Treatments, Derivatization with 2-Aminoacridone and Capillary Electrophoresis," *Electrophoresis*, vol. 22, 2001, pp. 2458-2463.

Monagle et al., "Covalent Heparin Cofactor II-Heparin and Heparin Cofactor II-Dermatan Sulfate Complexes," *The Journal of Biological Chemistry*, vol. 273(50), Dec. 11, 1998, pp. 33566-33571.

Nadanaka, S. et al., "The Unusual Tetrasaccharide Sequence GlcAβ1-3GalNAc(4-sulfate)β1-4GlcA(2-sulfate)β1-3GalNAc(6-sulfate) found in the Hexasaccharides Prepared by Testicular Hyaluronidase Digestion of Shark Cartilage Chondroitin Sulfate D" *Glycobiology*, vol. 7(2), 1997, pp. 253-263.

Pagès, S. et al., Changing a Single Amino Acid Residue Switches Processive and Non-processive Behavior of *Aspergillus niger* Endopolygalacturonase I and II, *The Journal of Biological Chemistry*, vol. 276(36), Sep. 7, 2001, pp. 33652-33656.

Pervin et al., "Capillary Electrophoresis to Measure Sulfoesterase Activity on Chondroitin Sulfate and Heparin Derived Disaccharides", *Applied and Theoretical Electrophoresis*, vol. 3, 2003, pp. 297-303.

Plaas et al., "Glycosaminoglycan Sulfation in Human Osteoarthritis," *The Journal of Biological Chemistry*, vol. 273(20), May 15, 1998, pp. 12642-12649.

Pojasek et al., Recombinant Expression, Purification, and Kinetic Characterization of Chondroitinase AC and Chondroitinase B from *Flavobacterium heparinum*, *Biochemical and Biophysical Research Communications*, vol. 286, 2001, pp. 343-351.

Pojasek K. et al., "Biochemical Characterization of the Chondroitinase B Active Site", *The Journal of Biological Chemistry*, vol. 277(34), Aug. 23, 2002, pp. 31179-31186.

Pojasek et al., Histidine 295 and Histidine 510 Are Crucial for the Enzymatic Degradation of Heparan Sulfate by Heparinase III, *Biochemistry*, vol. 39, 2000. pp. 4012-4019.

Rhomberg, A. J. et al., "Mass Spectrometric and Capillary Electrophoretic Investigation of the Enzymatic Degradation of Heparin-like Glycosaminoglycans", *Proceedings of the National Academy of Sciences of the United States of America*, vol. 95, Apr. 1998, pp. 4176-4181.

Rhomberg, A. J. et al., "Mass Spectrometric Evidence for the Enzymatic Mechanisms of the Depolymerization of Heparin-like Glycosaminoglycans by Heparinase II", *Proceedings of the National Academy of Sciences of the United States of America*, vol. 95, Oct. 1998, pp. 12232-12237.

Roy, C. et al., "Modes of Action of Five Different Endopectate Lyases from *Erwinia chrysantehmi* 3937" *Journal of Bacteriology*, vol. 181(12), Jun. 1999, pp. 3705-3709.

Sasisekharan, R. et al., "Cloning and Expression of Heparinase I Gene from *Flavobacterium heparinum*" *Proceedings of the National Academy of Sciences of the United States of America*, vol. 90, Apr. 1993, pp. 3660-3664.

Sasisekharan, R. et al., "Heparinase I from *Flavobacterium heparinum*" *The Journal of Biological Chemistry*, vol. 271(6), Feb. 9, 1996, pp. 3124-3131.

Scavetta, R. D. et al., "Structure of a Plant Cell Wall Fragment Complexed to Pectate Lyase C", *The Plant Cell*, vol. 11, Jun. 1999, pp. 1081-1092.

Shriver et al., "Sequencing of 3-O Sulfate Containing heparin Decasaccharides with a Partial Antithrombin III Binding Site", *Proceedings of the National Academy of Sciences of the United States of America*, vol. 97(19), Sep. 12, 2000, pp. 10359-10364.

Shriver et al., "Cleavage of the Antithrombin III Binding Site in Heparin by Heparinases and its Implication in the Generation of Low Molecular Weight Heparin", *Proceedings of the National Academy of Sciences of the United States of America*, vol. 97(19), Sep. 12, 2000, pp. 10365-10370.

Shriver, Z. et al., "Heparinase II from *Flavobacterium heparinum*: . . . ", *The Journal of Biological Chemistry*, vol. 273(17), Apr. 24, 1998, pp. 10160-10167.

Shriver, Z. et al., "Heparinase II from *Flavobacterium heparium*: . . . ", *The Journal of Biological Chemistry*, vol. 273(36), Sep. 4, 1998, pp. 22904-22912.

Shriver, Z. et al., "Emerging Views of Heparan Sulfate Glycosaminoglycan Structure/Activity Relationships Modulating Dynamic Biological Functions" *Trends Cardiovascular Med.*, vol. 12(2), 2002, pp. 71-77.

Steinbacher, S. et al.,"Crystal Structure of P22 Tailspike Protein: Interdigitated Subunits in a Thermostable Trimer", *Science*, vol. 265(5170), Jul. 15, 1994, pp. 383-386.

Sugahara, K. et al., "Novel Sulfated Oligosaccharides Containing 3-*O*-Sulfated Glucuronic Acid from King Crab Cartilage Chondroitin Sulfate K . . . ", *The Journal of Biological Chemistry*, vol. 271(43), Oct. 25, 1996, pp. 26745-26754.

Sundaram et al., "Rational Design of Low-Molecular Weight Heparins with Improved *In Vivo* Activity", *Proceedings of the National Academy of Sciences of the United States of America*, vol. 100(2), Jan. 21, 2003, pp. 651-656.

Trowbridge et al., "Dermatan Sulfate Binds and Potentiates Activity of Keratinocyte Growth Factor (FGF-7)," *The Journal of Biological Chemistry*, vol. 277(45), Nov. 8, 2002, pp. 42815-42820.

Trowbridge et al., "Dermatan Sulfate: New Functions from an Old Glycosaminoglycan," *Glycobiology*, vol. 12(9), 2002, pp. 117R-125R.

Tumova, S. et al., "Heparan Sulfate Proteoglycans on the Cell Surface: Versatile Coordinators of Cellular Functions", *The International Journal of Biochemistry & Cell Biology*, vol. 32, 2000, pp. 269-288.

Ueoka, C. et al., "Structural Determination of Novel Tetra- and Hexasaccharide Sequences Isolated from Chondroitin Sulfate H (Oversulfated Dermatan Sulfate) of Hagfish Notochord", *Glycoconjugate Journal*, vol. 16, 1999, pp. 291-305.

van den Hoogen, B. M. et al., "A Microtiter Plate Assay for the Determination of Uronic Acids", *Analytical Biochemistry*, vol. 257, 1998, pp. 107-111.

Venkataraman, G. et al., "A Stereochemical Approach to Pyranose Ring Flexibility: Its Implications for the Conformation of Dermatan Sulfate", *Proceedings of the National Academy of Sciences of the United States of America*, vol. 91, Jun. 1994, pp. 6171-6175.

Venkataraman, G. et al., "Sequencing Complex Polysaccharides", *Science*, vol. 286, Oct. 15, 1999, pp. 537-542.

Vicente, C.P. et al., "Unbalanced Effects of Dermatan Sulfates with Different Sulfation Patterns on Coagulation, Thrombosis and Bleeding", *Thromb. Haemost.*, vol. 86, 2001, pp. 1215-1220.

Yang, H.O. et al., "Preparation and Structural Determination of a Dermatan Sulfate-Derived Oligosaccharides", *Glycobiology*, vol. 10(10), 2000, pp. 1033-1039.

Yoder et al., "The Refined Three-Dimensional Structure of Pectate Lyase C . . . ," *Plant Physiol.*, vol. 107, 1995, pp. 349-364.

NCBI database, Protein IDBGA *Chain A. Crystal Structure of Chondroitinase B*, Accession No. 6980641.

NCBI database, Protein IDBOA *Chain A. Crystal Structure of Chondroitinase B*, Accession No. 6980642.

NCBI database, "Pedobacter Heparinus Chondroitinase B Precursor (cs1B) gene Complete cds", Accession No. U27584.1 GI:1002526.

NCBI database, Structure Summary IDBO, *Crystal Structure of Chondroitinase B*, MMDB No. 12452.

Protein Data Bank, Structure Explorer—1DBO, "Crystal Structure of Chondroitinase B" http://www.rcsb.org/pdb/cgi/explore.cgi/ex:ore.cgi?pdbld=1DBO, printed Feb. 23, 2005, 1 page.

Structure Summary Printout for 1dbo, http://pdbbeta.rcsb.org/pdb/explore.do?structureld=ldbo, printed Feb. 23, 2005, 1 page.

NCBI database, Structure Summary for 1DBG, *Crystal Structure of Chondroitinase B*, MMDB No. 12451.

Structure Summary Printout for Idbg, http://pdbbeta.rcsb.org/pdb/explore.do?structureld=ldbg, printed Feb. 23, 2005, 1 page.

Protein Data Bank, Structure Explorer—1DBG, "Crystal Structure of Chondroitinase B", http://www.rcsb.org/pdb/cgi/explore.cgi?pdbId=lDBG, printed Feb. 23, 2005, 1 page.

NCBI Database, Structure Summary for 1HM2, *Crystal Structure of Chondroitinase B*, MMDB No. 16157.

Protein Data Bank, Structure Explorer—1HM2, "Active Site of Chondroitinase Ac Lyase Revealed by The Structure of Enzyme-Oligosaccharide Complexes and Mutagenesis", http://www/rcsb.org/pdb/cgi/explore.cgi?pdbId=1HM2, printed Feb. 23, 2005, 1 page.

Structure Summary Printout for 1HM2, http://pdbbeta.rcsb.org/pdb/explore.do?structureId=1hm2, printed Feb. 23, 2005, 2 pages.

NCBI Database, Structure Summary for 1PLU, "*Pectate Lyase from Erwinia Chrysanthemi* . . . ", MMDB No. 10896.

Protein Data Bank, Structure Explorer—1PLU, "Pectate Lyase C From Erwinia Chrysanthemi With 1 Lu+3 Ion in the Putative Calcium Binding Site", http://rcsb.org/pdb/cgi/explore.cgi?pdbId=1PLU, printed Feb. 23, 2005, p. 1.

Structure Summary Printout for 1plu, "Pectate Lyase C From Erwinia Chrysanthemi With 1 Lu+3 Ion in the Putative Calcium Binding Site", http://pdbbeta.rcsb.org/pdb/explore.do?structureId=1plu, printed Feb. 23, 2005, 1 page.

Tkalec, A.L. et al., "Isolation and Expression in *Escherichia coli* of *cslA* and *cslB*, Genes Coding for the Chondroitin Sulfate-Degrading Enzymes Chondroitinase AC and Chondroitinase B, Respectively from *Flavobacterium heparium*", Applied and Environmental Microbiology, 2000, pp. 29-35.

Theocharis D.A., et al., "Determination and structural Characterisation of Dermatan Sulfate in the Presence of Other Galactosaminoglycans", *Journal of Chromatography B*, vol. 754(2), Apr. 25, 2001, pp. 297-309.—Abstract Only.

Yunge et al., "Crystallization and Preliminary X-ray Analysis of Chondroitinase B from *Flavobacterium heparium*", *Acta Crystallographica Section D Biological Crystallography*, vol. 55(5), May 1999, pp. 1055-1057.—Abstract Only.

Aguiar et al., Preparation and purification of *Flavobacterium heparium* chondroitinase AC and B by hydrophobic interaction chromatography. Braz J Med Biol Res. May 1999;32(5):545-50. Abstract Only.

Bernstein et al., Immobilized heparin lyase system for blood deheparinization. Methods in Enzymol. 1988;46:515-29.

Conrad et al., Structure of heparan sulfate and dermatan sulfate. Ann N Y Acad Sci. 1989;556:18-28.

Desai et al., Specificity studies on the heparin lyases from *Flavobacterium heparium*. Biochemistry. Aug. 17, 1993;32(32):8140-5.

Dietrich et al., Enzymatic degradation of heparin. A glucosaminidase and a glycuronidase from *Flavobacterium heparium*. Biochemistry. May 1969;8(5):2089-94.

Dietrich et al., Sequential degradation of heparin in *Flavobacterium heparium*. Purification and properties of five enzymes involved in heparin degradation. J Biol Chem. Sep. 25, 1973;248(18):6408-15.

Ernst et al., Expression in *Escherichia coli*, purification and characterization of heparinase I from *Flavobacterium heparinum*. Biochem J. Apr. 15, 1996;315 (Pt 2):589-97.

Gacesa et al., Alginate-modifying enzymes: A proposed unified mechanism of action for the lyases and epimerase. FEBS. Feb. 1987;212(2):199-202.

Gioldassi et al., Determination of phosphorylated and sulfated linkage-region oligosaccharides in chondroitin / dematan and heparan sulfate proteoglycans by high performance liquid chromatography. J Liq Chrom Rel Technol. 1999;22(13):1997-2007.

Godavarti et al., Heparinase I from *Flavobacterium heparium*. Identification of a critical histidine residue essential for catalysis as probed by chemical modification and site-directed mutagenesis. Biochemistry. May 28, 1996;35(21):6846-52.

Godavarti et al., Heparinase I from *Flavobacterium heparium*. Role of positive charge in enzymatic activity. J Biol Chem. Jan. 2, 1998;273(1):248-55.

Godavarti et al., Heparinase III from *Flavobacterium heparium*: cloning and recombinant expression in *Escherichia coli*. Biochem Biophys Res Commun. Aug. 23, 1996;225(3):751-8.

Godavarti et al., A comparative analysis of the primary sequences and characteristics of heparinases I, II, and III from *Flavobacterium heparinum*. Biochem Biophys Res Commun. Dec. 24, 1996;229(3):770-7.

Hashimoto et al., Unsaturated glucuronyl hydrolase of *Bacillus sp.* GL1: novel enzyme prerequisite for metabolism of unsaturated oligosaccharides produced by polysaccharide lyases. Arch Biochem Biophys. Aug. 15, 1999;368(2)367-74.

Hovingh et al., Specificity of flavobacterial glycuronidases acting on disaccharides derived from glycosaminoglycans. Biochem J. Aug. 1, 1977;165(2):287-93.

Hulett et al., Cloning of mammalian heparanase, an important enzyme in tumor invasion and metastasis. Nat Med. Jul. 1999;5(7):803-9.

Kjellen et al., Proteoglycans: structures and interactions. Annu Rev Biochem. 1991;60:443-75.

Liu et al., Strategy for the sequence analysis of heparin. Glycobiology. Dec. 1995;5(8):765-74.

Liu et al., The calcium-binding sites of heparinase I from *Flavobacterium heparium* are essential for enzymatic activity. J Biol Chem. Feb. 12, 1999;274(7):4089-95.

Liu et al., Heparan sulfate D-glucosaminyl 3-O-sulfotransferase-3A sulfates N-unsubstituted glucosamine residues. J Biol Chem. Dec. 31, 1999;274(53):38155-62.

Lohse et al., Purification and characterization of heparin lyases from *Flavobacterium heparinum*. J Biol Chem. Dec. 5, 1992;267(34):24347-55.

McLean et al., *Flavobacterium heparium* 2-O-sulphatase for 2-O-sulphato-delta 4,5-glycuronate-terminated oligosaccharides from heparin. Eur. J Biochem, Dec. 17, 1984;145(3):607-15.

Murata et al., Characterization of the products generated from oversulphated dermatan sulphate isomers with chondroitinase-B by high-performance liquid chromatography. J Chromatogr. Dec. 25, 1987;423:51-61. Abstract Only.

Myette et al., Molecular cloning of the heparin/heparan sulfate delta 4,5 unsaturated glycuronidase from *Flavobacterium heparinum*, its recombinant expression in *Escherichia coli*, and biochemical determination of its unique substrate specificity. Biochemistry. Jun. 11, 2002;41(23):7424-34.

Myette et al., Expression in *Escherichia coli*, purification and kinetic characterization of human heparan sulfate 3-O-sulfotransferase-1, Biochem Biophys Res Commun. Feb. 1, 2002;290(4):1206-13.

Myette et al., The heparin/heparan sulfate 2-O-sulfatase from *Flavobacterium heparinum*. Molecular cloning, recombinant expression, and biochemical characterization. J Biol Chem. Apr. 4, 2003;278(14):12157-66.

Nakano et al., Study of sulfated glycosaminoglycans from porcine skeletal muscle epimysium including analysis of iduronosyl and glucuronosyl residues in galactosaminoglycan fractions. J. Agricult and Food Chem. 1996;44(6):1424-34. Abstract Only.

Petitou et al., Synthetic oligosaccharides having various functional domains: potent and potentially safe heparin mimetics. Bioorg Med Chem Lett. Apr. 19, 1999;9(8):1161-6.

Prabhakar et al., Chondroitinase ABC I from *Proteus vulgaris*: cloning, recombinant expression and active site identification. Biochem J. Feb. 15, 2005;386(Pt 1):103-12.

Prabhakar et al., Biochemical characterization of the chondroitinase ABC I active site. Biochem J. Sep. 1, 2005;390(Pt 2):395-405.

Raman et al., Structural insights into biological roles of protein-glycosaminoglycan interactions. Chem Biol. Mar. 2005;12(3):267-77.

Raman et al., The heparin/heparan sulfate 2-O-sulfatase from *Flavobacterium heparium*. A structural and biochemical study of the enzyme active site and saccharide substrate specificity. J Biol Chem. Apr. 4, 2003;278(14):12167-74.

Razi et al., Structural and functional properties of heparin analogues obtained by chemical sulphation of *Escherichia coli* K5 capsular polysaccharide. Biochem J. Jul. 15, 1995;309 (Pt 2):465-72.

Sasisekharan et al., Heparinase I from *Flavobacterium heparinum*: the role of the cysteine residue in catalysis as probed by chemical modification and site-directed mutagenesis. Biochemistry. Nov. 7, 1995;34(44):14441-8.

Sasisekharan et al., Heparinase inhibits neovascularization. Proc Natl Acad Sci U S A. Feb. 15, 1994;91(4):1524-8.

Satake et al., Enzymatic determination of urinary glycosaminoglycans from orthopedic patients. Tohoku J Exp Med. May 1983;140(1):89-96. Abstract Only.

Sato et al., Cloning and expression in *Escherichia coli* of the gene encoding the *Proteus vulgaris* chondroitin ABC lyase. Appl Microbiol Biotechnol. Mar. 1994;41(1):39-46.

Shriver et al., Biochemical investigations and mapping of the calcium-binding sites of heparinase I from *Flavobacterium heparinum*. J Biol Chem. Feb. 12, 1999;274(7):4082-8.

Takagaki et al., Analysis of glycosaminoglycans by high-performance liquid chromatography. J Biochem Biophys Methods. Jun. 1994;28(4):313-20. Abstract Only.

Vlodavsky et al., Mammalian heparanase: gene cloning, expression and function in tumor progression and metastasis. Nat Med. Jul. 1999;5(7):793-802.

Xiang et al., A method to increase contaminant tolerance in protein matrix-assisted laser desorption/ionization by the fabrication of thin protein-doped polycrystalline films. Rapid Comm in Mass Spect. 1994;8:199-204.

Warnick et al., Purification of an unusual -glycuronidase from flavobacteria. Biochemistry. Feb. 15, 1972;11(4):568-72.

Yang et al., Purification and characterization of heparinase from *Flavobacterium heparinum*. J Biol Chem. 1985;260(3):1849-57.

Yates et al., 1H and 13C NMR spectral assignments of the major sequences of twelve systemically modified heparin derivatives. Carbohydr Res. Nov. 20, 1996;294:15-27.

Yoder et al., New domain motif: the structure of pectate lyase C, a secreted plant virulence factor. Science. Jun. 4, 1993;260(5113):1503-7.

Yoder et al., Unusual structural features in the parallel beta-helix in pectate lyases. Structure. Dec. 15, 1993;1(4):241-51.

Yosizawa et al., A simple method for the quantitation of glycuronic acid-containing glycosaminoglycans with mucopolysaccharidases. Anal Biochem. Jan. 1983;128(1):250-6. Abstract.

Zhang et al., 6-O-sulfotransferase-1 represents a critical enzyme in the anticoagulant heparan sulfate biosynthetic pathway. J Biol Chem. Nov. 9, 2001;276(45):42311-21.

\* cited by examiner

METHODS FOR PURIFYING AND ISOLATING RECOMBINANT CHONDROITINASES

RELATED APPLICATIONS

This application is a divisional of U.S. application Ser. No. 10/454,816, filed Jun. 3, 2003 now U.S. Pat. No. 6,962,699, which claims priority under 35 U.S.C. § 119 from U.S. provisional application Ser. No. 60/385,509, filed Jun. 3, 2002, the entire contents of all of which are herein incorporated by reference.

GOVERNMENT SUPPORT

Aspects of the invention may have been made using funding from National Institutes of Health Grant number Grant GM 57073. Accordingly, the Government may have rights in the invention.

FIELD OF THE INVENTION

The invention relates to rationally designed polysaccharide lyases and uses thereof. In particular, the invention relates to modified chondroitinase B. The modified chondroitinase B enzymes of the invention are useful for a variety of purposes, including cleaving and sequencing polysaccharides such as glycosaminoglycans (GAGs) as well as removing polysaccharides from a solution and therapeutic methods such as inhibiting anticoagulant activity, inhibiting angiogenesis, treating cancer, and inhibiting maternal malarial infection.

BACKGROUND OF THE INVENTION

Glycosaminoglycans (GAGs) are linear, acidic polysaccharides that exist ubiquitously in nature as residents of the extracellular matrix and at the cell surface of many different organisms of divergent phylogeny (Habuchi, O. (2000) Biochim Biophys Acta 1474, 115–27; Sasisekharan, R., Bulmer, M., Moremen, K. W., Cooney, C. L., and Langer, R. (1993) Proc Natl Acad Sci USA 90, 3660–4). In addition to a structural role, GAGs act as critical modulators of a number of biochemical signaling events (Tumova, S., Woods, A., and Couchman, J. R. (2000) Int J Biochem Cell Biol 32, 269–88) requisite for cell growth and differentiation, cell adhesion and migration, and tissue morphogenesis.

Dermatan sulfate (DS) and chondroitin sulfate (CS) are related glycosaminoglycans (GAGs) that are composed of a disaccharide repeat unit of uronic acid (1→3)-linked to N-acetyl-D-galactosamine (GalNAc). These disaccharide repeats are (1→4)-linked to each other to form polymers of chondroitin sulfate or dermatan sulfate. Epimerization at the C5 position of the uronic acid moiety during the biosynthesis of dermatan sulfate leads to a mixture of L-iduronic and D-glucuronic acid epimers (Ernst, S., Langer, R., Cooney, C. L., and Sasisekharan, R. (1995) Crit. Rev. Biochem. Mol. Biol. 30, 387–444). In addition to C5 epimerization, C4 sulfation of GalNAc is another hallmark modification of the DS backbone. Rare sulfation at the 2-O and 3-O positions of the uronic acid moiety has also been reported (Sugahara, K., Tanaka, Y., Yamada, S., Seno, N., Kitagawa, H., Haslam, S. M., Morris, H. R., and Dell, A. (1996) J. Biol. Chem. 271, 26745–54; Nadanaka, S., and Sugahara, K. (1997) Glycobiology 7, 253–63). CS/DS polysaccharides have been implicated in a variety of biological phenomena ranging from anticoagulation to osteoarthritis (Mascellani, G., Liverani, L., Bianchini, P., Parma, B., Torri, G., Bisio, A., Guerrini, M., and Casu, B. (1993) Biochem. J. 296, 639–48; Achur, R. N., Valiyaveettil, M., Alkhalil, A., Ockenhouse, C. F., and Gowda, D. C. (2000) J. Biol. Chem. 275, 40344–56; and Plaas, A. H., West, L. A., Wong-Palms, S., and Nelson, F. R. (1998) J. Biol. Chem. 273, 12642–9). In fact, specific sequences of highly sulfated dermatan sulfate from a variety of invertebrate and mammalian sources are being pursued as pharmaceutically viable treatments for specific blood coagulation disorders (Monagle, P. et al. (1998) J. Biol. Chem. 273, 33566–71; Gandra, M. et al. (2000) Glycobiology 10, 1333–40; and Vicente, C. P. et al. (2001) Thromb. Haemost. 86, 1215–20). Changes in the dermatan sulfate side chain of the small proteoglycan, decorin, have been observed in human colon cancer (Daidouji, K. et al. (2002) Dig. Dis. Sci. 47, 331–7). And modification of existing GAG sequences by chondroitinase B and chondroitinase AC may inhibit angiogenesis and tumor metastasis (Denholm, E. M. et al. (2001) Eur. J. Pharmacol. 416, 213–21). Overall, the role of GAGs as specific mediators of tumorigenesis and other biological events is an emerging field that offers great potential for the development of novel therapeutics (Shriver, Z. et al. (2002) Trends. Cardiovasc. Med. 12, 71–7; and Liu, D. et al. (2002) Proc. Natl. Acad. Sci. USA 99, 568–73).

Flavobacterium heparinum is a common source for GAG-degrading lyases, producing both the extensively characterized heparin-degrading heparinases (Sasisekharan, R., Venkataraman, G., Godavarti, R., Ernst, S., Cooney, C. L., and Langer, R. (1996) J. Biol. Chem. 271, 3124–31; Shriver, Z., Hu, Y., Pojasek, K., and Sasisekharan, R. (1998) J. Biol. Chem. 273, 22904–12; Pojasek, K., Shriver, Z., Hu, Y., and Sasisekharan, R. (2000) Biochemistry 39, 4012–9; and Gu, K., Linhardt, R. J., Laliberte, M., and Zimmermann, J. (1995) Biochem. J. 312, 569–77), as well as the CS/DS-degrading chondroitinases (Gu, K. et al. (1995) Biochem. J. 312, 569–77). Chondroitinase B is the only member of the chondroitinase family that degrades DS as its sole substrate (Jandik, K. A., Gu, K., and Linhardt, R. J. (1994) Glycobiology 4, 289–96 and Pojasek, K., Shriver, Z., Kiley, P., Venkataraman, G., and Sasisekharan, R. (2001) Biochem. Biophys. Res. Commun. 286, 343–51).

SUMMARY OF THE INVENTION

The present invention relates, in part, to modified polysaccharide lyases. In particular, the invention relates to modified chondroitinase B. The characterization of the chondroitinase B active site, specifically the individual residues involved in substrate binding and catalysis allows for the rational design of modified chondroitinase B enzymes described herein. Additionally, the modified enzymes may be used for a variety of purposes due to the ability of the enzymes to uniquely cleave polysaccharides such as the glycosaminoglycans chondroitin sulfate and dermatan sulfate, or compete with native enzyme for substrate.

The invention, therefore, in some aspects is a modified chondroitinase B having an amino acid sequence of the mature peptide of SEQ ID NO: 2 or conservative substitutions thereof, wherein at least one residue at a position selected from the group consisting of 116, 184, 213, 219, 245, 250, 271, 272, 296, 298, 318, 333, 363 and 364 of SEQ ID NO: 2 has been substituted or deleted. In other embodiments the modified chondroitinase B has the amino acid sequence of the mature peptide of SEQ ID NO: 2 wherein at least one amino acid residue has been substituted and wherein the substituted amino acid is at a position selected from the group consisting of 272, 333, and 364 of SEQ ID NO: 2. In still other embodiments the modified chondroitinase B has the amino acid sequence of the mature peptide of SEQ ID NO: 2 wherein at least one amino acid residue has been substituted and wherein the substituted amino acid is at a position selected from the group consisting of 272, 333, 363 and 364 of SEQ ID NO: 2. In further embodiments, the modified chondroitinase B has the amino acid sequence of the mature peptide of SEQ ID NO: 2 wherein at least one residue has been substituted and wherein the substituted amino acid is at position 364 of SEQ ID NO: 2. In another aspect, modified chondroitinase B enzymes contain at least one substitution but maintain one or more of the residues with binding or catalytic activity recited herein. In one embodiment, the residue is residue at position 116, 184, 213, 219, 245, 250, 271, 272, 296, 298, 318, 333, 363 or 364 of SEQ ID NO: 2. In another embodiment the residue is at position 250 of SEQ ID NO: 2.

The modified chondroitinase B enzymes may also be described as having a modified product profile due to the interaction of the enzyme with substrate. The invention in some aspects is a modified chondroitinase B having a modified product profile, wherein the modified product profile of the modified chondroitinase B is at least 10% different than a native product profile of a native chondroitinase B. In other embodiments the modified product profile of the modified chondroitinase B is at least 50% different than a native product profile of a native chondroitinase B. In still other embodiments the modified product profile is at least 20% different than a native product profile of a native chondroitinase B.

In other aspects a modified chondroitinase B having a $k_{cat}$ or $K_M$ value for a substrate that is at least 10% different than a native chondroitinase B $k_{cat}$ or $K_M$ value is provided. In other embodiments the $k_{cat}$ or $K_M$ value is at least 20% different than a native chondroitinase B $k_{cat}$ or $K_M$ value. In still other embodiments the $k_{cat}$ or $K_M$ value is at least 50% different than a native chondroitinase B $k_{cat}$ or $K_M$ value.

The invention in some aspects also provides an enzyme, characterized by an active site organized in a three dimensional space along an axis composed of 4 regions identified as −2, −1, +1, and +2 and including at least the following amino acid residues positioned along the axis at the defined points 4 basic amino acids and 1 polar amino acid in −2 region, 2 basic amino acids and 1 acidic amino acid in −1 region and +1 region, and 2 basic amino acids in +2 region, wherein the enzyme does not have the primary sequence of native chondroitinase B. In some embodiments of the invention the enzyme includes at least the following amino acid residues positioned along the axis at the defined points 4 Arg, and 1 Phe in −2 region, 1 Asn, 1 Glu, and 1 Arg in −1 region, 1 Lys, 1 Glu, and 1 His in +1 region, and 1 His and 1 Arg in +2 region. In still other embodiments the enzyme comprises 1 Arg and 1 Trp in −1 region.

In some embodiments of the aforementioned enzymes, the substituted amino acid is a conservative amino acid substitution. In other embodiments, the enzyme is a substantially purified recombinant form. In some embodiments the substrate for the enzyme is a polysaccharide. In still other embodiments the substrate is a long polysaccharide. In still other embodiments the polysaccharide is a decasaccharide. In yet other embodiments the polysaccharide is an octa-, hexa- or tetrasaccharide. In yet another embodiment the substrate for the enzymes is a glycosaminoglycan.

The modified chondroitinase B and preparations may be utilized for various purposes. In some aspects a method of specifically cleaving chondroitin sulfate, comprising contacting chondroitin sulfate with the modified chondroitinase B is provided. In other embodiments the method is a method of specifically cleaving dermatan sulfate. In other embodiments a method of removing chondroitin sulfate from a chondroitin sulfate containing fluid is provided. In still other embodiments the method is a method of removing dermatan sulfate from a dermatan sulfate containing fluid. The method is, in some embodiments, a method for sequencing chondroitin sulfate oligosaccharides. In other embodiments the method is a method for sequencing dermatan sulfate oligosaccharides. The invention also provides in some aspects an immobilized modified chondroitinase B comprising a modified chondroitinase and a solid support membrane, wherein the modified chondroitinase B is immobilized on the solid support membrane.

In some aspects a method of analyzing a sample of polysaccharides, comprising contacting the sample with the modified chondroitinase B is provided. Another aspect is a method of identifying the presence of a particular polysaccharide in a sample. In still other aspects a method of determining the purity of sample of polysaccharides is provided. In yet other aspects a method for determining the composition of a sample of polysaccharides is provided.

In some aspects the invention relates to a method for purifying or isolating a recombinant enzyme. In some embodiments the recombinant enzyme is a polysaccharide degrading enzyme. In still another embodiment the recombinant enzyme is a chondroitinase. The method may involve the induction of a culture of cells containing a recombinant chondroitinase with an inducing agent for greater than four hours, followed by isolation of the recombinant chondroitinase from the cells to produce a purified chondroitinase. The method may also involve lysing a cell culture containing a recombinant chondroitinase having a terminal Histidine tag, and passing the recombinant chondroitinase over a charged Ni 2+ column to isolate the recombinant chondroitinase. According to yet other embodiments the inducing agent is isopropyl-B-D-thiogalactopyranoside (IPTG).

In some embodiments the cells are incubated with the inducing agent at a temperature of between 20° and 26° C. In other embodiments the cells are incubated with the inducing agent for at least 8 hours. In yet other embodiments the chondroitinase is chondroitinase AC or B. In yet other embodiments, the chondroitinase is a modified chondroitinase B.

The modified chondroitinase B or glycosaminoglycan fragment produced with the modified chondroitinase B is also useful for therapeutic purposes. The method in some embodiments is directed to modulating a condition with the modified chondroitinase B or glycosaminoglycan fragment. The invention in some embodiments is a method for inhibiting angiogenesis, by administering to a subject an effective amount of chondroitinase B for inhibiting angiogenesis. In other embodiments the chondroitinase B is administered directly to a tumor. A method for inhibiting maternal malarial infection, by administering to a subject in need thereof an effective amount for maternal malarial infection of the modified chondroitinase B is also provided. In some embodiments a method for inhibiting anticoagulant activity of dermatan sulfates, comprising administering to a subject in need thereof an effective amount for inhibiting anticoagulant activity of dermatan sulfates of the modified chondroitinase B is also provided. In still other embodiments a method for treating osteoarthritis is provided. In other embodiments a method for treating cancer, by administering to a subject in need thereof an effective amount for treating cancer of the modified chondroitinase B is provided. In still other embodiments the cancer is metastatic cancer. In yet other embodiments methods for modulating mitogenic activity (e.g. FGF-7 mitogenic activity), enhancing hepatocyte growth factor/scatter factor activity and mediating cell signaling are provided.

In some embodiments a pharmaceutical preparation is provided comprising a sterile formulation of chondroitinase B and a pharmaceutically acceptable carrier. In other embodiments a pharmaceutical preparation is provided comprising a glycosmaminoglycan fragment. In other embodiments the pharmaceutical preparation comprises a combination of different glycosaminoglycan fragments. Glycosaminoglycan fragments can be produced by the action of a modified chondroitinase B alone or in combination with other enzymes. In other embodiments the chondroitinase B is administered in a biodegradable, biocompatible polymeric delivery device. In still other embodiments the chondroitinase B or glycosaminoglycan fragment is administered in a pharmaceutically acceptable vehicle for injection.

Each of the limitations of the invention can encompass various embodiments of the invention. It is, therefore, anticipated that each of the limitations of the invention involving any one element or combinations of elements can be included in each aspect of the invention.

DETAILED DESCRIPTION

Figure 1A:
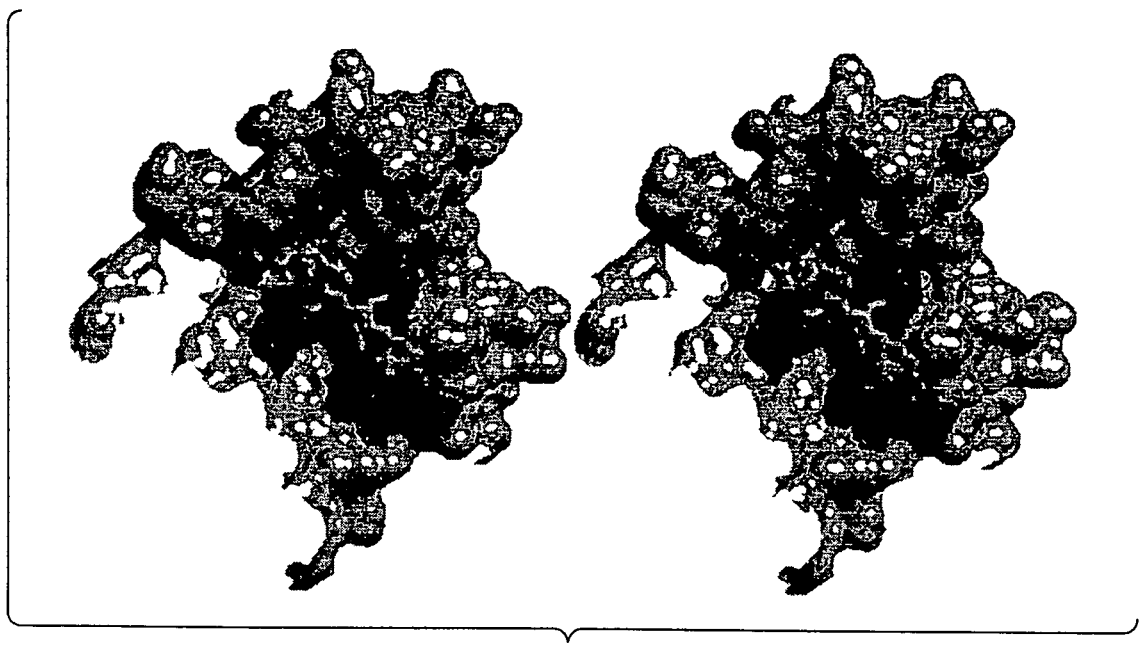
FIG. 1 represents the docking of the dermatan sulfate substrate in the active site of chondroitinase B. (A) Stereoview of conolly surface rendering of the active site of chondroitinase B with the docked dermatan sulfate tetrasaccharide (green) and disaccharide product (orange) whose orientation is replicated from the co-crystal structure. Although the direction of both the disaccharide product and the tetrasaccharide is the same from non-reducing end (close to C terminus above active site) to reducing end (close to N-terminus below the active site), the tetrasaccharide is positioned to completely occupy the active site. (B) Stick representation of the dermatan sulfate tetrasaccharide in the active site of chondroitinase B, colored according to the atoms (C: green, N: blue, O: red and S: yellow) (left) and the two dimensional schematic distribution of the active site residues (right). The side chains of the residues (single letter code and number) of the protein interacting with the tetrasaccharide are shown. Basic residues (Lys, Arg, Asn, His) are colored blue, acidic residues (Glu) are colored red, and bulky aromatic residues (Phe, Trp) are colored purple. The subsite nomenclature is used to define the orientation of the tetrasaccharide from −2 (nonreducing end) to +2 (reducing end) in the active site. Cleavage occurs between the −1 and +1 site.

Dermatan sulfate (DS) is a member of the glycosaminoglycan (GAG) family of complex polysaccharides that also includes chondroitin sulfate (CS), heparin/heparan sulfate (HSGAG), keratan sulfate, and hyaluronic acid. Chondroitin sulfate and dermatan sulfate glycosaminoglycan polysaccharides, have been implicated in biological processes ranging from osteoarthritis to anticoagulation. Dermatan sulfate is emerging as an important regulator of cellular signaling processes. An over-sulfated hexasaccharide found in DS that binds heparin cofactor II and promotes a 1000-fold increase in anticoagulation is the most characterized biological paradigm for DS (Maimone, M. M., and Tollefsen, D. M. (1991) J Biol Chem 266, 14830; Mascellani, G., Liverani, L., Bianchini, P., Parma, B., Torri, G., Bisio, A., Guerrini, M., and Casu, B. (1993) Biochem J 296, 639–48). Several recent studies have implicated DS in promoting FGF-7 mitogenic activity (Trowbridge, J. M., Rudisill, J. A., Ron, D., and Gallo, R. L. (2002) J Biol Chem 277, 42815–20) and enhancing the activity of hepatocyte growth factor/scatter factor (Lyon, M., Deakin, J. A., Rahmoune, H., Fernig, D. G., Nakamura, T., and Gallagher, J. T. (1998) J Biol Chem 273, 271–8; Lyon, M., Deakin, J. A., and Gallagher, J. T. (2002) J Biol Chem 277, 1040–6), suggesting an important role for DS in mediating cell signaling. One of the major hurdles in studying the biochemistry of DS as well as the other GAGs has been dealing with their overall structural heterogeneity and negative charge (Ernst, S., Langer, R., Cooney, C. L., and Sasisekharan, R. (1995) Crit Rev Biochem Mol Biol 30, 387–444).

Found as a proteoglycan linked to a variety of core proteins on the cell surface or in the extracellular matrix, DS chains are composed a disaccharide repeat of a uronic acid $\alpha/\beta(1\rightarrow3)$-linked to a N-acetyl-D-galactosamine (GalNAc). Each disaccharide unit is, in turn, $\beta(1\rightarrow4)$-linked to an adjacent disaccharide forming the DS chain (Trowbridge, J. M., and Gallo, R. L. (2002) Glycobiology 12, 117R–25R). The hallmark modification of DS is sulfation at the 4-O position of the GalNAc with sulfation also occurring at the 2-O position of the uronic acid and 6-O position of the GalNAc and rare sulfation at the 3-O position of the uronic acid (Ernst, S., Langer, R., Cooney, C. L., and Sasisekharan, R. (1995) Crit Rev Biochem Mol Biol 30, 387–444; Sugahara, K., Tanaka, Y., Yamada, S., Seno, N., Kitagawa, H., Haslam, S. M., Morris, H. R., and Dell, A. (1996) J Biol Chem 271, 26745–54). In addition, the uronic acid can be epimerized at the C5 position from glucuronic acid (GlcA) to iduronic acid (IdoA) leading to further structural heterogeneity (Ernst, S., Langer, R., Cooney, C. L., and Sasisekharan, R. (1995) Crit Rev Biochem Mol Biol 30, 387–444).

Polysaccharide lyases have important utility not only for elucidating the structure and function of these glycosaminoglycans but also for therapeutic purposes due to their cleavage of these substrates. Chondroitinase B from *Flavobacterium heparinum* is the only known lyase that cleaves dermatan sulfate as its sole substrate (Ernst, S., Langer, R., Cooney, C. L., and Sasisekharan, R. (1995) Crit Rev Biochem Mol Biol 30, 387–444). The sequence of chondroitinase B is well known in the art. For instance, GenBank Accession number U27584 provides the nucleic acid and amino acid sequence of chondroitinase B from *Flavobacterium heparinum*. SEQ ID NO: 1 is the nucleic acid of chondroitinase B, while SEQ ID NO: 2 provides the amino acid sequence. The GenBank record further provides the sequences of the signal and mature peptides. The "mature peptide" is the sequence of chondroitinase B sans the signal peptide sequence. The nucleic acid and amino acid sequences of chondroitinase B from *Flavobacterium heparinum* are also provided is U.S. issued patents U.S. Pat. Nos. 6,054,569 and 6,093,563, issued Apr. 25, 2000 and Jul. 25, 2000, respectively. Additional information from crystal structures of chondroitinase B are also provided in GenBank (e.g. GenBank Accession numbers 1DBOA and 1DBGA).

GAG-degrading lyases, such as chondroitinase B, from *F. heparinum* are thought to cleave their DS substrates through a concerted β-elimination mechanism originally proposed by Gassman and Gerlt (Gerlt, J. A., and Gassman, P. G. (1993) *Biochemistry* 32, 11943–52). The first step in the proposed reaction is the abstraction of the C5 proton on the GalNAc moiety by a basic amino acid forming an enolate intermediate. The enzyme stabilizes this carbanion intermediate usually via a positively charged, hydrophilic amino acid (Gerlt, J. A., and Gassman, P. G. (1993) *Biochemistry* 32, 11943–52 and Gacesa, P. (1992) *Int. J. Biochem.* 24, 545–52). The final step of reaction mechanism involves protonation of the anomeric oxygen by an acidic residue with concomitant β-elimination of the uronic acid resulting an unsaturated $\Delta^{4,5}$ bond (Gerlt, J. A., and Gassman, P. G. (1993) *Biochemistry* 32, 11943–52 and Gacesa, P. (1992) *Int. J. Biochem.* 24, 545–52).

The roles of specific active site amino acids in the catalytic function of chondroitinase B were assessed by docking a dermatan sulfate tetrasaccharide into the proposed active site of the enzyme. Our conformational analysis also revealed a unique, symmetrical arrangement of active site amino acids that may impinge on the catalytic mechanism of action of chondroitinase B. The catalytic residues, Lys250, Arg271, His272, and Glu333 along with the substrate binding residues, Arg363 and Arg364, were mutated using site-directed mutagenesis, and the kinetics and product profile of each mutant were compared to recombinant chondroitinase B. Mutating Lys250 to alanine resulted in inactivation of the enzyme, potentially attributable to the residue's role in stabilizing the carbanion intermediate formed during enzymatic catalysis. The His272 and Glu333 mutants showed diminished enzymatic activity that could be indicative of a possible role for one or both residues in the abstraction of the C5 proton from the galactosamine. In addition, the Arg364 mutant had an altered product profile after exhaustive digestion of dermatan sulfate suggesting a role for this residue in defining the substrate specificity of chondroitinase B. The Arg364 mutant exhibited altered the enzyme's kinetic activity likely through changes in substrate binding. This demonstrates an altered mode of action pattern confirming this residue's role in substrate processing.

Several discoveries described herein therefore contribute to the molecular understanding of chondroitinase B depolymerization of CS/DS oligosaccharides. Based on our molecular characterization of chondroitinase B, both H272A and E333A showed altered kinetics when compared with the recombinant chondroitinase B. Both of these mutations lead to a slight reduction in $K_m$ while drastically reducing $k_{cat}$. In addition to kinetic analysis, each of the mutant enzymes and the recombinant chondroitinase B were allowed to exhaustively digest dermatan sulfate to determine changes in product profile. A comparison between the ratio of the $\Delta$UA-GalNAc4S peak to the total peak area of the mutant digests and the recombinant enzyme showed that H272A and E333A demonstrated full enzymatic activity suggesting that, while His272 and Glu333 are important in the active site chemistry, chondroitinase B can still function without them. The His272 and Glu333 mutants' diminished enzymatic activity could be indicative of a possible role for one or both residues in the abstraction of the C5 proton from the galactosamine. Changing Lys250, however, to alanine ablated the activity of chondroitinase B suggesting that Lys250 is important for the catalytic activity of chondroitinase B, likely attributable to the residue's role in stabilizing the carbanion intermediate formed during enzymatic catalysis. Along with the active site residues discussed above, Arg271 was mutated to alanine. The R271A mutant was expressed at comparable levels to the recombinant chondroitinase B, but was completely insoluble. Taken together, these results suggest that Lys250, His272, Glu333, and possibly Arg271 are involved in the catalytic degradation of dermatan sulfate by chondroitinase B.

In addition to catalytic residues, two basic residues proximal to subsites −1 and −2, Arg363 and Arg364, were selected for mutagenesis. The R363A mutant had a two-fold increase in $k_{cat}/K_m$ which suggests that removal of Arg363 allows for a slight increase in catalytic efficiency in chondroitinase B. In contrast, mutating Arg364 to alanine led to a loss of activity in the real-time kinetic assay and an altered product profile after exhaustive digestion of dermatan sulfate. As suggested by our analyses, Arg364 is important for the proper substrate binding and digestion of dermatan sulfate by chondroitinase B. From compositional analysis it also appears that Arg364 is involved in chondroitinase B's ability to recognize and cleave regions containing $\Delta$UA-GalNAc4S,6S in dermatan sulfate.

One of ordinary skill in the art is enabled, in light of the present disclosure, to produce modified chondroitinase B by standard technology, including recombinant technology, direct synthesis, mutagenesis, etc. For instance, one may produce the modified chondroitinase B having an amino acid sequence of the mature peptide of SEQ ID NO: 2 or conservative substitutions thereof, wherein at least one residue at a position selected from the group consisting of 116, 184, 213, 219, 245, 250, 271, 272, 296, 298, 318, 333, 363 and 364 of SEQ ID NO: 2 has been substituted or deleted. One of skill in the art may also substitute appropriate codons to produce the desired amino acid substitutions in SEQ ID NO:2 by standard site-directed mutagenesis techniques. It is possible to use any sequence which differs from the nucleic acid equivalents of SEQ ID NO:2 only due to the degeneracy of the genetic code as the starting point for site directed mutagenesis. The mutated nucleic acid sequence may then be ligated into an appropriate expression vector and expressed in a host such as *F. heparinum* or *E. coli*. The resultant modified chondroitinase B may then be purified by techniques known by those of ordinary skill in the art, including those disclosed below.

In some embodiments the modified chondroitinase B is in substantially pure form. As used herein, the term "substantially pure" means that the proteins are essentially free of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations. Polypeptides can be isolated from biological samples, and can also be expressed recombinantly in a variety of prokaryotic and eukaryotic expression systems by constructing an expression vector appropriate to the expression system, introducing the expression vector into the expression system, and isolating the recombinantly expressed protein. Polypeptides can also be synthesized chemically using well-established methods of peptide synthesis. In some embodiments, chondroitinase B in a substantially purified recombinant form is a preparation of modified chondroitinase B which has been recombinantly synthesized and which is greater then 90% free of contaminants. Preferably, the material is greater than 91%, 92%, 93%, 94%, 95%, 96%, 97%, 98%, or even greater then 99% free of contaminants. The degree of purity may be assessed by means known in the art.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. Because an isolated polypeptide may be admixed with a pharmaceutically acceptable carrier in a pharmaceutical preparation, the polypeptide may comprise only a small percentage by weight of the preparation. The polypeptide is nonetheless isolated in that it has been separated from the substances with which it may be associated in living systems, i.e., isolated from other proteins.

A "modified chondroitinase B polypeptide" is a polypeptide which contains one or more modifications to the primary amino acid sequence of a chondroitinase B polypeptide. Modifications which create a modified chondroitinase B polypeptide may be made recombinantly to the nucleic acid which encodes the modified chondroitinase B polypeptide, and can include deletions, point mutations, truncations, amino acid substitutions and addition of amino acids or non-amino acid moieties to (as described herein): 1) alter enzymatic activity; 2) provide a novel activity or property to a modified chondroitinase B polypeptide, such as addition of a detectable moiety; or 3) to provide equivalent, greater or lesser interaction with other molecules (e.g., chondroitin sulfate and dermatan sulfate). Alternatively, modifications can be made directly to the polypeptide, such as by cleavage, and the like. Modifications also embrace fusion proteins comprising all or part of the modified chondroitinase B amino acid sequence.

Mutations can be made by selecting an amino acid substitution, or by random mutagenesis of a selected site in a nucleic acid which encodes the polypeptide. Modified polypeptides are then expressed and tested for one or more activities to determine which mutation provides a modified polypeptide with the desired properties.

Methods for making amino acid substitutions, additions or deletions are well known in the art. The terms "conservative substitution", "non-conservative substitutions", "non-polar amino acids", "polar amino acids", and "acidic amino acids" are all used consistently with the prior art terminology. Each of these terms is well-known in the art and has been extensively described in numerous publications, including standard biochemistry text books, such as "Biochemistry" by Geoffrey Zubay, Addison-Wesley Publishing Co., 1986 edition, which describes conservative and non-conservative substitutions, and properties of amino acids which lead to their definition as polar, non-polar or acidic.

One type of amino acid substitution is referred to as a "conservative substitution." As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs or variants.

Additionally, some of the amino acid substitutions are non-conservative substitutions. Non-conservative substitutions, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain.

The modified chondroitinase B has specific substitutions in specified portions of the peptide. In addition to these substitutions which may be conservative or non-conservative, other regions of the peptide may include conservative substitutions that do not impact the activity of the modified chondroitinase B. One skilled in the art will appreciate that the effect of a particular substitution can be evaluated by routine screening assays, preferably the biological assays described herein.

According to the invention, isolated nucleic acid molecules that code for a modified chondroitinase B polypeptide are provided and include: (a) nucleic acid molecules which hybridize under stringent conditions to the nucleic acid equivalent which codes for a modified chondroitinase B polypeptide as described herein or parts thereof, (b) deletions, additions and substitutions of (a) which code for a respective modified chondroitinase B polypeptide or parts thereof, (c) nucleic acid molecules that differ from the nucleic acid molecules of (a) or (b) in codon sequence due to the degeneracy of the genetic code, and (d) complements of (a), (b) or (c).

In certain embodiments, the nucleic acid molecule that codes for a modified chondroitinase B is highly homologous to the nucleic acid molecules described herein. Preferably the homologous nucleic acid molecule comprises a nucleotide sequence that is at least about 90% identical to the nucleotide sequence provided herein. More preferably, the nucleotide sequence is at least about 95% identical, at least about 97% identical, at least about 98% identical, or at least about 99% identical to the nucleotide sequence provided herein. The homology can be calculated using various, publicly available software tools well known to one of ordinary skill in the art. Exemplary tools include the BLAST system available from the website of the National Center for Biotechnology Information (NCBI) at the National Institutes of Health.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

Optionally the modified chondroitinase B is recombinantly produced. Such molecules may be recombinantly produced using a vector including a coding sequence operably joined to one or more regulatory sequences. As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein the coding sequences are operably joined to regulatory sequences. Two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Promoters may be constitutive or inducible. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The term "high stringency conditions" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. One example of high-stringency conditions is hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1–0.5×SSC/0.1×SDS at temperatures up to 68° C. There are other conditions, reagents, and so forth which can be used, which result in the same degree of stringency. A skilled artisan will be familiar with such conditions, and thus they are not given here.

The skilled artisan also is familiar with the methodology for screening cells for expression of such molecules, which then are routinely isolated, followed by isolation of the pertinent nucleic acid. Thus, homologs and alleles of the modified chondroitinase B, as well as nucleic acids encoding the same, may be obtained routinely, and the invention is not intended to be limited to the specific sequences disclosed.

For prokaryotic systems, plasmid vectors that contain replication sites and control sequences derived from a species compatible with the host may be used. Examples of suitable plasmid vectors include pBR322, pUC18, pUC19 and the like; suitable phage or bacteriophage vectors include λgt10, λgt11 and the like; and suitable virus vectors include pMAM-neo, pKRC and the like. Preferably, the selected vector of the present invention has the capacity to autonomously replicate in the selected host cell. Useful prokaryotic hosts include bacteria such as *E. coli, Flavobacterium heparinum, Bacillus, Streptomyces, Pseudomonas, Salmonella, Serratia*, and the like.

To express the modified chondroitinase B in a prokaryotic cell, it is desirable to operably join the nucleic acid sequence of a modified chondroitinase B to a functional prokaryotic promoter. Such promoter may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162: 176–182 (1985)) and the ζ-28-specific promoters of *B. subtilis* (Gilman et al., *Gene sequence* 32:11–20 (1984)), the promoters of the bacteriophages of *Bacillus* (Gryczan, In: *The Molecular Biology of the Bacilli*, Academic Press, Inc., NY (1982)), and *Streptomyces* promoters (Ward et al., *Mol. Gen. Genet.* 203:468–478 (1986)).

Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the encoding sequence. Such ribosome binding sites are disclosed, for example, by Gold et al. (*Ann. Rev. Microbiol.* 35:365–404 (1981)).

Because prokaryotic cells may not produce the modified chondroitinase B with normal eukaryotic glycosylation, expression of the modified chondroitinase B in eukaryotic hosts is useful when glycosylation is desired. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/0-AG14 or the myeloma P3x63Sg8, and their derivatives. Preferred mammalian host cells include SP2/0 and J558L, as well as neuroblastoma cell lines such as IMR 332 that may provide better capacities for correct post-translational processing. Embryonic cells and mature cells of a transplantable organ also are useful according to some aspects of the invention.

In addition, plant cells are also available as hosts, and control sequences compatible with plant cells are available, such as the nopaline synthase promoter and polyadenylation signal sequences.

Another preferred host is an insect cell, for example in *Drosophila* larvae. Using insect cells as hosts, the *Drosophila* alcohol dehydrogenase promoter can be used (Rubin, *Science* 240:1453–1459 (1988)). Alternatively, baculovirus vectors can be engineered to express large amounts of the modified chondroitinase B in insect cells (Jasny, *Science* 238:1653 (1987); Miller et al., In: *Genetic Engineering* (1986), Setlow, J. K., et al., eds., Plenum, Vol. 8, pp. 277–297).

Any of a series of yeast gene sequence expression systems which incorporate promoter and termination elements from the genes coding for glycolytic enzymes and which are produced in large quantities when the yeast are grown in media rich in glucose may also be utilized. Known glycolytic gene sequences can also provide very efficient transcriptional control signals. Yeast provide substantial advantages in that they can also carry out post-translational peptide modifications. A number of recombinant DNA strategies exist which utilize strong promoter sequences and high copy number plasmids which can be utilized for production of the desired proteins in yeast. Yeast recognize leader sequences on cloned mammalian gene sequence products and secrete peptides bearing leader sequences (i.e., pre-peptides).

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or which are subject to chemical (such as metabolite) regulation.

The modified chondroitinase B is useful as an enzymatic tool due to its substrate specificity and specific activity and for cleaving polysaccharides. The modified chondroitinase B may be used to specifically cleave a polysaccharide by contacting the polysaccharide substrate with the modified chondroitinase B. The invention is useful in a variety of in vitro, in vivo and ex vivo methods in which it is useful to cleave polysaccharides.

As used herein, a "polysaccharide" is a polymer composed of monosaccharides linked to one another. In many polysaccharides the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide). The term polysaccharide is also intended to embrace an oligosaccharide. Polysaccharides include but are not limited to glycosaminoglycans such as chondroitin sulfate, dermatan sulfate, heparin, heparin-like glycosaminoglycans (HLGAGs), heparan sulfate, hyaluronic acid, keratan sulfate, and derivatives or analogs thereof, chitin in derivatives and analogs thereof.

In addition to polysaccharides from natural sources, the polysaccharides of the invention also include molecules that are biotechnologically prepared, chemically modified and synthetic. The term "biotechnological prepared" encompasses polysaccharides that are prepared from natural sources of polysaccharides which have been chemically modified. This is described for example in Razi et al., Bioche. J. 1995 Jul. 15;309 (Pt 2): 465–72 and in Yates et al., Carbohydrate Res (1996) November 20;294:15–27, and is known to those of skill in the art. Synthetic polysaccharides are also well known to those of skill in the art and is described in Petitou, M. et al., Bioorg Med Chem Lett. (1999) Apr. 19;9(8):1161–6.

Analyses of polysaccharides as described in the present disclosure are possible using modified chondroitinase B alone or in conjunction with other enzymes. Other polysaccharide degrading enzymes include but are not limited to other chondroitinases (e.g. chondroitinase ABC and chondroitinase AC), hyaluronate lyase, heparinase-I, heparinase-II, heparinase-111, keratanase, D-glucuronidase and L-iduronidase, modified versions of these enzymes, variants and functionally active fragments thereof.

The methods that may be used to test the specific activity of modified chondroitinase B include those described in the Examples. The term "specific activity" as used herein refers to the enzymatic activity of a preparation of chondroitinase B. These methods may also be used to assess the function of variants and functionally active fragments of modified chondroitinase B. The $k_{cat}$ value may be determined using any enzymatic activity assay to assess the activity of a modified chondroitinase B enzyme. Several such assays are well-known in the art. For instance, an assay for measuring $k_{cat}$ is described in (Ernst, S. E., Venkataraman, G., Winkler, S., Godavarti, R., Langer, R., Cooney, C. and Sasisekharan. R. (1996) *Biochem. J.* 315, 589–597). The "native modified chondroitinase B $k_{cat}$ value" is the measure of enzymatic activity of the native modified chondroitinase B obtained from cell lysates of *F. heparinum* also described in the Examples below.

Due to the activity of modified chondroitinase B on polysaccharides, the product profile produced by a modified chondroitinase B may be determined by any method known in the art for examining the type or quantity of degradation product produced by modified chondroitinase B alone or in combination with other enzymes. One of skill in the art will also recognize that the modified chondroitinase B may also be used to assess the purity of polysaccharides in a sample. One preferred method for determining the type and quantity of product is described in Rhomberg, A. J. et al., *PNAS*, v. 95, p. 4176–4181 (April 1998), which is hereby incorporated in its entirety by reference. The method disclosed in the Rhomberg reference utilizes a combination of mass spectrometry and capillary electrophoretic techniques to identify the enzymatic products produced by heparinase. The Rhomberg study utilizes heparinase to degrade HLGAGs to produce HLGAG oligosaccharides. MALDI (Matrix-Assisted Laser Desorption Ionization) mass spectrometry can be used for the identification and semiquantitative measurement of substrates, enzymes, and end products in the enzymatic reaction. The capillary electrophoresis technique separates the products to resolve even small differences amongst the products and is applied in combination with mass spectrometry to quantitate the products produced. Capillary electrophoresis may even resolve the difference between a disaccharide and its semicarbazone derivative.

The modified chondroitinase may also be used as a tool to sequence polysaccharides. Detailed methods for sequencing polysaccharides and other polymers are disclosed in co-pending U.S. patent application Ser. Nos. 09/557,997 and 09/558,137, both filed on Apr. 24, 2000 and having common inventorship. The entire contents of both applications are hereby incorporated by reference. Briefly, the method is performed by enzymatic digestion, followed by mass spectrometry and capillary electrophoresis. The enzymatic assays can be performed in a variety of manners, as long as the assays are performed similarly on the modified chondroitinase B, so that the results may be compared. In the example described in the Rhomberg reference, enzymatic reactions are performed by adding 1 microliter of enzyme solution to 5 microliter of substrate solution. The digestion is then carried out at room temperature (22° C.), and the reaction is stopped at various time points by removing 0.5 microliter of the reaction mixture and adding it to 4.5 microliter of a MALDI matrix solution, such as caffeic acid (approximately 12 mg/mL) and 70% acetonitrile/water. The reaction mixture is then subjected to MALDI mass spectrometry. The MALDI surface is prepared by the method of Xiang and Beavis (Xiang and Beavis (1994) *Rapid. Commun. Mass. Spectrom.* 8, 199–204). A two-fold lower access of basic peptide $(Arg/Gly)_{15}$ is premixed with matrix before being added to the oligosaccharide solution. A 1 microliter aliquot of sample/matrix mixture containing 1–3 picomoles of oligosaccharide is deposited on the surface. After crystallization occurs (typically within 60 seconds), excess liquid is rinsed off with water. MALDI mass spectrometry spectra is then acquired in the linear mode by using a PerSeptive Biosystems (Framingham, Mass.) Voyager Elite reflectron time-of-flight instrument fitted with a 337 nanometer nitrogen laser. Delayed extraction is used to increase resolution (22 kV, grid at 93%, guidewire at 0.15%, pulse delay 150 ns, low mass gate at 1,000, 128 shots averaged). Mass spectra are calibrated externally by using the signals for proteinated $(Arg/Gly)_{15}$ and its complex with the oligosaccharide.

Capillary electrophoresis may then be performed on a Hewlett-Packard[3D] CE unit by using uncoated fused silica capillaries (internal diameter 75 micrometers, outer diameter 363 micrometers, $I_{det}$ 72.1 cm, and $I_{tot}$ 85 cm). Analytes are monitored by using UV detection at 233 nm and an extended light path cell (Hewlett-Packard). The electrolyte is a solution of 10 microliter dextran sulfate and 50 millimolar Tris/phosphoric acid (pH 2.5). Dextran sulfate is used to suppress nonspecific interactions of the glycosaminoglycan oligosaccharides with a silica wall. Separations are carried out at 30 kV with the anode at the detector side (reversed polarity). A mixture of a 1/5-naphtalenedisulfonic acid and 2-naphtalenesulfonic acid (10 micromolar each) is used as an internal standard.

Additionally, the coupling of CE and MALDI-MS with enzymes and a bioinformatics-based, property-encoded nomenclature (PEN) have led to a sequencing strategy (PEN-MALDI) described in (Venkataraman, G., Shriver, Z., Raman, R., and Sasisekharan, R. (1999) Science 286, 537–42).

Other methods for assessing the product profile may also be utilized. For instance, other methods include methods which rely on parameters such as viscosity (Jandik, K. A., Gu, K. and Linhardt, R. J., (1994), *Glycobiology*, 4:284–296) or total UV absorbance (Ernst, S. et al., (1996), *Biochem. J*, 315:589–597) or mass spectrometry or capillary electrophoresis alone.

One of ordinary skill in the art, in light of the present disclosure, is enabled to produce preparations of glycosaminoglycan (GAG) fragment compositions utilizing the modified chondroitinase B molecules alone or in conjunction with other enzymes. These GAG fragments have many therapeutic utilities. The GAG fragment preparations are prepared from polysaccharide sources. A "polysaccharide source" as used herein refers to glycosaminoglycan composition which can be manipulated to produce GAG fragments. As described above, GAGs include but are not limited to isolated chondroitin sulfate, dermatan sulfate as well as chemically modified, biotechnology prepared and synthetic versions of such polysaccharides. Thus GAGs can be isolated from natural sources, prepared by direct synthesis.

The term "GAG fragment" as used herein refers to a GAG which has therapeutic activity. For instance, the GAG fragment can prevent the proliferation and/or metastasis of a tumor cell. The use of the GAG fragments for other desired therapeutic activities are described below. Such compounds may be generated using modified chondroitinase B to produce therapeutic fragments or they may be synthesized de novo based on information derived from the use of modified chondroitinase B. Putative GAG fragments can be tested for therapeutic activity using any of the assays described herein or known in the art. Thus the therapeutic GAG fragment may be a synthetic GAG fragment generated based on the sequence of the GAG fragment identified when a polysaccharide source is contacted with modified chondroitinase B, or having minor variations which do not interfere with the activity of the compound. Alternatively the therapeutic GAG fragment may be an isolated GAG fragment produced when the polysaccharide source is contacted with modified chondroitinase B.

Thus, the methods of the invention enable one of skill in the art to prepare or identify an appropriate composition of GAG fragments, depending on the subject and the disorder being treated. These compositions of GAG fragments may be used alone or in combination with the modified chondroitinase B and/or other enzymes. Likewise modified chondroitinase B may also be used to produce GAG fragments in vivo.

The modified chondroitinase B molecules and/or GAG fragments produced using the modified chondroitinase B can be used for the treatment of any type of condition in which chondroitinase therapy or GAG fragment therapy has been identified as a useful therapy, e.g., preventing coagulation, inhibiting angiogenesis, inhibiting proliferation. The modified chondroitinase B and/or GAG fragments can also be used for mediating cell signaling. Thus, the invention is useful in a variety of in vitro, in vivo and ex vivo methods in which therapies are useful. For instance, it is known that GAG fragments and chondroitinase B are useful for preventing coagulation, inhibiting cancer cell growth and metastasis, preventing angiogenesis, preventing neovascularization, preventing psoriasis. Chondroitinase B is also useful in the treatment of ostoearthritis and maternal malarial infection. The GAG fragment compositions may also be used in in vitro assays, such as a quality control sample.

Each of these disorders is known in the art and is described, for instance, in *Harrison's Principles of Internal Medicine* (McGraw Hill, Inc., New York), which is incorporated by reference.

In one embodiment the preparations of the invention are used for inhibiting angiogenesis. An effective amount for inhibiting angiogenesis of the GAG fragment preparation or modified chondroitinase B is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. Several of the angiogenic mitogens are heparin binding peptides which are related to endothelial cell growth factors. The inhibition of angiogenesis can cause tumor regression in animal models, suggesting a use as a therapeutic anticancer agent. An effective amount for inhibiting angiogenesis is an amount of GAG fragment preparation or a modified chondroitinase B which is sufficient to diminish the number of blood vessels growing into a tumor. This amount can be assessed in an animal model of tumors and angiogenesis, many of which are known in the art.

The modified chondroitinase B molecules and GAG fragment preparation are useful for treating or preventing disorders associated with coagulation. A "disease associated with coagulation" as used herein refers to a condition characterized by inflammation resulting from an interruption in the blood supply to a tissue, which may occur due to a blockage of the blood vessel responsible for supplying blood to the tissue such as is seen for myocardial, cerebral infarction, or peripheral vascular disease, or as a result of embolism formation associated with conditions such as atrial fibrillation or deep venous thrombosis. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The modified chondroitinase B or the GAG fragments generated therewith may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulants include, but are not limited to, heparin, warfarin, coumadin, dicumarol, phenprocoumon, acenocoumarol, ethyl biscoumacetate, and indandione derivatives.

Antiplatelet agents include, but are not limited to, aspirin, thienopyridine derivatives such as ticlopodine and clopidogrel, dipyridamole and sulfinpyrazone, as well as RGD mimetics and also antithrombin agents such as, but not limited to, hirudin.

Thrombolytic agents include, but are not limited to, plasminogen, a2-antiplasmin, streptokinase, antistreplase, tissue plasminogen activator (tPA), and urokinase.

The invention also encompasses screening assays for identifying therapeutic GAG fragments for the treatment of a tumor and for preventing metastasis. The assays may be accomplished by treating a tumor or isolated tumor cells with modified chondroitinase B and/or other native or modified heparinases and isolating the resultant GAG fragments. The isolated GAG fragments may then be tested for therapeutic activity in the prevention of tumor cell proliferation and metastasis. Thus the invention encompasses individualized therapies, in which a tumor or portion of a tumor is isolated from a subject and used to prepare the therapeutic GAG fragments. These therapeutic fragments can be re-administered to the subject to protect the subject from further tumor cell proliferation or metastasis or from the initiation of metastasis if the tumor is not yet metastatic. Alternatively the fragments can be used in a different subject having the same type or tumor or a different type of tumor.

The compositions of the invention are useful for treating and preventing cancer cell proliferation and metastasis. Thus, according to another aspect of the invention, there is provided methods for treating subjects having or at risk of having cancer. The terms "treat" and "treating" tumor cell proliferation as used herein refer to inhibiting completely or partially the proliferation or metastasis of a cancer or tumor cell, as well as inhibiting any increase in the proliferation or metastasis of a cancer or tumor cell.

A "subject having a cancer" is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

A "subject at risk of having a cancer" as used herein is a subject who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with a modified chondroitinase B or degradation product thereof the subject may be able to kill the cancer cells as they develop.

Effective amounts of the modified chondroitinase B, or GAG fragments of the invention are administered to subjects in need of such treatment. Effective amounts are those amounts which will result in a desired improvement in the condition or symptoms of the condition, e.g., for cancer this is a reduction in cellular proliferation or metastasis. Such amounts can be determined with no more than routine experimentation. It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

In some aspects of the invention the effective amount of modified chondroitinase B or GAG fragment is that amount effective to prevent invasion of a tumor cell across a barrier. The invasion and metastasis of cancer is a complex process which involves changes in cell adhesion properties which allow a transformed cell to invade and migrate through the extracellular matrix (ECM) and acquire anchorage-independent growth properties. Liotta, L. A., et al., Cell 64:327–336 (1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The barrier for the tumor cells may be an artificial barrier in vitro or a natural barrier in vivo. In vitro barriers include but are not limited to extracellular matrix coated membranes, such as Matrigel. Thus the modified chondroitinase B compositions or degradation products thereof can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer (1992) 52:378–383. Matrigel is a reconstituted basement membrane containing type IV collagen, laminin, heparan sulfate proteoglycans such as perlecan, which bind to and localize bFGF, vitronectin as well as transforming growth factor-$\beta$ (TGF-$\beta$), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference. An in vivo barrier refers to a cellular barrier present in the body of a subject.

When administered to a patient undergoing cancer treatment, the modified chondroitinase B or GAG fragment may be administered in cocktails containing other anti-cancer agents. The compounds may also be administered in cocktails containing agents that treat the side-effects of radiation therapy, such as anti-emetics, radiation protectants, etc.

The modified chondroitinase B or GAG compounds may also be linked to a targeting molecule. A targeting molecule is any molecule or compound which is specific for a particular cell or tissue and which can be used to direct the modified chondroitinase B or GAG to the cell or tissue. Preferably the targeting molecule is a molecule which specifically interacts with a cancer cell or a tumor. For instance, the targeting molecule may be a protein or other type of molecule that recognizes and specifically interacts with a tumor antigen.

The preparations of the present invention may also be used to inhibit binding to CS/DS proteoglycans that act as cell adhesion molecules, particularly during infection (e.g. malarial infection). It has been found that in pregnant women infected with *Plasmodium falciparum* infected red blood cells (IRBCs) accumulate in the placenta. The accumulation of IRBCs is believed to be due to the adhesion of IRBC membrane proteins to molecules found in the intervillous space in the placenta such as chondroitin 4-sulfate (Achur et. al., 2000, The Journal of Biological Chemistry, Vol. 275, No. 51 and Alkhalil, et. al., 2000, The Journal of Biological Chemistry, Vol. 275, No. 51). One aspect of the present invention, therefore, is a method for inhibiting maternal malarial infection. An effective amount for treating malarial infection is that amount that leads to a decrease in the number of infected red blood cells in the placenta sufficient that eliminate or decrease the undesirable effects of malarial infection during pregnancy. These effects include: low birth weight, still birth, abortion, premature delivery and maternal morbidity and mortality (Achur et. al., 2000, The Journal of Biological Chemistry, Vol. 275, No. 51).

The modified chondroitinase B is, in some embodiments, immobilized on a support. The modified chondroitinase B may be immobilized to any type of support but if the support is to be used in vivo or ex vivo it is desired that the support is sterile and biocompatible. A biocompatible support is one which would not cause an immune or other type of damaging reaction when used in a subject. The modified chondroitinase B may be immobilized by any method known in the art. Many methods are known for immobilizing proteins to supports. A "solid support" as used herein refers to any solid material to which a polypeptide can be immobilized.

Solid supports, for example, include but are not limited to membranes, e.g., natural and modified celluloses such as nitrocellulose or nylon, Sepharose, Agarose, glass, polystyrene, polypropylene, polyethylene, dextran, amylases, polyacrylamides, polyvinylidene difluoride, other agaroses, and magnetite, including magnetic beads. The carrier can be totally insoluble or partially soluble and may have any possible structural configuration. Thus, the support may be spherical, as in a bead, or cylindrical, as in the inside surface of a test tube or microplate well, or the external surface of a rod. Alternatively, the surface may be flat such as a sheet, test strip, bottom surface of a microplate well, etc.

The modified chondroitinase B may also be used to remove active GAGs from a GAG containing fluid. A GAG containing fluid is contacted with the modified chondroitinase B of the invention to degrade the GAG. The method is particularly useful for the ex vivo removal of GAGs from blood. In one embodiment the modified chondroitinase B may be immobilized on a solid support as is conventional in the art. The solid support containing the immobilized modified chondroitinase B may be used in extracorporeal medical devices (e.g. hemodialyzer, pump-oxygenator) to prevent the blood in the device from clotting. The support membrane containing immobilized modified chondroitinase B is positioned at the end of the device to neutralize the GAG before the blood is returned to the body.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V). Suitable preservatives include benzalkonium chloride (0.003–0.03% W/V); chlorobutanol (0.3–0.9% W/V); parabens (0.01–0.25% W/V) and thimerosal (0.004–0.02% WN).

The present invention provides pharmaceutical compositions, for medical use, which comprise modified chondroitinase B and/or GAG fragments together with one or more pharmaceutically acceptable carriers and optionally other therapeutic ingredients. The term "pharmaceutically-acceptable carrier" as used herein, and described more fully below, means one or more compatible solid or liquid filler, dilutants or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being commingled with the modified chondroitinase B or GAG fragments, and with each other, in a manner such that there is no interaction which would substantially impair the desired pharmaceutical efficiency.

A variety of administration routes are available. The particular mode selected will depend, of course, upon the particular active agent selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. A preferred mode of administration is a parenteral route. The term "parenteral" includes subcutaneous injections, intravenous, intramuscular, intraperitoneal, intrasternal injection or infusion techniques. Other modes of administration include oral, mucosal, rectal, vaginal, sublingual, intranasal, intratracheal, inhalation, ocular, transdermal, etc.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527–1533, 1990, which is incorporated herein by reference.

The compositions may conveniently be presented in unit dosage form and may be prepared by any of the methods well known in the art of pharmacy.

Other delivery systems can include time-release, delayed release or sustained release delivery systems. Such systems can avoid repeated administrations of the compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; non-polymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

Controlled release of modified chondroitinase B or GAG fragments can also be achieved with appropriate excipient materials that are biocompatible and biodegradable. These polymeric materials which effect slow release of the modified chondroitinase B or GAG fragments may be any suitable polymeric material for generating particles, including, but not limited to, nonbioerodable/non-biodegradable and bioerodable/biodegradable polymers. Such polymers have been described in great detail in the prior art. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride polystyrene, polyvinylpryrrolidone, hyaluronic acid, and chondroitin sulfate.

Examples of preferred non-biodegradable polymers include ethylene vinyl acetate, poly(meth) acrylic acid, polyamides, copolymers and mixtures thereof.

Examples of preferred biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. The most preferred polymers are polyesters, polyanhydrides, polystyrenes and blends thereof.

A subject is any human or non-human vertebrate, e.g., dog, cat, horse, cow, pig.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods
Materials
Porcine intestinal mucosa dermatan sulfate, chondroitin 4-sulfate, and chondroitin 6-sulfate were purchased from Sigma (St. Louis, Mo.). The disaccharide standards were from Seikagaku/Associates of Cape Cod (Falmouth, Mass.). Oligonucleotide primers for PCR mutagenesis were from Invitrogen (Carlsbad, Calif.).

Docking of Dermatan Sulfate Tetrasaccharide into Chondroitinase B Active Site

The structure of the dermatan sulfate tetrasaccharide was obtained from a recently solved co-crystal structure of a chondroitinase AC mutant enzyme with a dermatan sulfate hexasaccharide (PDB id: IHM2). Only four of the sugar units in this hexasaccharide were defined in the co-crystal structure (Huang, W., Boju, L., Tkalec, L., Su, H., Yang, H. O., Gunay, N. S., Linhardt, R. J., Kim, Y. S., Matte, A., and Cygler, M. (2001) *Biochemistry* 40, 2359–72). Therefore, we used the defined tetrasaccharide region, $\Delta UA(1\rightarrow3)GalNAc4S(1\rightarrow4)IdoA(1\rightarrow3)GalNAc4S$, in our docking study. The initial orientation of this dermatan sulfate structure relative to chondroitinase B was obtained by superimposing the non-reducing end of the tetrasaccharide with the disaccharide in the co-crystal structure. This preliminary orientation was modified by manually manipulating the tetrasaccharide structure to optimize favorable contacts between the active site amino acids and the tetrasaccharide. All the manipulations of the structures and docking were done using the Viewer and Docking module of INSIGHTII.

The manually modified docked tetrasaccharide was subjected to a energy minimization process in which the potentials of the enzyme and the oligosaccharide were set using the AMBER force field modified to include carbohydrates (Homans, S. W. (1990) *Biochemistry* 29, 9110–8) with sulfate and sulfamate groups (Huige, C. J. M., and Altona, C. (1995) *J. Comp. Chem.* 16, 56–7926). The enzyme-substrate complex was subjected to 300 steps of steepest gradient minimization without including charges, keeping most of the enzyme fixed, and allowing only the regions close to the substrate to move. A force constant of 5,000 kcal was applied to each of the ring torsion angles ensuring that the ring geometries of the sugar units in the tetrasaccharide were not significantly distorted. Each of the subsequent orientations of the tetrasaccharide substrate was evaluated for steric contacts and non-bonded interactions with the active site of the enzyme. The optimal orientation with reasonably low steric hindrance was selected for further energy minimization. The refined structure was further subjected to 300 steps of conjugate gradient minimization including charges. A distance-dependent dielectric with a scaling factor of 4.0 and 1–4 nonbonded scaling factor of 0.5 were set while using AMBER force field as recommended by the software manual.

PCR Site-Directed Mutagenesis of Chondroitinase B

Lys250, Arg271, His272, Glu333, Arg363, and Arg364 were mutated to alanine using overlap extension PCR for 15 cycles (Pojasek, K., Shriver, Z., Hu, Y., and Sasisekharan, R. (2000) *Biochemistry* 39, 4012–9). The primer sequences used for each of the mutants are as follows:

```
H272A 5':
AAC TTT CGT GCC GGT GAT CAT (SEQ ID NO: 3)

H272A 3':
ATG ATC ACC GGC ACG AAA GTT (SEQ ID NO: 4)

E333A 5':
ATG GCT TCG GCG CAT GCT CTT (SEQ ID NO: 5)

E333A 3':
AAG AGC ATG CGC CGA AGC CAT (SEQ ID NO: 6)

K250A 5':
ATC ACC AGC GCG TCG CAG GAA (SEQ ID NO: 7)

K250A 3':
TTC CTG CGA AGC GCT GGT GAT (SEQ ID NO: 8)

R271A 5':
ATG AAC TTT GCT CAC GGT GAT (SEQ ID NO: 9)

R271A 3':
ATC ACC GTG AGC AAA GTT CAT (SEQ ID NO: 10)

R363A 5':
TTG GAT GAG GCC AGA AAA GAA (SEQ ID NO: 11)

R363A 3':
TTC TTT TCT GGC CTC ATC CAA (SEQ ID NO: 12)

R364A 5':
GAT GAG CGC GCA AAA GAA TAT (SEQ ID NO: 13)

R364A 3':
ATA TTC TTT TGC GCG CTC ATC (SEQ ID NO: 14)
```

The PCR reaction products were separated on an agarose gel and the band corresponding to the proper length was excised. The DNA was extracted from the gel using a Gel Purification Kit (Qiagen, Valencia, Calif.), the insert was subcloned into pCRT7/NT (Invitrogen, Carlsbad, Calif.), and the plasmid was prepared using a Miniprep kit (Qiagen). Each of the clones was sequenced to verify the presence of the individual alanine point mutations. Each chondroitinase B mutant was excised from pCRT7/NT using Nde I and BamH I (New England Biolabs, Beverly, Mass.) enzyme cocktail and subcloned into a pET15b expression vector (Novagen, Madison, Wis.) that had been digested previously with these same enzymes. Recombinant chondroitinase B that had been cloned in a similar fashion was also expressed and compared to each of the alanine mutants.

Protein Expression and Purification

Recombinant chondroitinase B and the site-directed mutants were expressed and purified as previously described (Pojasek, K., Shriver, Z., Kiley, P., Venkataraman, G., and Sasisekharan, R. (2001) *Biochem. Biophys. Res. Commun.* 286, 343–51). Purity of recombinant chondroitinase B and the site-directed mutants were assessed by SDS-polyacrylamide gel electrophoresis analysis using precast 12% gels, the Mini-Protean II apparatus, and the Silver Stain Plus kit (Bio-Rad, Hercules, Calif.). A relative protein concentration was calculated using the Bradford Assay (Bio-Rad, Hercules, Calif.) with bovine serum albumin as a standard.

Kinetic Analysis

The activity of chondroitinase B and the various site-directed mutants was determined by adding 10–50 µl of the sample to a 1 ml cuvette containing 1 mg/ml of dermatan sulfate in 50 mM Tris-HCl, pH 8.0 at 30° C. Product formation was monitored as an increase in absorbance at 232 nm as a function of time (Pojasek, K., Shriver, Z., Kiley, P., Venkataraman, G., and Sasisekharan, R. (2001) *Biochem. Biophys. Res. Commun.* 286, 343–51).

The kinetic parameters, $K_m$ and $k_{cat}$, were calculated for chondroitinase B and the site-directed mutants by obtaining the initial reaction rate ($v_o$) as a function of substrate concentration. Approximately 1 µg (13 pmol) of enzyme was added to a 1 ml of dermatan sulfate at concentrations ranging from 0.010 µg/ml to 2 mg/ml. The initial rate was measured for 4–10s at 30° C. in the same Tris-HCl buffer used for the activity assay. The slope of the resulting line, assuming zero order kinetics, was plotted versus the substrate concentration using SigmaPlot (SSPS, Inc., Chicago, Ill.). The $K_m$ (µM) and $V_{max}$ (µM/s) were calculated using the Michaelis-Menten equation: $v_0=(V_{max}*[S])/(K_m+[S])$. The $k_{cat}$ (s$^{-1}$) was calculated by dividing the $V_{max}$ by the concentration of enzyme in the reaction.

Dermatan Sulfate Digestion and Capillary Electrophoresis

To examine changes in product profile of each site-directed mutant when compared to recombinant chondroitinase B (20 μg), digests of 1 mg/ml dermatan sulfate 50 mM Tris-HCl, pH 8.0 were performed for 12–14 hr. at 30° C. The digests were analyzed using capillary electrophoresis as previously described (Pojasek, K., Shriver, Z., Kiley, P., Venkataraman, G., and Sasisekharan, R. (2001) *Biochem. Biophys. Res. Commun.* 286, 343–51). Briefly, the chondroitinase B and site-directed mutant digests were diluted twofold and analyzed with an extended path-length cell and a voltage of 30 kV applied using reverse polarity. The running buffer consisted of 50 mM Tris, 10 μM dextran sulfate that had been brought to a pH of 2.5 using phosphoric acid and the saccharide products were detected by monitoring at 232 nm.

The total peak area for the recombinant chondroitinase B and mutant digest profiles was calculated by totaling the areas of the ΔUA-GalNAc2S,4S; ΔUA-GalNAc4S,6S; and ΔUA-GalNAc4S peaks. The total peak area for the R364A mutant also included the sum of the area of the three additional oligosaccharide peaks. The ratio of the ΔUA-GalNAc4S peak area to the total peak area was then calculated for the recombinant chondroitinase B and each mutant for a comparison of overall enzymatic activity.

MALDI Mass Spectrometry

The reaction products from the R364A digest of dermatan sulfate were analyzed using MALDI-MS. Samples were prepared using the basic peptide $(RG)_{15}R$ as previously described (Rhomberg, A. J., Ernst, S., Sasisekharan, R., and Biemann, K. (1998) *Proc. Natl. Acad. Sci. USA* 95, 4176–81). MALDI-MS spectra were acquired on a Voyager Elite system (PerSeptive Biosystems, Framingham, Mass.) in the linear mode with delayed extraction and similar instrument parameters to those described previously (Rhomberg, A. J., Ernst, S., Sasisekharan, R., and Biemann, K. (1998) *Proc. Natl. Acad. Sci. USA* 95, 4176–81).

Circular Dichroism

Recombinantly expressed chondroitinase B and the inactive K250A mutant were concentrated and buffer-exchanged into 50 mM sodium phosphate, pH 7.0 using a Centricon 10 Filter (Millipore, Watertown, Mass.). CD spectra were collected on an Aviv 62DS spectropolarimeter equipped with a thermostatic temperature controller and interfaced to an IBM microcomputer. Measurements were performed in a quartz cell with a 1 mm path length. Spectra were recorded at 25° C., in an average of 10 scans between 205 and 270 nm, with a 1.0 nm bandwidth and a scan rate of 3 nm/min. CD band intensities are expressed as molar ellipticities, $\theta_M$, in degrees·cm$^2$·dmol$^{-1}$.

Results and Discussion

Interactions between Chondroitinase B and Dermatan Sulfate substrate

The structure of a previously crystallized DS tetrasaccharide was docked into the chondroitinase B active site. The direction of the tetrasaccharide relative to the enzyme was the same as the ΔUA-GalNAc4S disaccharide product in the co-crystal structure with the non-reducing end of the tetrasaccharide towards the C-terminus and the reducing end towards the N-terminus of the enzyme. However, the orientation of the tetrasaccharide relative to the parallel beta-helical axis of the enzyme was different from that of the disaccharide (FIG. 1, (A)). When the non-reducing end of the tetrasaccharide was superimposed with the disaccharide product from the co-crystal structure, the orientation of the tetrasaccharide was such that its reducing end collided with a wall of the active site cleft (FIG. 1, (A)). Also, in this orientation, its reducing end was too far apart from the basic cluster of residues His116, Arg184, and Arg218. Our docking energy minimization resulted in repositioning of the tetrasaccharide substrate to achieve maximum contact with the active site cleft of the enzyme (FIG. 1, (A)). In the final orientation, the tetrasaccharide completely occupied the −2, −1, +1, and +2 subsites (standard nomenclature) of the active site of chondroitinase B.

Active Site Residues

The docked tetrasaccharide occupied all of the chondroitinase subsites, and the theoretical enzyme-substrate complex provided a better picture of the interaction between the DS substrate and the active site residues. Glu333, Lys250, Arg271 and His 272 were identified as key residues involved in catalysis based on the proximity to the −1 and +1 subsites containing cleavable —GalNAc4S-IdoA-linkage (FIG. 1, (B)). This cluster of charged residues in the catalytic site suggests that there may be more than the prototypical triad of residues that are involved in the proton abstraction and donation mechanism resulting in the β-eliminative cleavage. Glu333 is positioned proximal to the O1 of GalNAc4S in such a way that it could potentially mediate proton abstraction via a water molecule. The proximity of His272 and Lys250 to the C5 proton (FIG. 1, (B)) indicates that these residues are also positioned to act as general base for proton abstraction. However, Lys250 is the only residue in proximity to the carboxylate moiety of the IdoA monosaccharide and supports its involvement in neutralizing the charge of the carboxylate group. Arg271 is proximal to both the ring oxygen and O1 of GalNAc residue and thus is positioned to protonate the leaving O1 atom of the GalNAc after cleavage.

Substrate Binding Residues

Several residues involved in substrate binding were identified from our theoretical chondroitinase B-tetrasaccharide complex. These include basic residues Arg318, Arg363 and Arg364 and pyranose ring stacking aromatic residues Phe296 and Trp298. Phe296 provides a parallel stacking interaction with the IdoA in the −2 subsite and Trp298 stacks perpendicularly with the IdoA and GalNAc in subsite −2 and −1, respectively (FIG. 1, (B)). Arg364 is positioned to interact with both the 4-O sulfate of the GalNAc4S and the carboxyl group of the non-reducing end IdoA (FIG. 1, (B)). Since the 4-O sulfate group of GalNAc4S and IdoA are hallmark modifications of dermatan sulfate, Arg364 residue is most likely to be involved in substrate specificity of the enzyme. Arg318 interacts with the IdoA in the −2 site and Arg363 is positioned to interact with an additional GalNAc4S moiety on the nonreducing end in what would potentially be subsite −3. Finally, Asn213 interacts with the N-acetyl group of the GalNAc in the −1 subsite (FIG. 1, (B)).

Figure 1B:
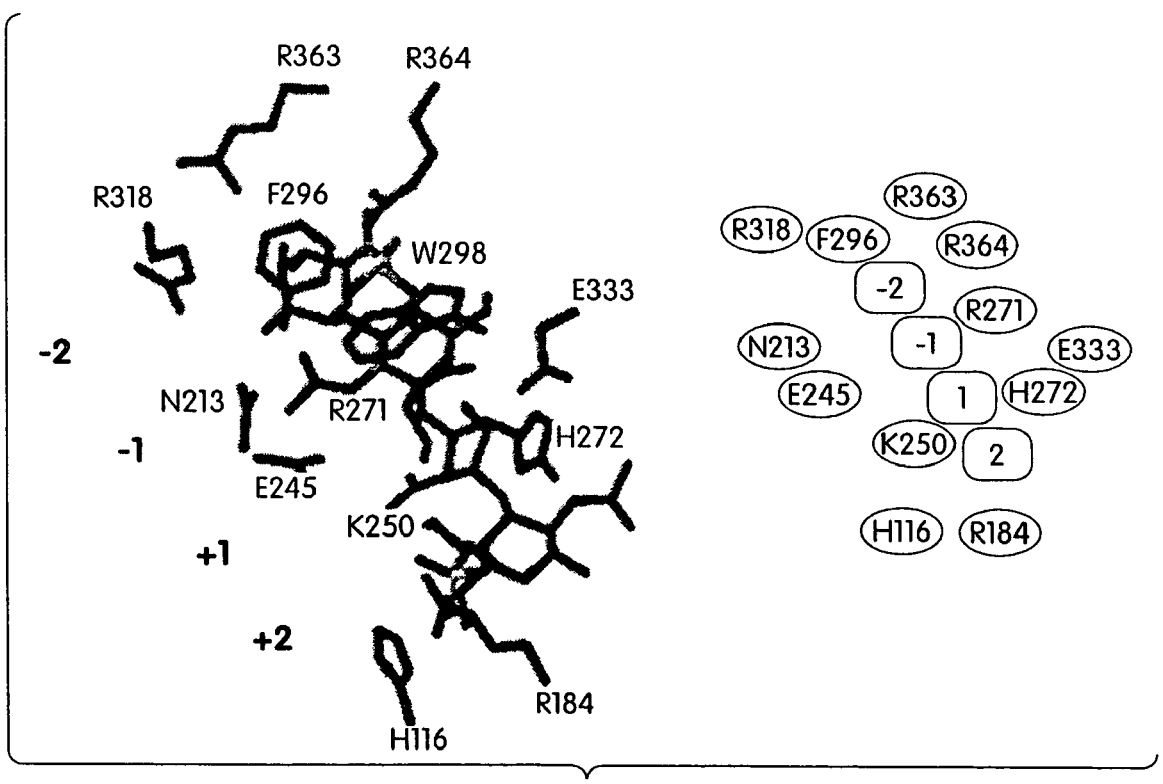

In the product release site (subsites +1 and +2), the side chains of Arg184 and His116 are oriented to provide favorable ionic interactions with the GalNAc4S residue at the reducing end of the DS tetrasaccharide (FIG. 1, (B)). These interactions provide a more definitive meaning to the speculated role of these two basic residues in binding to 4-O sulfate group at the reducing end of the DS substrate. Taken together, our enzyme-substrate complex provides a clear framework of the various residues involved in substrate binding and product release.

Active Site Symmetry

Figure 2:
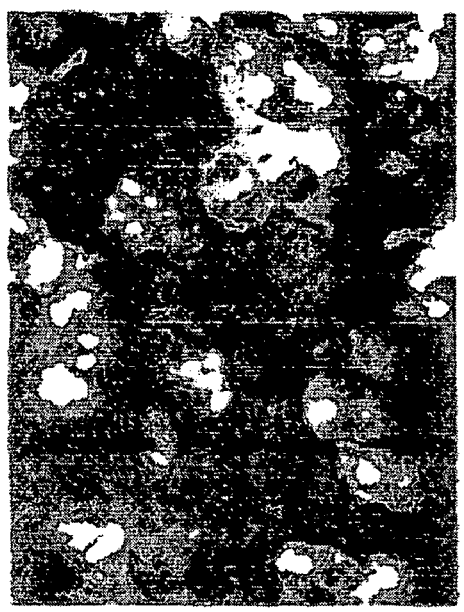
FIG. 2 details the apparent internal symmetry in the active site of chondroitinase B. The grasp rendered view of the active site is shown on the left with the basic residues (H, K, R) colored in blue, acidic residues (D, E) colored in red, and bulky hydrophobic residue (F, Y, W) colored in pink. On the right is a two dimensional schematic of the residues with their sequence numbers encircled using the same color coding scheme as on the left. Also shown on the right is an arrow colored (gray) indicating the assumed direction of the dermatan sulfate in this study (point of arrow indicates the reducing end). There is an approximate two-fold symmetry in the distribution of the acidic, basic and, hydrophobic residues about an axis perpendicular to the helix of the dermatan sulfate oligosaccharide.
Figure 2:
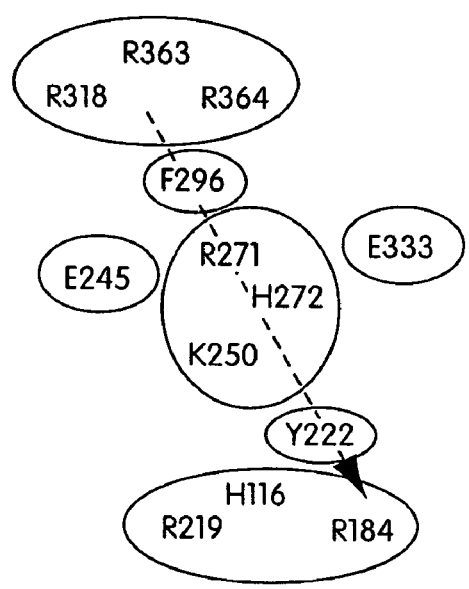
Figure 3A:
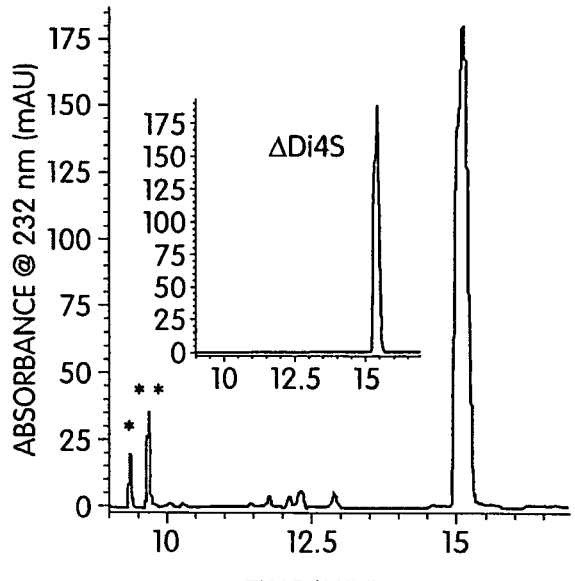
FIG. 3 summarizes the capillary electrophoretic analysis of the dermatan sulfate reaction products for the catalytic mutations. (A) Recombinant chondroitinase B (20 µg), (B) H272A, (C) E333A, and (D) K250A were incubated with the 1 mg/ml dermatan sulfate for 12 hr at 30° C. Capillary electrophoretic analysis was performed using an extended path-length cell and a voltage of 30 kV applied using reverse polarity. Saccharides were injected into the capillary using hydrodynamic pressure and were detected using an ultraviolet detector set at 232 nm. The running buffer consisted of 50 mM Tris, 10 µM dextran sulfate that had been brought to a pH of 2.5 using phosphoric acid. The disulfated disaccharides, ΔUA-GalNAc2S4S and ΔUA-GalNAc4S,6S, are indicated by "*" and "**", respectively. (inset) Electropherogram of the ΔUA-GalNAc4S disaccharide standard.
Figure 3B:
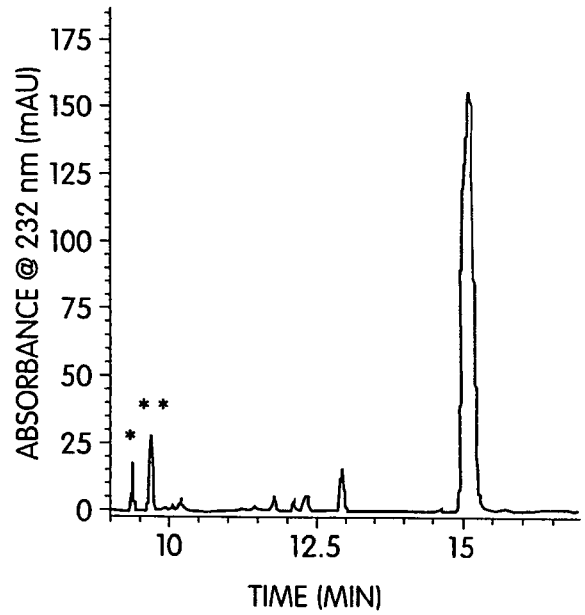
Figure 3C:
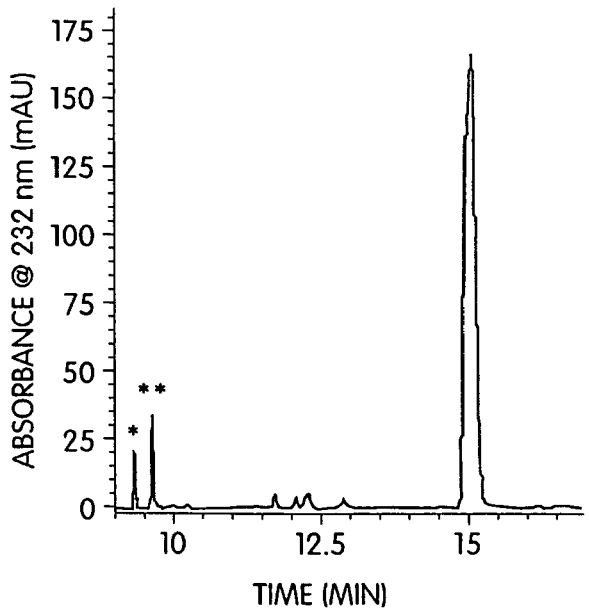
Figure 3D:
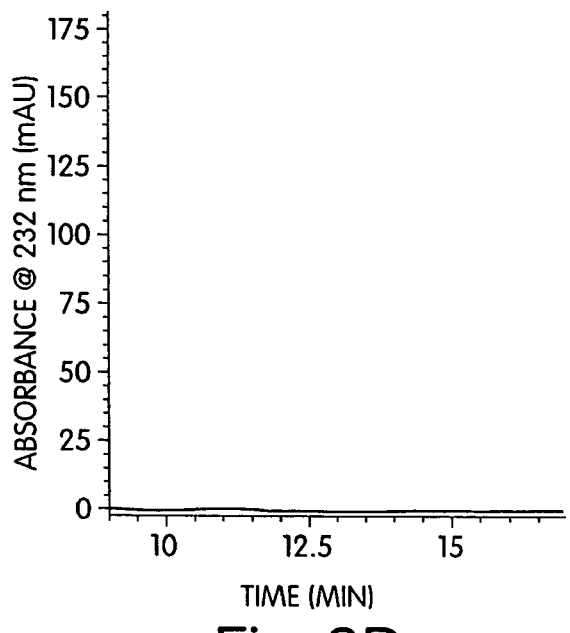

In addition to providing further insight into the exact role of each residue in the chondroitinase B active site, our conformational study also uncovered a chemical symmetry of amino acid side chains in this region. In fact, there appears to be an internal twofold symmetry of the positively charged, negatively charged, and hydrophobic residues in the active site about an axis passing through the cleavage site (−1 and +1) and perpendicular to the axis of the β helix (FIG. 2). Specifically the proposed residues that are involved in the substrate binding site (−2 and −1), including Phe296, Arg318, Arg364, seem to have corresponding residues in the product release site (+1 and +2), including Tyr222, Arg184 and Arg219 that are related by this symmetry. In addition, Glu245 is in proximity of the catalytic site and appears to be related to the Glu333 residue by the same twofold symmetry (FIG. 2).

Understanding the significance of the active site symmetry provides valuable insights into the mechanism by which chondroitinase B depolymerizes its DS substrate. Without being bound by any particular theory, several plausible explanations regarding the importance of this active site symmetry are proposed. To begin with, the distance between the carbonyl oxygens of both Glu245 and Glu333 is about 9.5 Å, a distance comparable to the diameter of the structure of the DS substrate projected along the helical axis. Thus, if both of these negatively charged glutamates are involved in catalysis, their symmetrical arrangement would facilitate the translation of the substrate through the active site cleft without the need for its rotation, leading to more efficient DS depolymerization. In addition, this active site symmetry may be involved in accommodating the perturbations in the DS chain caused by the conformational flexibility of iduronic acid, a common component of dermatan sulfate (Venkataraman, G., Sasisekharan, V., Cooney, C. L., Langer, R., and Sasisekharan, R. (1994) *Proc. Natl. Acad. Sci. USA* 91, 6171–5).

The symmetry of the active site may also be involved in defining the direction that the substrate is processed through the active site. Interestingly, the DS-derived disaccharide in the co-crystal structure that is an actual product of chondroitinase B action is in the substrate binding site, not the product release site. This observation, coupled with the active site symmetry, suggests that the directionality of the active site might be more complex than originally thought. In fact, the reducing end of a genuine substrate may be potentially oriented towards the C-terminal end of enzyme, a pattern of binding common among other polysaccharide lyases (Steinbacher, S., Seckler, R., Miller, S., Steipe, B., Huber, R., and Reinemer, P. (1994) *Science* 265, 383–6 and Scavetta, R. D., Herron, S. R., Hotchkiss, A. T., Kita, N., Keen, N. T., Benen, J. A., Kester, H. C., Visser, J., and Jumak, F. (1999) *Plant Cell* 11, 1081–92), and not towards the N-terminal end as seen in the co-crystal structure (Huang, W., Matte, A., Li, Y., Kim, Y. S., Linhardt, R. J., Su, H., and Cygler, M. (1999) *J. Mol. Biol.* 294, 1257–69). The directionality of substrate binding within the active site of polysaccharide lyases is usually unambiguously defined by a structural feature similar to the presence of a $Ca^{2+}$ ion at one end of the cleft as is the case with pectate lyase C from *Erwinia chrysanthemi* (Scavetta, R. D., Herron, S. R., Hotchkiss, A. T., Kita, N., Keen, N. T., Benen, J. A., Kester, H. C., Visser, J., and Jumak, F. (1999) *Plant Cell* 11, 1081–92). This underscores the uniqueness of the chondroitinase B active site symmetry.

Mutagenesis and Active Site Characterization

Having identified the key substrate binding and catalytic residues using our theoretical enzyme-substrate complex, we sought to establish their functional roles using site-directed mutagenesis. The basic residues, Lys250, Arg271, and His272, were chosen based on their location in the active site of chondroitinase B. In addition, the acidic residue, Glu333 was chosen because of its possible role in proton abstraction. We also mutated two of the residues implicated in substrate binding and specificity, namely Arg363 and Arg364 to alanine. These site-directed mutants were cloned into pET15b and expressed along side the recombinant chondroitinase B.

Both H272A and E333A showed altered kinetics when compared with the recombinant chondroitinase B (Table 1). For instance, the $K_m$ and $k_{cat}$ for the H272A chondroitinase B mutant are 2.7 μM and 29 $s^{-1}$, respectively, compared to a $K_m$ of 4.6 μM and a $k_{cat}$ of 190 $s^{-1}$ for the recombinant enzyme (Pojasek, K. et al. (2001) *Biochem. Biophys. Res. Commun.* 286, 343–51). The E333A mutant had similar alterations in $K_m$ and $k_{cat}$ (Table 1). Both of these mutations lead to a slight reduction in $K_m$ while drastically reducing $k_{cat}$. In fact, when compared to the recombinant chondroitinase B, the H272A and the E333A mutants have a fourfold and a 26-fold decrease in $k_{cat}/K_m$, respectively (Table 1).

TABLE 1

Kinetic Analysis of Chondroitinase B and Mutants

| Enzyme | Kinetic Parameters[a] | | |
|---|---|---|---|
|  | $K_m$ (μM) | $K_{cat}$ ($s^{-1}$) | $k_{cat}/K_m$ (μM $s^{-1}$) |
| Chondroitinase B | 4.6 ± 0.31 | 190 ± 80 | 41 |
| K250A | n.d.[b] | n.d.[b] | n.d.[b] |
| H272A | 2.7 ± 0.24 | 29 ± 3.0 | 11 |
| E333A | 2.8 ± 0.64 | 4.6 ± 1.6 | 1.6 |
| R363A | 4.6 ± 0.49 | 404 ± 156 | 88 |
| R364A | n.d.[b] | n.d.[b] | n.d.[b] |

[a]Values are the mean of 3 experiments ± S.E.
[b]Kinetics were undetectable due to low activity of the mutant enzyme.

In addition to kinetic analysis, each of the mutant enzymes and the recombinant chondroitinase B were allowed to exhaustively digest dermatan sulfate to determine changes in product profile that may belie alterations in substrate specificity. These digests were diluted and analyzed using capillary electrophoresis. Complete digestion of the dermatan substrate was seen with the chondroitinase B reaction as indicated by a major disaccharide peak (FIG. 3). This prominent disaccharide peak in all of the electropherograms was identified as ΔUA-GalNAc4S through co-migration of the known dermatan sulfate disaccharide standards. The two minor peaks that elute around 10 min were identified as ΔUA-GalNAc2S,4S (*) and ΔUA-GalNAc4S,6S (**), respectively (FIG. 3). A comparison between the ratio of the ΔUA-GalNAc4S peak to the total peak area of the mutant digests and the recombinant enzyme showed that H272A and

TABLE 2

Ratio of ΔDi4S Area to Total Peak Area for Chondroitinase B and Mutants

| Enzyme | ΔDi4S: Total Peak Area |
|---|---|
| Chondroitinase B | 0.93 |
| K250A | n.d.[a] |
| H272A | 0.94 |

TABLE 2-continued

Ratio of ΔDi4S Area to Total Peak Area for Chondroitinase B and Mutants

| Enzyme | ΔDi4S: Total Peak Area |
|---|---|
| E333A | 0.93 |
| R363A | 0.93 |
| R364A | 0.39 |

[a]No peaks were observed for the K250A digest.

E333A demonstrate full enzymatic activity over the 12 hr time course of the reaction (Table 2). This suggests that, while His272 and Glu333 are important in the active site chemistry, chondroitinase B can still function without one of them, albeit at a slower catalytic rate.

Figure 5:
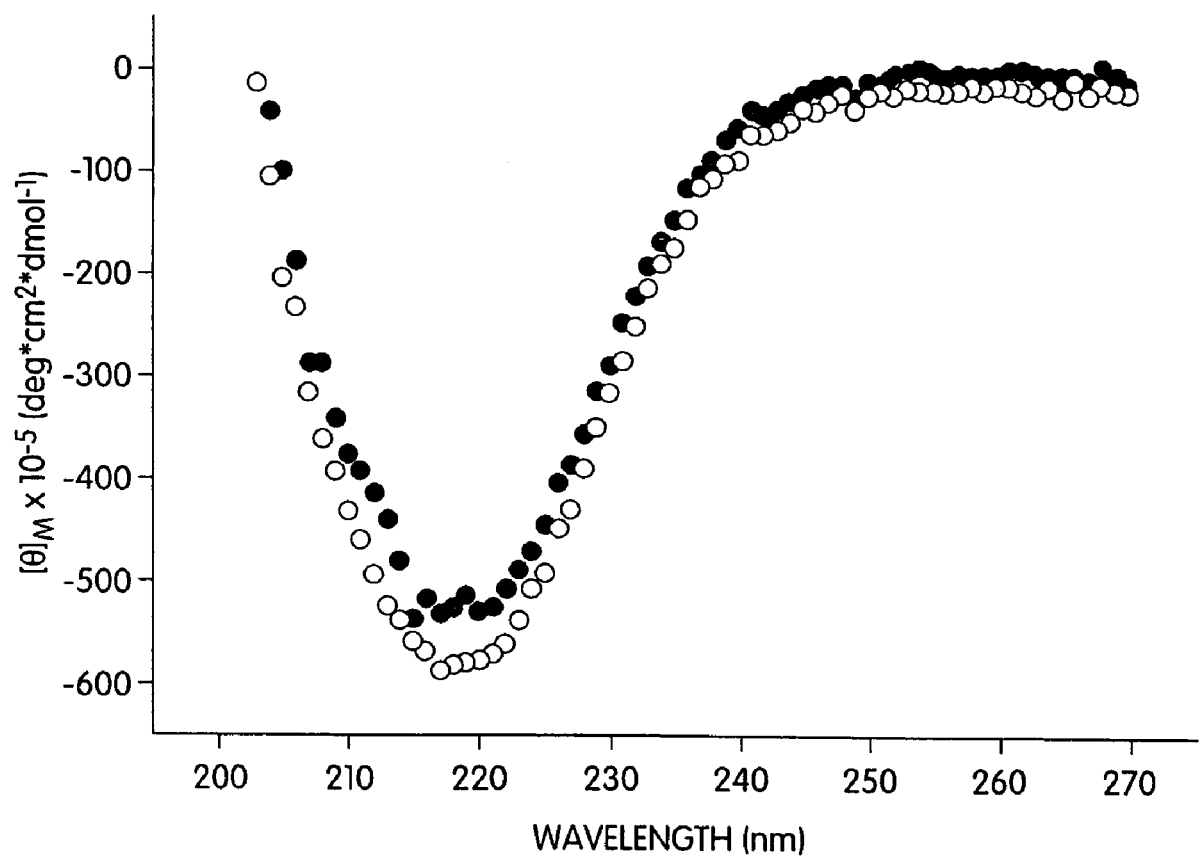
FIG. 5 provides the CD spectra of chondroitinase B and the K250A mutant The recombinant chondroitinase B (●) and the K250A mutant (○) were concentrated and buffer exchanged into 50 mM sodium phosphate buffer, pH 7.0. Proteins were analyzed in a quartz cell with 1 mm path length at 25° C. CD Spectra were recorded between 200 and 270 nm with an average of 5 scans; the bandwidth was set 1.0 nm; and the scan rate was 3 nm/min. The CD band intensities are expressed as molar ellipticities, $\theta_M$, in deg·cm$^2$·dmol$^{-1}$.

In contrast, changing Lys250 to alanine completely ablated the activity of chondroitinase B (Table 1 and FIG. 3). To insure that the mutating Lys250 did not influence the overall stability of the protein, the CD spectrum of K250A was compared to the spectrum of recombinant chondroitinase B. While the virtual identity of the CD profiles does not preclude the possibility that there are perturbations in the local environment surrounding Lys250 that are not represented in the CD profile, it does suggest there are no gross conformational changes induced in chondroitinase B by mutating Lys250 to alanine (FIG. 5). Therefore, Lys250 plays a role in the catalytic activity of chondroitinase B.

Along with the active site residues discussed above, we mutated Arg271 to alanine. Interestingly, the R271A mutant was expressed at comparable levels to the recombinant chondroitinase B, but was insoluble. Several attempts to denature and refold the mutant using different methods including a strong chaotropic agent (4M guanidinium HCl) proved unsuccessful. The insolubility of the R271A mutant could implicate this residue in the active site chemistry of chondroitinase B. Another possibility is that removing the side chain of Arg271 somehow interferes with the hydrophobic stacking interactions of Phe296 and Trp298 leading to a dramatic decrease in the stability of chondroitinase B (FIG. 1, (B)). In addition to catalytic residues discussed above, two basic residues proximal to subsites −2 and −1, Arg363 and Arg364, were selected for mutagenesis based on their potential role in substrate binding. The R363A mutant had a $k_{cat}$ of 404 s$^{-1}$, leading to a slight increase in $k_{cat}/K_m$ when compared to the recombinant chondroitinase B (Table 1). This twofold increase in $k_{cat}/K_m$ suggests that removal of Arg363 allows for a slight increase in catalytic efficiency in chondroitinase B. The R363A mutant produced a similar profile to chondroitinase B after exhaustive digestion of dermatan sulfate (FIG. 4).

Figure 4A:
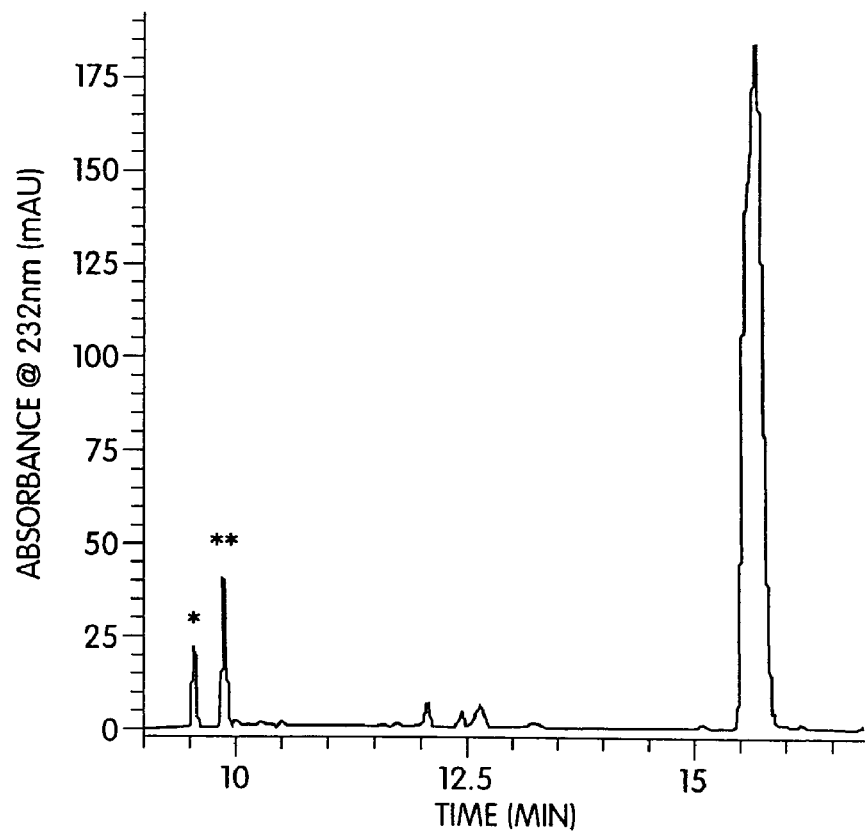
FIG. 4 summarizes the capillary electrophoretic analysis of the reaction products for the substrate binding mutations. (A) R363A and (B) R364A were incubated with 1 mg/ml dermatan sulfate for 12 hr at 30° C. and analyzed using capillary electrophoresis. The length and sulfate composition of the additional peaks in the R364A digest (B) were determined using MALDI-MS. Peak 1 is an octasaccharide (1922.4 Da) with 5 sulfates. Peak 2 is a hexasaccharide (1539.7 Da) with 5 sulfates. And Peak 3 is a tetrasaccharide (999.2 Da) with 3 sulfates. The disulfated disaccharides, ΔUA-GalNAc2S,4S and ΔUA-GalNAc4S,6S, are indicated by "*" and "**" respectively.
Figure 4B:
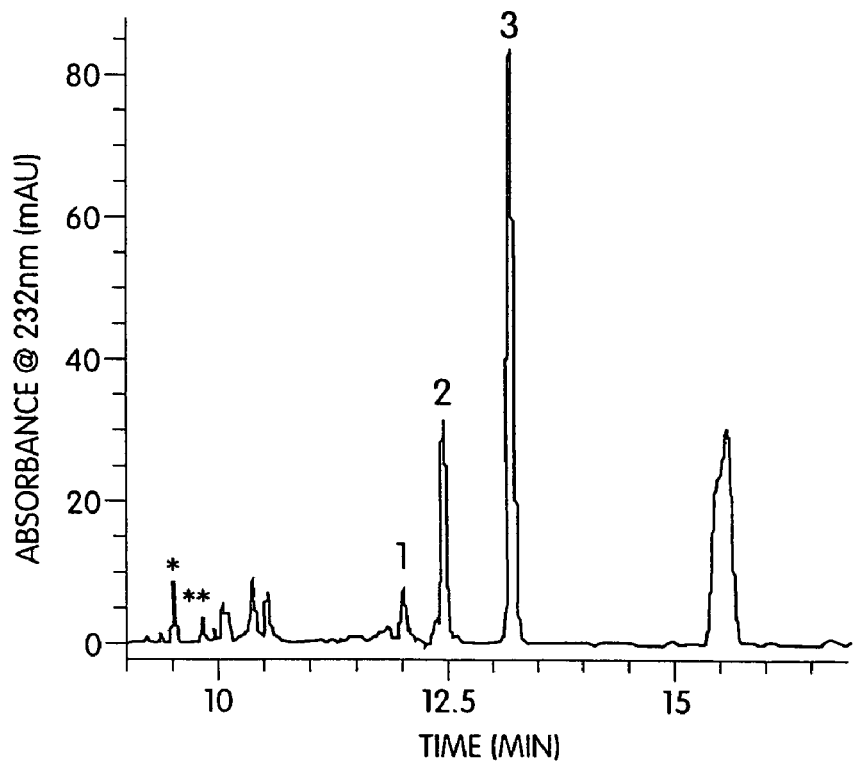

In contrast to the R363A results, mutating Arg364 to alanine led to a complete loss of activity in the real-time kinetic assay and an altered product profile after exhaustive digestion of dermatan sulfate (Table 1 and FIG. 4). In fact, the ratio of the ΔUA-GalNAc4S peak area to the total peak area was only 0.39, significantly lower the ratio for the recombinant chondroitinase B (Table 2). In addition, the ΔUA-GalNAc4S peak was not the only prominent peak in the electropherogram (FIG. 4).

To further characterize the novel peaks seen the R364A digest of dermatan sulfate, the sample was analyzed using MALDI-MS. Peak 3 had a mass of 999.2 Da, which identifies it as a tetrasaccharide containing 3 sulfates. Peak 2 had a mass of 1539.7 Da, which identifies it as hexasaccharide containing 5 sulfates. Finally, peak I had a mass of 1922.4 Da, which classifies it as an octasaccharide also containing 5 sulfates. Adding more of the R364A mutant enzyme to the sample did not result in a significant decrease of these higher order peaks, suggesting that these oligosaccharides are the end products of the reaction. As suggested by our structural analysis, Arg364 plays a role in the proper substrate binding and digestion of dermatan sulfate by chondroitinase B.

Compositional analysis of the DS starting material revealed that the ΔUA-GalNAc2S,4S and ΔUA-GalNAc4S, 6S disaccharides are 2.3% and 4.6% of the total disaccharide content. Interestingly, there is a shift in the percentages to 5.5% and 2.3% for the ΔUA-GalNAc2S,4S and ΔUA-GalNAc4S,6S disaccharides, respectively, when DS was digested by the R364A mutant suggesting that the oversulfation of the higher order oligosaccharides is at the 6-O position. Therefore, it appears that Arg364 is involved in chondroitinase B's ability to recognize and cleave regions containing ΔUA-GalNAc4S,6S in dermatan sulfate.

Taken together, these results, for the first time, directly implicate Lys250, His272, Glu333, and Arg271 in the catalytic degradation of dermatan sulfate by chondroitinase B. Since the H272A mutation shows a 6.5 fold decrease in $k_{cat}$, this residue can be potentially involved in the proton abstraction (Table 1). Histidine has been implicated in the enzymatic degradation of other GAG degrading enzymes including Group B Streptococcal hyaluronate lyase and heparinases I, II, and, III (Pojasek, K., Shriver, Z., Hu, Y., and Sasisekharan, R. (2000) *Biochemistry* 39, 4012–9; Lin, B., Averett, W. F., and Pritchard, D. G. (1997) *Biochem. Biophys. Res. Commun.* 231, 379–82; and Shriver, Z., Hu, Y., and Sasisekharan, R. (1998) *J. Biol. Chem.* 273, 10160–7). However, since the enzyme activity is not completely ablated another residue may also be involved in the abstraction of the C5 proton. Glu333, another candidate for C5 proton abstraction, showed a nearly 40-fold decrease in $k_{cat}/K_m$ when mutated to alanine (Table 1). Nevertheless, since the enzyme still retained close to full activity over a 12 hr period (FIG. 3), Glu333 also may not be the sole residue involved in the C5 proton abstraction. One possibility is that Glu333 and His272 work in concert with one another to both lower the pKa of the C5 proton and to abstract it. Another possibility is that Glu245, the symmetrical active site residue to Glu333, may also play a part in the proton abstraction (FIG. 1, (B)).

Mutating Lys250 to alanine led to a complete loss of enzymatic activity of chondroitinase B towards the dermatan sulfate substrate. Since the ε-NH$_2$ of the lysine (pKa of 10.5) is mostly protonated in the reaction buffer (pH 8.0), it seems unlikely that this residue would be involved in proton abstraction. Also, our conformational study points to the involvement of Lys250 in stabilizing the charge of the carboxylate moiety. Therefore, the loss of enzymatic activity in the K250A mutant is most likely due to this lack of stabilization of the carboxylate group (and the carbanion intermediate) effectively preventing abstraction of the C5 proton.

Materials and Methods

Materials

Dermatan sulfate from porcine intestinal mucosa, glucuronic acid, and galacturonic acid were purchased from Sigma. Caffeic acid and sodium tetraborate were purchased from Fluka. Chondroitinase ABC was purchased from Seikagaku/Associates of Cape Cod (Falmouth, Mass.). Chondroitinase B and the R364A mutant were recombinantly expressed in *E. coli* and purified as described previously (Pojasek, K., Raman, R., Kiley, P., Venkataraman, G., and Sasisekharan, R. (2002) J Biol Chem 277, 31179–86; Pojasek, K., Shriver, Z., Kiley, P., Venkataraman, G., and Sasisekharan, R. (2001) Biochem Biophys Res Commun 286, 343–51). Protein concentrations were calculated using the Bradford assay (Bio-Rad) with bovine serum albumin as a standard. All other reagents used are from common sources or are as noted.

Isolation of Defined DS Oligosaccharides

Dermatan sulfate was suspended in 50 mM Tris-HCl, pH 8.0 at a concentration of 10 mg/ml. To complete the partial digestion of the DS, 150 µg of the R364A recombinant chondroitinase B mutant was added to 10 ml of the DS solution. The reaction was incubated at 30° C. for 16 hr. The amount of R364A added to the reaction mixture was optimized using CE to ensure a maximal range of partially digested DS reaction products. Upon completion of the reaction, the DS products were separated on a 2.5×120 cm Bio-gel P6 column (Bio-Rad) with 500 mM ammonium bicarbonate as the mobile phase. Fractions with an absorbance at 232 nm, the $\lambda_{max}$ for the $\Delta^{4,5}$ double bond formed in the DS product by chondroitinase B, were pooled corresponding to the peaks containing various length DS oligosaccharides and lyophilized to dryness. The oligosaccharide pools were re-suspended in water and further fractionated by HPLC using a 4.6×250 mm Sphereclone 5 µm amine column (Phenomonex, Torrance, Calif.) with a gradient of 0.1 M to 1.0 M sodium phosphate, pH 4.5 over 30 min. Peaks were collected and desalted on a 2.5×55 cm Bio-gel P2 column (Bio-Rad) with a mobile phase of 500 mM ammonium bicarbonate. Fractions with absorbance at 232 nm were pooled, lyophilized to dryness, and re-suspended in water.

Semicarbazide Derivitization

The reducing end of the DS oligosaccharides was specifically derivatized with semicarbazide to provide a mass tag for MALDI-MS and to produce an altered migration time in the CE. Oligosaccharide solutions were mixed 1:1 (v/v) with 50 mM semicarbazide in 60 mM Tris/acetic acid, pH 7.0 (Rhomberg, A. J., Shriver, Z., Biemann, K., and Sasisekharan, R. (1998) Proc Natl Acad Sci USA 95, 12232–7). Reactions were heated at 40° C. for 16 hr and then analyzed using CE. The percent completion of each reaction was calculated using the ratio of the peak areas for the product and the unlabeled substrate in the CE.

Enzymatic Digests

Enzymatic digests were completed by adding 1 µl of varying dilutions of chondroitinase B (10–100 nM) or R364A (370 nM) to 15 µl reaction. Reactions were performed in 50 mM Tris-HCl, pH 8.0 with substrate concentrations ranging from 100–200 µM. The reactions were incubated at 30° C. for defined periods of time and heat inactivated at 85° C. for 5 min. The reaction products and substrate were analyzed using CE and MALDI-MS as described below without any further sample preparation.

Uronic Acid Plate Assay

A 96 well plate assay was used for determining the relative amount of uronic acid in a DS oligosaccharide sample (van den Hoogen, B. M., van Weeren, P. R., Lopes-Cardozo, M., van Golde, L. M., Barneveld, A., and van de Lest, C. H. (1998) Anal Biochem 257, 107–11). Standards of galacturonic acid (GalA) and glucuronic acid (GlcA) ranging from 0–10 µg in a total volume of 40 µl water were added to the standard wells. Varying volumes of each of the DS oligosaccharide samples were diluted into 40 µl for comparison to the GalA and GlcA standards. 200 µl of sodium tetraborate in concentrated sulfuric acid was added to each well and mixed by pipetting. The plate was incubated at 80° C. for 1 hr. After the incubation, the plate was cooled to room temperature and 40 µl of a 1:100 dilution of 100 mg/ml 3-phenylphenol in DMSO with 80% sulfuric acid (v/v) in water was added to each well. The plate was incubated at room temperature for 15 min. and the color change was analyzed in a UV plate reader at $\lambda_{abs}$ of 540 nm. The absorbance of three different amounts of each oligosaccharide was compared to the standard curves to determine the molar concentration of uronic acid in each sample. The appropriate conversion factor for each length DS oligosaccharide (i.e. 5 moles GlcA/l mole Deca) was used to calculate the molar concentration of each oligosaccharide sample.

MALDI-mass Spectrometry

MALDI-MS experiments were completed conditions similar to those developed for the analysis of heparin/heparan sulfate oligosaccharides (Rhomberg, A. J., Ernst, S., Sasisekharan, R., and Biemann, K. (1998) Proc Natl Acad Sci USA 95, 4176–81). Briefly, a fresh saturated caffeic acid solution (~12 mg/ml) in 70% acetonitrile was mixed with a molar excess of basic peptide (arg-gly)$_{15}$ prior to the 1:10 dilution of the oligosaccharide. Spots were pre-seeded on a stainless steel MALDI plate as previously described (Rhomberg, A. J., Ernst, S., Sasisekharan, R., and Biemann, K. (1998) Proc Natl Acad Sci USA 95, 4176–81). A 1 µl aliquot of the sample/matrix solution was added to a pre-seeded spot and allowed to dry. MALDI-MS spectra were acquired in the linear mode on a PerSeptive Biosystems (Framingham, Mass.) Voyager Elite time-of-flight instrument. Delayed extraction was used to increase resolution as previously described (Rhomberg, A. J., Ernst, S., Sasisekharan, R., and Biemann, K. (1998) Proc Natl Acad Sci USA 95, 4176–81). Spectra were externally calibrated using the signals for the $RG_{15}$ and the $RG_{15}$:Deca complex.

Capillary Electrophoresis

Capillary electrophoresis was performed using similar conditions to those developed for the separation of heparin/heparan sulfate disaccharides (Rhomberg, A. J., Ernst, S., Sasisekharan, R., and Biemann, K. (1998) Proc Natl Acad Sci USA 95, 4176–81). Briefly, uncoated fused silica capillaries (i.d. of 75 µm and $I_{tot}$ of 80.5 cm) coupled with an extended path detection cell were used on a Hewlett-Packard $^{3D}$CE unit. Oligosaccharides were detected at 232 nm using an electrolyte solution of 50 mM Tris/phosphoric acid, pH 2.5. Dextran sulfate was added to the buffer to suppress nonspecific interactions with fused silica wall of the capillaries. Electrophoretic separation was performed using reverse polarity at a voltage of –30 kV. Peak identities were confirmed by co-migration with known standards. A dilution series of each oligosaccharide was run on the CE to generate a set of standard curves for determining the molar amount of each species in a electropherogram.

Results and Discussion

We generated a range of DS-derived oligosaccharides to use as defined substrates for the analysis of the mode of action of chondroitinase B. Coupling these defined substrates with the analytical techniques of CE and MALDI-MS, we were able to examine the time-resolved product formation resulting from the action pattern of chondroitinase B. We found that chondroitinase B is a non-random, non-processive, endolytic enzyme that preferentially cleaves longer substrates (decasaccharide) at a higher rate when compared to shorter ones (tetrasaccharide). In addition, the R364A mutant, previously shown to have decreased reaction kinetics and an altered product profile, also has an altered mode of action when compared to chondroitinase B further emphasizing the role for this arginine in substrate processing. This work provides a more comprehensive understanding of the structure-function relationship for these biologically important polysaccharides.

Enzymatic Generation and Isolation of Defined DS Oligosaccharides

Figure 6A:
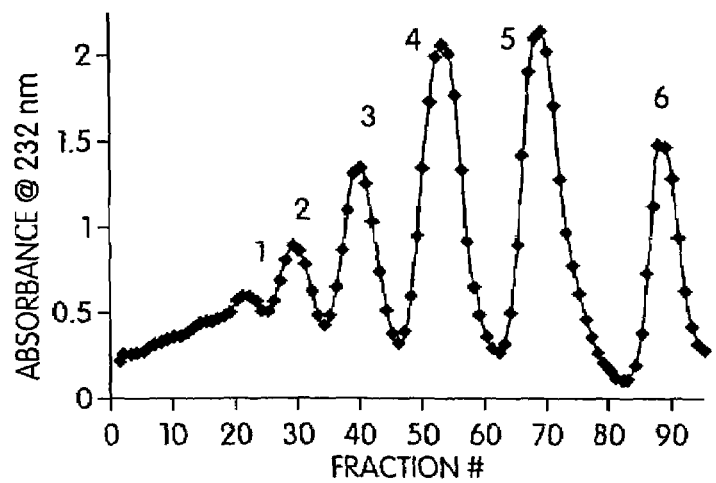
FIG. 6 illustrates the generation and purification of defined DS oligosaccharides. DS was partially digested with the chondroitinase B mutant, R364A, and the products were separated on a Bio-gel P6 column. (A) Six distinct peaks with absorbance at 232 nm were pooled, lyophilized, and further separated using HPLC. Each peak was analyzed using capillary electrophoresis and MALDI-MS to assess their purity and to assign their identity. (B) A representative electropherogram of the DS oligosaccharide from peak 2 confirms its purity. (C) The major oligosaccharide from peak 2 was complexed with the basic peptide, (arg-gly)$_{15}$, and analyzed using MALDI-MS. Subtracting the mass of the peptide (3218.9 Da) from the mass of the oligosaccharide: peptide complex (5515.9 Da) yielded an oligosaccharide with a mass of 2297.0 Da, identifying peak 2 as a decasaccharide with 5 sulfates. Peak 1 was identified as a dodecasaccharide with 6 sulfates, peak 3 was an octasaccharide with 4 sulfates, peak 4 was a hexasaccharide with 3 sulfates, peak 5 was a tetrasaccharide with 2 sulfates, and peak 6 was a mono-sulfated disaccharide.
Figure 6B:
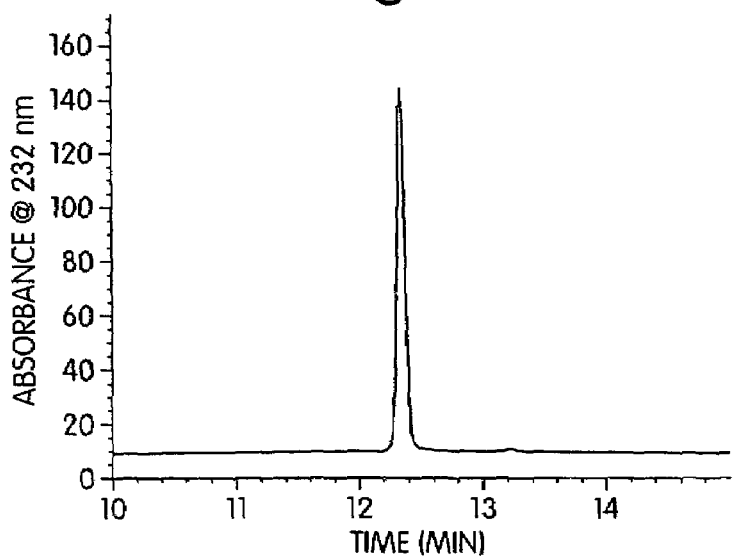
Figure 6C:
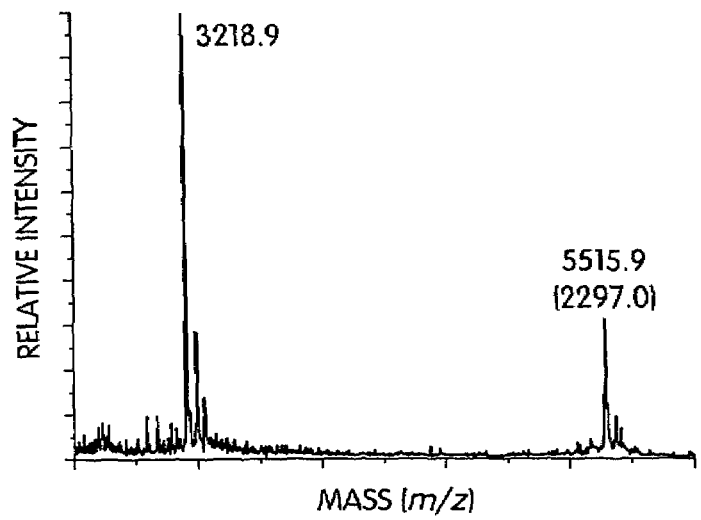

The first step in characterizing the mechanism of action of chondroitinase B was the generation and isolation of defined DS-derived oligosaccharides. Porcine intestinal mucosa DS was partially digested using the R364A mutant chondroitinase B that was previously shown to have decreased reaction kinetics allowing for a greater control over the rate of the digestion (Pojasek, K., Raman, R., Kiley, P., Venkataraman, G., and Sasisekharan, R. (2002) J Biol Chem 277, 31179–86). The reaction conditions were optimized to provide maximal yield of DS-derived oligosaccharides ranging from tetra- to dodecasaccharides. After the completion of the enzymatic digestion, the reaction products were separated on a Bio-gel P6 column yielding six defined peaks (FIG. 6, (A)). Each fraction was further purified using anion exchange HPLC and the resulting peaks were desalted to yield pure oligosaccharides.

Figure 7A:
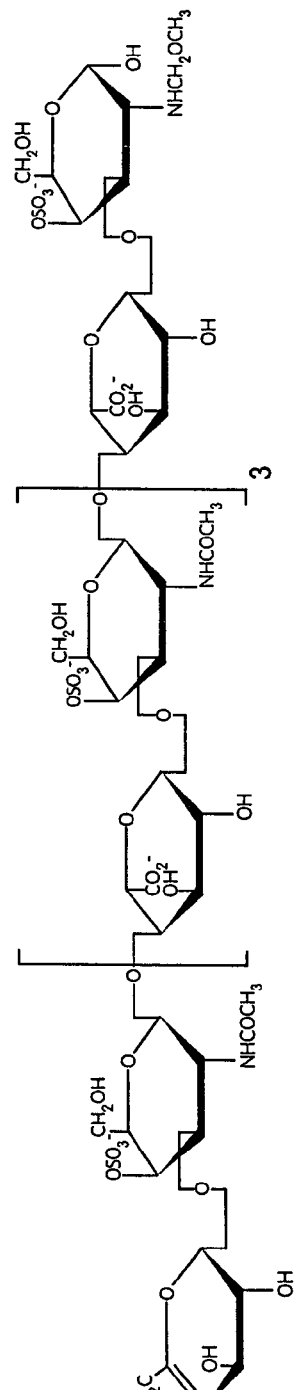
FIG. 7 provides the structure of relevant DS oligosaccharides. (A) A five-sulfated decasaccharide derived from the partial enzymatic digest of DS. The decasaccharide is characterized by sulfates at the 4-O position of each GalNAc, IdoA epimers of the uronic acids, and a $\Delta^{4,5}$ unsaturated double bond at the non-reducing end. (B) A three-sulfated hexasaccharide derived from the partial enzymatic digest of DS. (C) The same hexasaccharide as in (B) with a semicarbazide mass tag attached to its reducing end. The presence of the semicarbazide label enabled tracking of the reducing end disaccharide during the enzymatic degradation by capillary electrophoresis and MALDI-MS. The decasaccharide in (A) was also labeled in a similar fashion. (D) A schematic representation of the semicarbazide labeled hexasaccharide in (C). The triangle represents the non-reducing end 4-sulfated disaccharide with the $\Delta^{4,1627\ 5}$ double bond. Each circle is a 4-sulfated disaccharide and the star represents the semicarbazide label on the reducing end of the oligosaccharide. The arrows indicate potential cleavable bonds at site I and site II. (E) A schematic representation of a semicarbazide labeled decasaccharide. The shapes are the same as described for the hexasaccharide in (D). The decasaccharide has four cleavable bonds; two terminal, exolytic bonds (site I and IV) and two internal, endolytic bonds (site II and III).
Figure 7B:
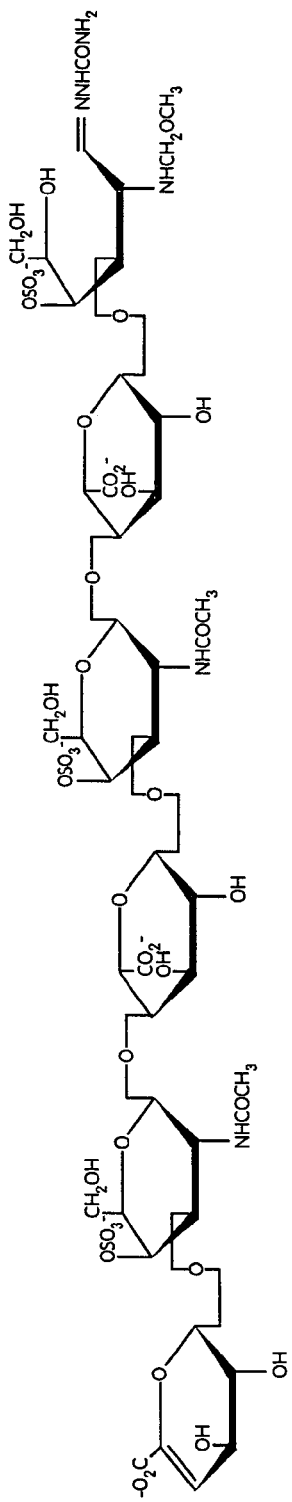
Figure 7C:
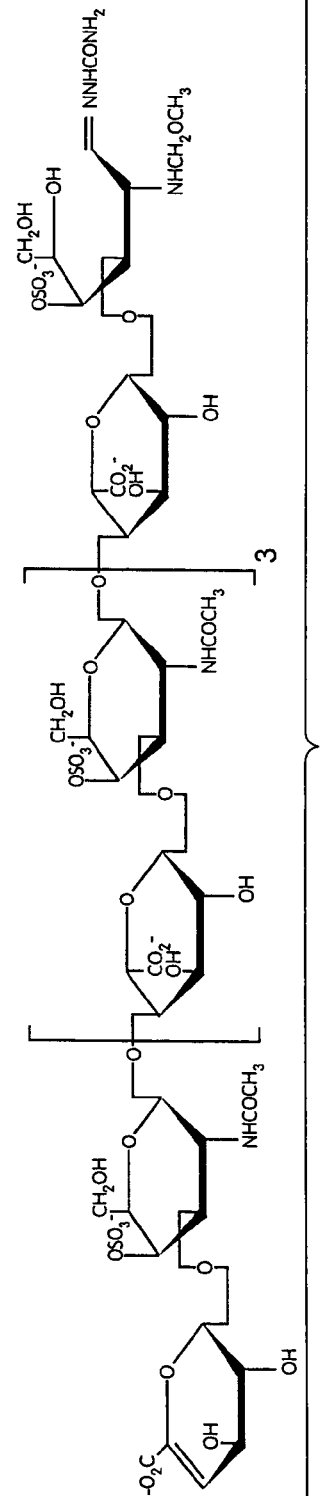
Figure 7D:
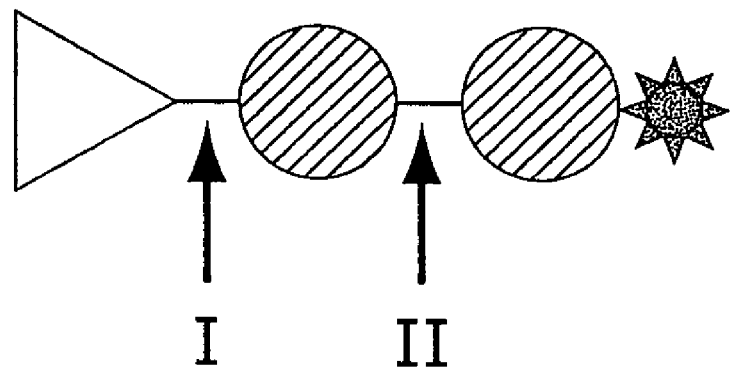
Figure 7E:
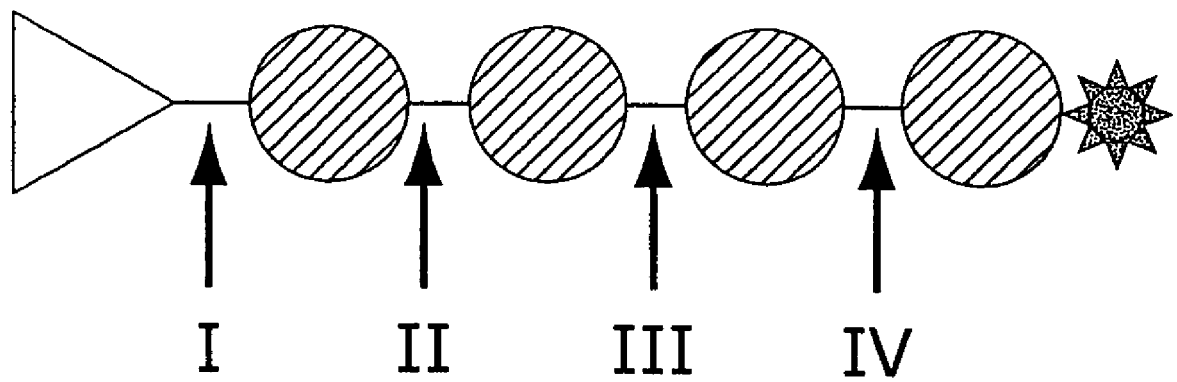

Each oligosaccharide isolated from the six peaks in the P6 profile was analyzed using a tandem approach of CE and MALDI-MS to confirm its identity, purity, and composition (Table 3). As a representative of this analysis, is a CE electropherogram of the major constituent of Peak 2 in the P6 profile. The single peak in the CE profile clearly indicated that the oligosaccharides had been purified to homogeneity (FIG. 6 (B)). For the MALDI-MS analysis, the oligosaccharide resulting from Peak 2 was complexed with a basic peptide ($RG_{15}$) and analyzed in the linear mode. The MALDI-MS profile revealed two defined peaks representing the uncomplexed $RG_{15}$ (3218.9 Da) and the oligosaccharide: peptide complex (5525.9 Da) (FIG. 6(C)). The difference between the masses of the two peaks (2297.0 Da) confirms that Peak 2 from the P6 profile is a decasaccharide with 5 sulfates. The mass of the decasaccharide calculated from the MALDI-MS data agrees exactly with the expected mass (Table 3). Compositional analysis of the decasaccharide peak using chondroitinase ABC revealed that the 4-O-sulfated disaccharide (Di) was the sole product confirming the structure in FIG. 7(A).

TABLE 3

DS-derived Oligosaccharides and their masses

| Oligosaccharide | Chemical Structure | Complex Mass (Da) | Calculated Mass (Da) | Expected Mass (Da) |
|---|---|---|---|---|
| Di | $\Delta$UA-$H_{NAc,4S}$ | n.d. | n.d. | 503.3 |
| Di-sc | $\Delta$UA-$H_{NAc,4S}$-sc | n.d. | n.d. | 560.4 |
| Tetra | $\Delta$UA-$H_{NAc,4S}$-I-$H_{NAc,4S}$ | 4316.7 | 918.8 | 918.8 |
| Tetra-sc | $\Delta$UA-$H_{NAc,4S}$-I-$H_{NAc,4S}$-sc | 4192.5 | 976.7 | 975.9 |
| Hexa | $\Delta$UA-$H_{NAc,4S}$-(I-$H_{NAc,4S}$)$_2$ | 4690.9 | 1378.5 | 1378.2 |
| Hexa-sc | $\Delta$UA-$H_{NAc,4S}$-(I-$H_{NAc,4S}$)$_2$-sc | 4650.8 | 1435.2 | 1435.3 |
| Octa | $\Delta$UA-$H_{NAc,4S}$-(I-$H_{NAc,4S}$)$_3$ | 5057.2 | 1837.5 | 1837.6 |
| Octa-sc | $\Delta$UA-$H_{NAc,4S}$-(I-$H_{NAc,4S}$)$_3$-sc | 5109.8 | 1895.0 | 1894.7 |
| Deca | $\Delta$UA-$H_{NAc,4S}$-(I-$H_{NAc,4S}$)$_4$ | 5515.9 | 2297.0 | 2297.0 |
| Deca-sc | $\Delta$UA-$H_{NAc,4S}$-(I-$H_{NAc,4S}$)$_4$-sc | 5568.4 | 2354.1 | 2354.1 |
| DoDeca | $\Delta$UA-$H_{NAc,4S}$-(I-$H_{NAc,4S}$)$_5$ | 5972.8 | 2755.8 | 2756.4 |

The same combination of CE, MALDI-MS, and compositional analysis was performed on all of the isolated oligosaccharides to confirm their identity and purity. Peak 1 from the P6 profile was a dodecasaccharide containing 6 sulfates with a mass of 2755.8 Da (Table 3). Peak 3 was an octasaccharide with 4 sulfates at an observed mass of 1837.5 Da. Peak 4 yielded a hexasaccharide containing 3 sulfates and a mass of 1378.5 Da. Peak 5 was a tetrasaccharide with 2 sulfates with a mass of 918.8 Da. Importantly, all of the masses for the oligosaccharides obtained by MALDI-MS deviated from the expected mass by $\leq 1$ Da (Table 3). Finally, peak 6 was identified as the 4-sulfated disaccharide using CE and was not analyzed by MALDI-MS (Table 3).

The use of MALDI-MS was helpful in assigning the identity of each of the oligosaccharides isolated from the partial digest of DS. A computational exercise completed previously by our group revealed that from only the mass of a GAG oligosaccharide of up to a tetradecasaccharide in length, one could assign the oligosaccharide length and the number of sulfates that modify it (Venkataraman, G., Shriver, Z., Raman, R., and Sasisekharan, R. (1999) Science 286, 537–42). Combining this MALDI-MS analysis with the CE-based compositional analysis, we were able to unambiguously assign a structure to each of the DS-derived oligosaccharides (Table 3). Prior NMR analysis of DS-derived oligosaccharides identified all of the saturated uronic acids as IdoA (Yang, H. O., Gunay, N. S., Toida, T., Kuberan, B., Yu, G., Kim, Y. S., and Linhardt, R. J. (2000) Glycobiology 10, 1033–9). Therefore, the logical assumption was made that the structures of the oligosaccharides in the current study contain IdoA. It is important to note that while one previous study used MALDI-MS to identify a single DS-derived hexasaccharide (Ueoka, C., Nadanaka, S., Seno, N., Khoo, K. H., and Sugahara, K. (1999) Glycoconj J 16, 291–305), the current study represents the first broad-range application of MALDI-MS for the characterization of a diversity of DS-derived oligosaccharides.

Molar Quantitation of CE Data

To develop a more quantitative technique for representing the amount of the different oligosaccharide products in a given CE profile, a set of standard curves were generated using the uronic acid plate assay (van den Hoogen, B. M., van Weeren, P. R., Lopes-Cardozo, M., van Golde, L. M., Barneveld, A., and van de Lest, C. H. (1998) Anal Biochem 257, 107–11). Glucuronic acid and galacturonic acid (0–21 nmol) were used to generate standard curves to which each of the DS-derived oligosaccharides (Di-Deca) was compared, thereby enabling the determination the molar concentration of each of the oligosaccharides. The GlcA and GalA standard curves compared well with one another and the uronic acid assay was repeated at least six times for each oligosaccharide to insure a standard deviation of less than 10%. In parallel, a dilution series of each oligosaccharide was run on the CE, and the peak areas were plotted as a function of oligosaccharide sample concentration. These experiments yielded a set of standard curves that enable the direct conversion of a CE peak area into a molar concentration of that oligosaccharide in a sample. Using these standard curves, the molar amount of each reaction product, as well as each substrate, was calculated for all of the enzymatic reactions described below.

Mechanism of Action of Chondroitinase B

Figure 8A:
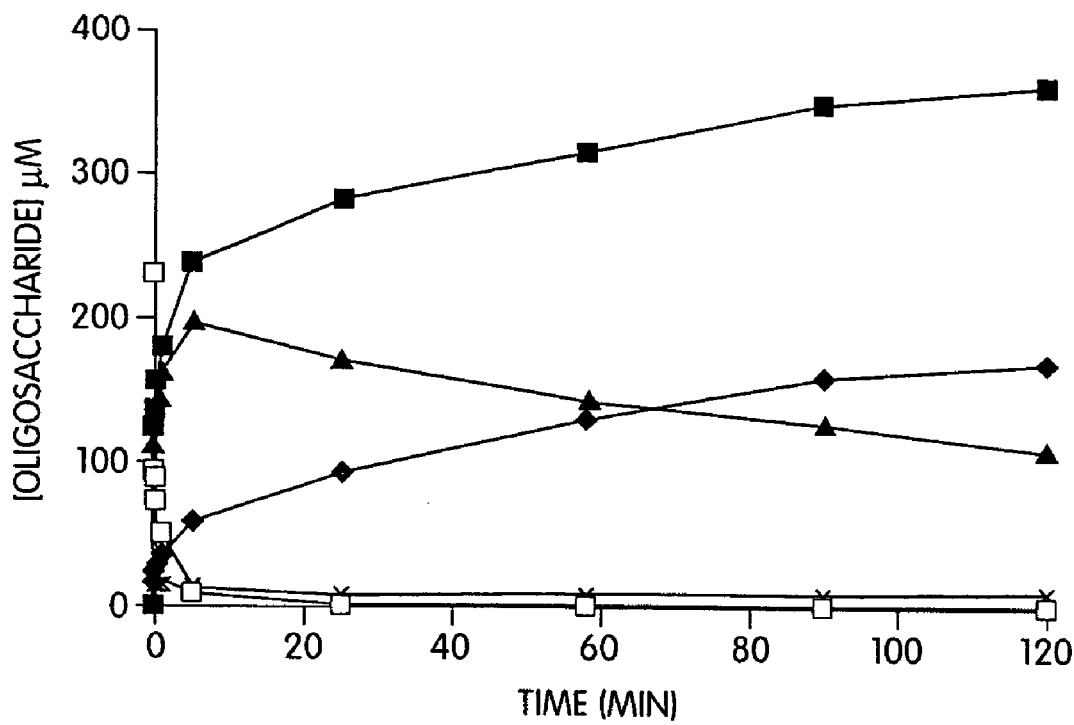
FIG. 8 provides results of chondroitinase B degradation of Deca. Chondroitinase B was incubated with the five-sulfated decasaccharide for defined period of times, and the enzymatic products were analyzed by CE. The resulting peak areas in the electropherogram were converted to molar concentrations and plotted versus time. (A) During the 120 min. digestion of Deca (□), there was an initial appearance of Tetra (■) and Hexa (▲) with very little Octa (x) and Di (♦) products indicating that chondroitinase B is an endolytic enzyme. (B) This observation was confirmed by examining the products of the enzymatic reaction during the first 60 s. Later in the reaction time course as Deca was depleted (A), the concentration of Hexa decreased with a concomitant increase in Di and Tetra, implying that chondroitinase B prefers longer substrates (Deca) to shorter ones (Hexa).
Figure 8B:
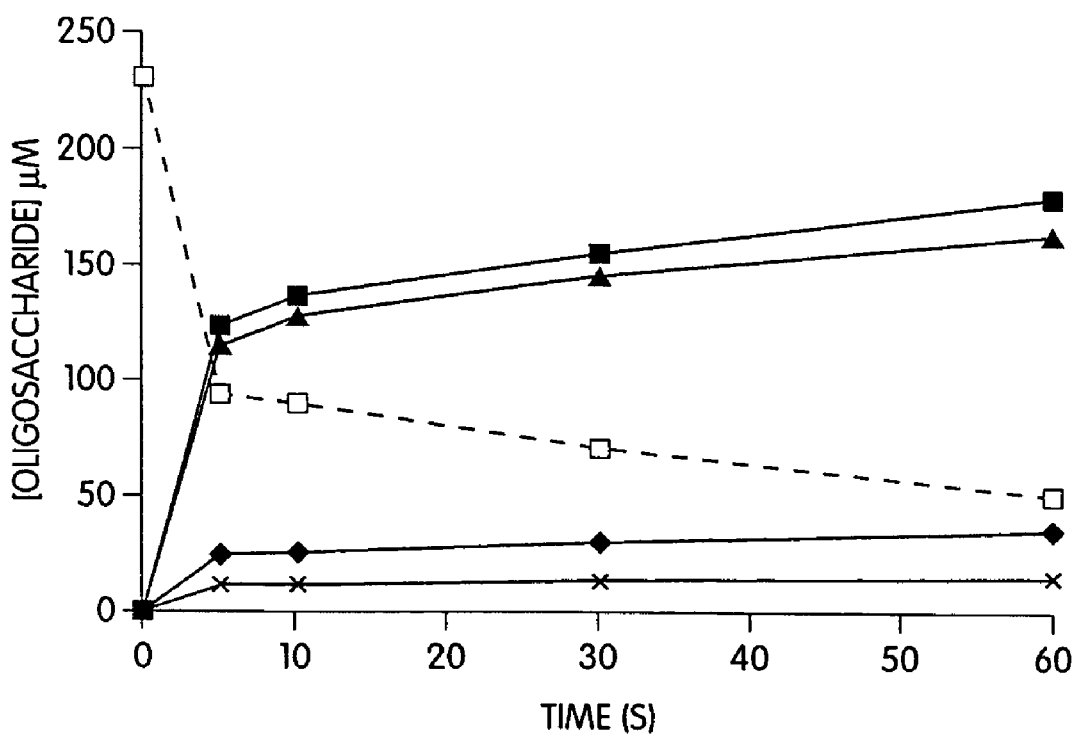

The 5-sulfated decasaccharide (Deca) was selected as the initial substrate for exploring the action pattern of chondroitinase B. Deca's reasonable length and its two cleavable internal bonds as well as two external bonds make it an ideal substrate for these experiments (FIG. 7, (A)). Enzymatic reactions conditions were optimized such that the product profile at a variety of time points could be analyzed using CE. Ultimately, 300 nM chondroitinase B was incubated with 220 µM Deca at 30° C. Aliquots were removed at varying time points ranging from 10 s to 120 min, heat inactivated, diluted, and analyzed by CE. The peak areas for the different reaction products were used to calculate a molar concentration for each oligosaccharide that, in turn, was plotted as a function of time (FIG. 8). Each of the oligosaccharide peaks were identified by co-migration with defined oligosaccharide standards and confirmed by MALDI-MS.

Over the 120 min time course of the experiment, the major product produced was Tetra with significant yet diminishing amounts of Hexa also present (FIG. 8, (A)). Examination of the products produced during the first 60 s of the reaction revealed that Tetra and Hexa were produced in increasing, nearly equal molar amounts with negligible amounts of Octa and Di produced during this early phase of the reaction (FIG. 8, (B)). Taken together, these results clearly demonstrate that chondroitinase B is an endolytic enzyme. In fact, a comparison of the amount of Hexa (the product of endolytic cleavage) to Octa (the product of exolytic cleavage) produced during the first minute of the reaction yields a 91% endolytic mode of action for chondroitinase B. Additionally, the lack of Di products implies that chondroitinase B is a non-processive enzyme. Di would be an obvious reaction product if chondroitinase B continued to degrade a bound oligosaccharide, a pattern that is seen with both heparinase I and endogalacturonase I from *Asperillus niger* with their respective substrates (Ernst, S., Rhomberg, A. J., Biemann, K., and Sasisekharan, R. (1998) Proc Natl Acad Sci USA 95, 4182–7; Pages, S., Kester, H. C., Visser, J., and Benen, J. A. (2001) J Biol Chem 276, 33652–6). Chondroitinase B likely releases the cleavage products after each round of degradation with subsequent rebinding initiating the next round of catalysis in a similar fashion to heparinase II (Rhomberg, A. J., Shriver, Z., Biemann, K., and Sasisekharan, R. (1998) Proc Natl Acad Sci USA 95, 12232–7). Importantly, the direct observation of the endolytic action pattern reported here is in agreement with a previous study that relied on changes in sample viscosity and gel electrophoresis as indirect measures of the mechanism of action of chondroitinase B (Jandik, K. A., Gu, K., and Linhardt, R. J. (1994) Glycobiology 4, 289–96).

Another interesting observation is that the molar concentrations of Tetra and Hexa in the reaction became divergent once the Deca substrate had been depleted. In addition, a rise in the concentration of Di accompanied the rise in the concentration of Tetra (FIG. 8, (A)). These observations suggest that chondroitinase B prefers longer substrates, such as Deca to shorter ones, such as Hexa. To confirm this observation, each of the oligosaccharides at a concentration of approximately 150 µM was digested independently with chondroitinase B and the rate of product appearance was measured using CE and corrected for enzyme concentration. Chondroitinase B shows a clear preference for longer oligosaccharides with the rate of cleavage for Deca being 18-fold higher than the rate of cleavage for Tetra. In addition, chondroitinase B cleaves Octa at a 7-fold higher rate than it cleaves Hexa. This preference for longer substrates is comparable to what was observed with both heparinase I and II (Ernst, S., Rhomberg, A. J., Biemann, K., and Sasisekharan, R. (1998) Proc Natl Acad Sci USA 95, 4182–7; Rhomberg, A. J., Shriver, Z., Biemann, K., and Sasisekharan, R. (1998) Proc Natl Acad Sci USA 95, 12232–7), hyaluronan lyase from group B streptococci (Baker, J. R., and Pritchard, D. G. (2000) Biochem J 348 Pt 2, 465–71), and the endopectate lyases from *Erwinia chrysanthemi* (Roy, C., Kester, H., Visser, J., Shevchik, V., Hugouvieux-Cotte-Pattat, N., Robert-Baudouy, J., and Benen, J. (1999) J Bacteriol 181, 3705–9).

Chondroitinase B Digestion of End-labeled Oligosaccharides

The DS oligosaccharides were labeled at the reducing end with semicarbazide thereby introducing a mass tag that could be tracked by mass spectrometry (Rhomberg, A. J., Shriver, Z., Biemann, K., and Sasisekharan, R. (1998) Proc Natl Acad Sci USA 95, 12232–7). To ensure the reducing end had been labeled, the reactions were analyzed by both CE and MALDI-MS. Interestingly, the end-labeled oligosaccharides had a noticeable increase in their migration time in the CE. The redistribution of the charge density that results from the semicarbazide label stabilizing the ring-opened form of the GalNAc likely produces this observed migration time shift (FIGS. 7, (B) and (C)). Capitalizing on this shift in migration time and the relative simplicity of the reaction products from DS, we were able to use the CE to track the formation of the reaction products that contained the reducing end GalNAc labeled with semicarbazide and compare them to products generated from internal cleavage of the oligosaccharide substrate. The reaction products are expressed as the fraction of each respective the oligosaccharide species in the electropherogram [i.e. Hexa-sc/(Hexa-sc+Hexa)]. This enabled us to directly assign relative rates of cleavage for the different bonds in up to a decasaccharide by chondroitinase B. In addition, the integration of each oligosaccharide peak in an electropherogram resulted in significantly more quantitative data than that produced using MALDI-MS or other MS-based techniques that are semi-quantitative at best (Rhomberg, A. J., Ernst, S., Sasisekharan, R., and Biemann, K. (1998) Proc Natl Acad Sci USA 95, 4176–81). Therefore, this CE-based technique represents a significant improvement on previous techniques used to explore the action pattern of other polysaccharide degrading enzymes (Rhomberg, A. J., Shriver, Z., Biemann, K., and Sasisekharan, R. (1998) Proc Natl Acad Sci USA 95, 12232–7).

Digestion of Hexa-sc

A pure hexasaccharide with 3 sulfates was labeled with semicarbazide overnight at 40° C. (FIGS. 7, (B) and (D)). The efficiency of the labeling reaction was 95% as determined by CE. The mass observed mass of Hexa-sc was 1435.2 Da as measured by MALDI-MS indicating an increase of 57.0 Da (expected increase of 57.1 Da) by the addition of the semicarbazide tag (Table 3). Compositional analysis of Hexa-sc yielded Di and Di-sc products at the expected ration of 2:1.

Experiments were performed to determine suitable digestion conditions under which the products as well as the substrate were detectable using CE and MALDI-MS.

Figure 9A:
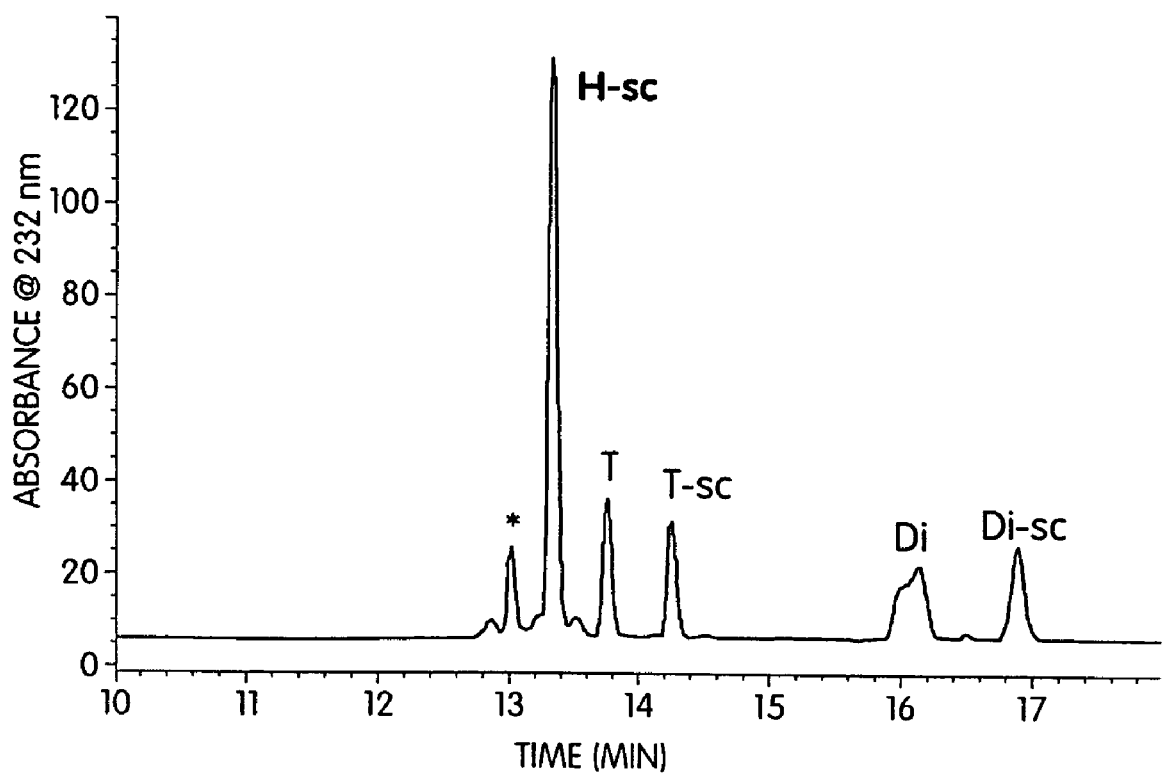
FIG. 9 provides results from the digestion of Hexa-sc. A hexasaccharide labeled at the reducing end was digested with chondroitinase B (A) and the R364A mutant (B) and analyzed using capillary electrophoresis. (A) The initial reaction products resulting from the digestion of the Hexa-sc (H-sc) substrate by chondroitinase B are Tetra (T), Tetra-sc (T-sc), Di and Di-sc. (B) There was a noticeable increase in the relative concentration of T-sc and Di produced when H-sc was degraded by R364A, suggesting that this mutant has an altered mode of action when compared to chondroitinase B. (* denotes the remaining unlabeled Hexa impurity from the semicarbazide labeling).
Figure 9B:
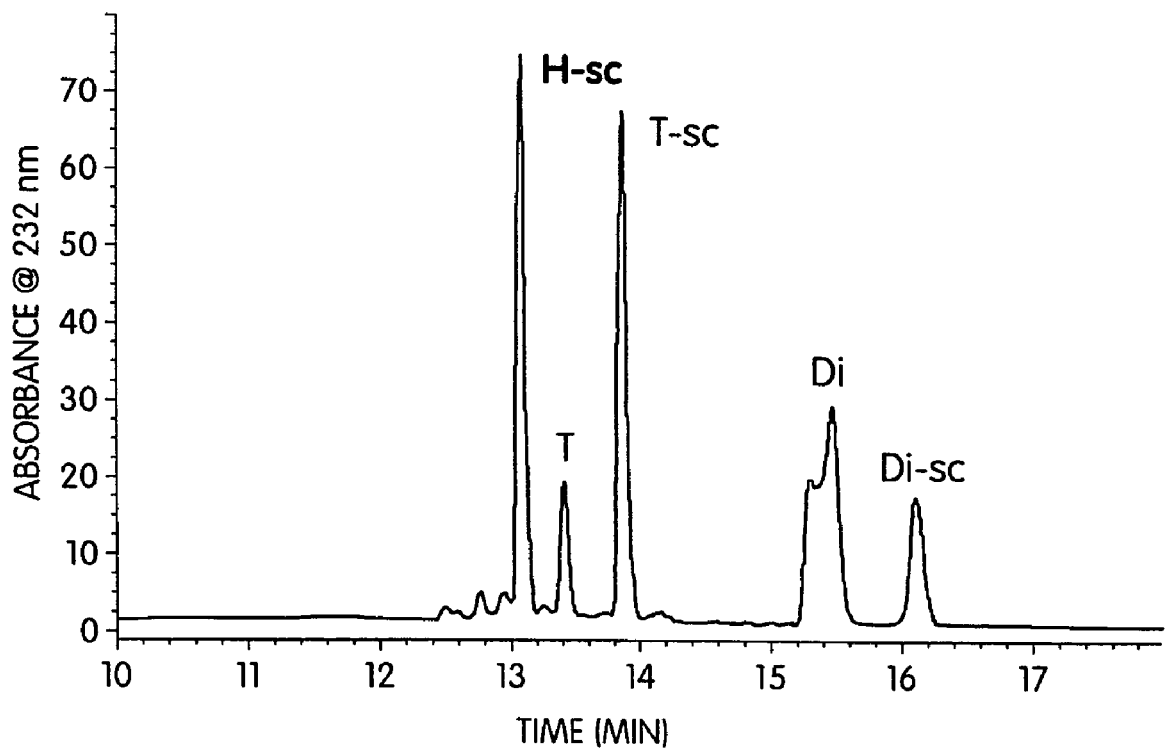

Recombinant chondroitinase B was added to a concentration of 170 nM to the labeled hexasaccharide and incubated at 30° C. for 3 min. The sample was heat inactivated at 85° C. for 5 min. and then analyzed by CE. Under these reaction conditions, detectable amounts of Tetra and Tetra-sc as well as Di and Di-sc were observed (FIG. 9, (A) and Table 4). A significant amount of the Hexa-sc substrate remained present indicating that the products observed in the CE were indicative of the initial rate of enzymatic cleavage (FIG. 9, (A)). The products of cleavage at both Site I and Site II in the Hexa-sc are close to evenly distributed suggesting that chondroitinase B cleaves each bond with equal efficiency (Table 4). The slight disparity between the higher molar proportions of the unlabeled products compared to the labeled products likely results from the cleavage of the remaining unlabeled substrate material still present in the starting sample (Table 4 and FIG. 9, (A)). Importantly, the activity of chondroitinase B did not seem to be altered by the presence of the semicarbazide group on Hexa-sc as, a priori, the enzyme would be expected to cleave both internal bonds of a hexasaccharide with equal efficiency givens its endolytic nature.

TABLE 4

Cleavage of Hexa-sc with Chondroitinase B

| Cleavage Site | Reaction Product | [Oligosaccharide] µM | Fraction of Species |
|---|---|---|---|
| Site I | Tetra-sc | 24.8 | 0.46 |
|  | Di | 33.4 | 0.59 |
| Site II | Tetra | 29.3 | 0.54 |
|  | Di-sc | 23.9 | 0.41 |

Digestion of Deca-sc

A decasaccharide with 5 sulfates was labeled at the reducing end with semicarbazide (FIGS. 7, (C) and (E)). The labeling reaction was 98% complete as indicated by CE. The mass observed mass of Deca-sc was 2354.1 Da as measured by MALDI-MS indicating that an increase of 57.1 Da (expected increase of 57.1 Da) by the addition of the semicarbazide tag (Table 3). Compositional analysis of Deca-sc yielded Di and Di-sc in the expected ratio of 4:1.

Figure 10A:
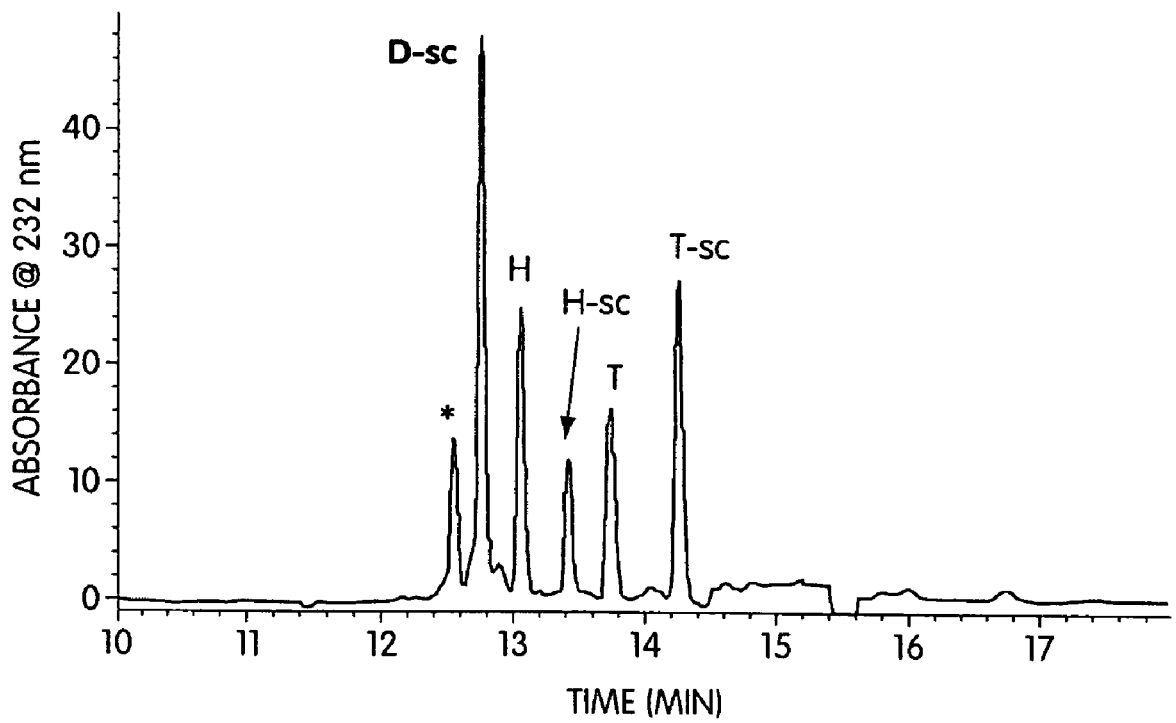
FIG. 10 provides the results of the digestion of Deca-sc. A decasaccharide labeled at the reducing end with semicarbazide was digested with chondroitinase B (A) and the R364A mutant (B) and analyzed by capillary electrophoresis. (A) The major products of the digestion of Deca-sc (D-sc) were Hexa-sc (H-sc), Hexa (H), Tetra-sc (T-sc), and Tetra (T). The higher relative amounts of T and H-sc indicate that chondroitinase B acts in a non-random fashion, preferring to cleave the internal bond proximal to the reducing end to the internal bond nearest the non-reducing end. (B) Digestion of D-sc with the R364A mutant produces the same products as in the chondroitinase B digestion. However, the relative amount of each product is different implying that the R364A mutant has lost the non-random aspect of the mode of action, thus cleaving both internal bonds with near equal efficiency. (* denotes the remaining unlabeled Deca impurity from the semicarbazide labeling)
Figure 10B:
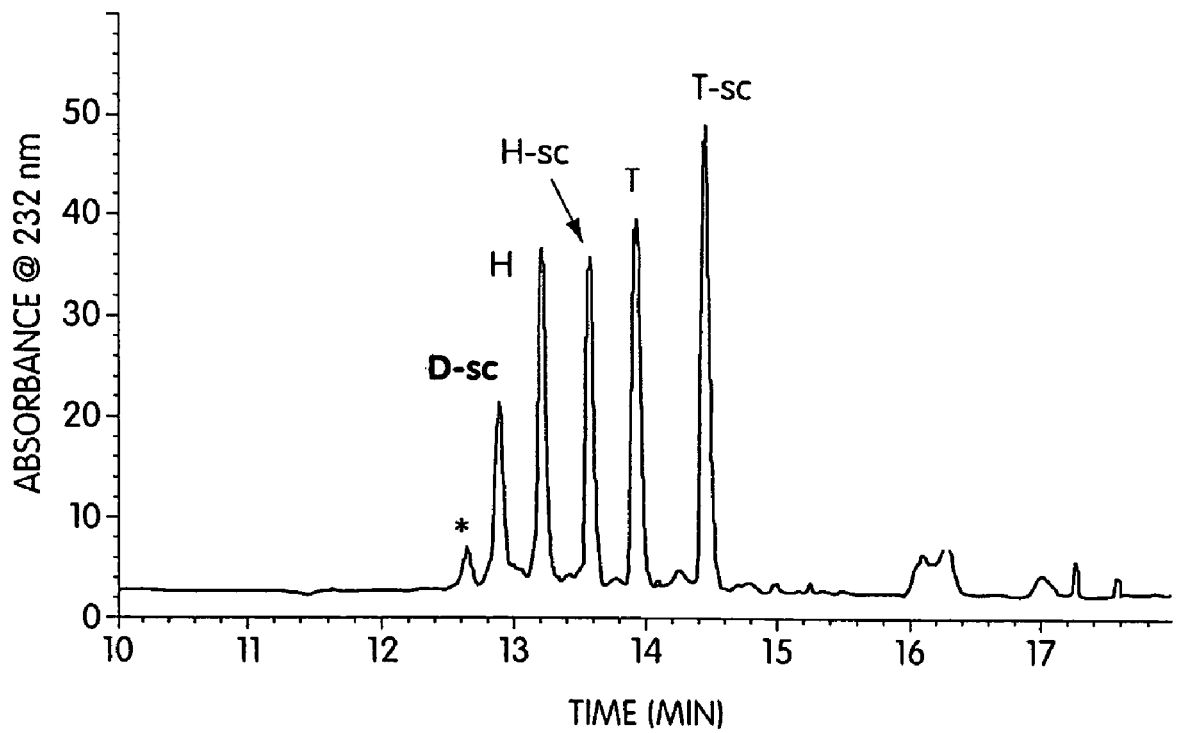

Chondroitinase B at a final concentration of 170 nM was incubated with Deca-sc at 30° C. for 30 s, heat inactivated, and analyzed by CE. After the 30 s digestion, a significant amount of the Deca-sc substrate was still present, representing 36% of the total peak area in the electrophoretogram, indicating that the reaction was in its initial phase (FIG. 10, (A)). In agreement with the endolytic mechanism of chondroitinase B, no Octa or Di products were formed during the initial cleavage of Deca-sc implying that cleavage occurred only at Site II and III (FIG. 2, (E)). The lack of Di products also suggests that the enzyme is not processive. Interestingly, the product profile suggests that chondroitinase B prefers to cleave Deca-sc at Site III, the internal bond closest to the reducing end at a threefold higher rate than Site II, the internal bond closer to the non-reducing end (FIG. 10, (A) and Table 5). This unequal cleavage is in contrast to the Hexa-sc data where both bonds are cleaved with equal efficiency by chondroitinase B and implies that the enzyme is non-random in addition to endolytic (Table 4).

TABLE 5

Cleavage of Deca-sc with chondroitinase B

| Cleavage Site | Reaction Product | [Oligosaccharide] µM | Fraction of Species |
|---|---|---|---|
| Site II | Tetra | 13.3 | 0.38 |
|  | Hexa-sc | 13.0 | 0.34 |
| Site III | Tetra-sc | 23.1 | 0.62 |
|  | Hexa | 24.8 | 0.66 |

The R364A Chondroitinase B Mutant

A combination of crystal structure analysis (Huang, W., Matte, A., Li, Y., Kim, Y. S., Linhardt, R. J., Su, H., and Cygler, M. (1999) J Mol Biol 294, 1257–69) and modeling (Pojasek, K., Raman, R., Kiley, P., Venkataraman, G., and Sasisekharan, R. (2002) J Biol Chem 277, 31179–86) previously implicated Arg364 in chondroitinase B in binding DS. Specifically, the basic side chain of this amino acid was positioned to make favorable contacts with the 4-O sulfate of the GalNAc occupying the putative −1 subsite in chondroitinase B (Huang, W., Matte, A., Li, Y., Kim, Y. S., Linhardt, R. J., Su, H., and Cygler, M. (1999) J Mol Biol 294, 1257–69; Pojasek, K., Raman, R., Kiley, P., Venkataraman, G., and Sasisekharan, R. (2002) J Biol Chem 277, 31179–86). Given that 4-O sulfation is the hallmark modification present in DS, Arg364 was speculated to play a critical role in determining the substrate specificity of chondroitinase B. In fact, when this residue was mutated to alanine, the resulting chondroitinase B mutant displayed diminished catalytic efficiency and an altered product profile as analyzed by CE (Pojasek, K., Raman, R., Kiley, P., Venkataraman, G., and Sasisekharan, R. (2002) J Biol Chem 277, 31179–86). Therefore, we sought to further examine the effect of the R364A mutation on the action pattern of chondroitinase B by digesting Hexa-sc and Deca-sc with the mutant enzyme.

Hexa-sc was first digested with the R364A mutant. Since the R364A mutant has a significantly reduced catalytic efficiency compared to chondroitinase B, 370 nM of enzyme was used and the reaction was incubated for 20 min. at 30° C. The reaction was heat inactivated as before and analyzed using CE. After the 2 hr incubation with R364A, the reaction still contained 25% of the initial Hexa-sc substrate and the distribution of reaction product was noticeably different from the distribution produced with the recombinant chondroitinase B (FIG. 9, (B) and Table 6). Instead of degrading each bond with equal efficiency as seen with chondroitinase B (Table 4), the product profile suggests that the R364A mutant cleaves at Site I with a four-fold higher rate than at Site II as indicated by the 4:1 molar distribution ratio of the products (Table 6). Therefore, the R364A mutant, in addition to having reduced reaction kinetics, also has an altered action pattern on a hexasaccharide substrate.

TABLE 6

Cleavage of Hexa-sc with R364A

| Cleavage Site | Reaction Product | [Oligosaccharide] µM | Fraction of Species |
|---|---|---|---|
| Site I | Tetra-sc | 60.5 | 0.78 |
|  | Di | 56.8 | 0.75 |
| Site II | Tetra | 17.0 | 0.22 |
|  | Di-sc | 19.5 | 0.25 |

Deca-sc was digested with R364A to examine if the differences in the action pattern seen with the Hexa-sc substrate were replicated with a decasaccharide. As was the case with the Hexa-sc reaction, 370 nM R364A was incubated with Deca-sc for 1 min to compensate for the reduced catalytic efficiency of R364A compared to that chondroitinase B. Similarly to the CE profile produced by chondroitinase B, the R364A product profile shows no significant production of Octa or Di species (FIG. 10, (B)). Therefore, the Arg to Ala mutation does not alter the endolytic mechanism or lack of processivity of chondroitinase B. However, in contrast to the chondroitinase B CE profile, the R364A product profile suggests that the mutant cleaves Site II and III at close to comparable rates as indicated by the nearly equivalent molar ratio of the reaction products (Table 7 and FIG. 10, (B)). Therefore, the Arg364Ala mutation alters the preference of chondroitinase B from cleaving closer to the reducing end of the oligosaccharide at Site III to cleaving both of the internal bonds at a comparable rate.

TABLE 7

Cleavage of Deca-sc with R364A

| Cleavage Site | Reaction Product | [Oligosaccharide] µM | Fraction of Species |
|---|---|---|---|
| Site II | Tetra | 22.6 | 0.47 |
|  | Hexa-sc | 20.9 | 0.42 |
| Site III | Tetra-sc | 25.1 | 0.53 |
|  | Hexa | 28.7 | 0.58 |

The results above clearly demonstrate that Arg364 is important in the normal enzymatic processing of DS by chondroitinase B. Comparing the product profile of the degradation of Hexa-sc by chondroitinase B with the R364A mutant, clearly demonstrates that Arg364 contributes important contacts with the DS substrate in the −1 subsite that allow for its normal positioning in the active site (Huang, W., Matte, A., Li, Y., Kim, Y. S., Linhardt, R. J., Su, H., and Cygler, M. (1999) J Mol Biol 294, 1257–69; Pojasek, K., Raman, R., Kiley, P., Venkataraman, G., and Sasisekharan, R. (2002) J Biol Chem 277, 31179–86). Removal of these contacts leads to a three-fold increase in cleavage rate at Site II compared to Site I (Table 7) suggesting that there is likely another residue(s) in the +1 or +2 subsite responsible for positioning the substrate for cleavage (Pojasek, K., Raman, R., Kiley, P., Venkataraman, G., and Sasisekharan, R. (2002) J Biol Chem 277, 31179–86). In fact, the R364A mutant is unable to cleave Tetra as a substrate further implying that a balance of contacts between the −1 and the +1/+2 subsites is required for the normal catalytic function of chondroitinase B. Furthermore, the altered product profile with Deca-sc confirms that Arg364 is required for normal substrate binding. In fact, removal of Arg364 leads to shift in the action pattern of chondroitinase B from non-random to random. Similarly altering a single amino acid in endopolygalacturonase I and II leads to shift from processive to a non-processive mode of action (Pages, S., Kester, H. C., Visser, J., and Benen, J. A. (2001) J Biol Chem 276, 33652–6). However, in this case the R364A mutant retains the non-processive, endolytic mechanism displayed by chondroitinase B.

We have applied the analytical techniques of CE and MALDI-MS to the quantitative analysis of the enzymatic degradation products from the depolymerization of defined DS-derived oligosaccharides by chondroitinase B. Chondroitinase B degrades polymeric DS substrates in a non-random, non-processive, endolytic mode of action and kinetically favors longer substrates to shorter ones. Labeling the reducing end of defined hexa- and decasaccharide with semicarbazide provided a convenient mass tag and altered the migration time of the oligosaccharides in the CE. Using these labeled oligosaccharides, we were able to demonstrate that chondroitinase B favors endolytic bonds closer to the reducing end of the substrate. In addition, examination of the product profile of the R364A mutant revealed that this residue plays a critical role in the binding of DS substrates for catalysis. Removal of Arg364 leads to a random action pattern without altering the endolytic, non-processive function of chondroitinase B.

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A method for isolating a recombinant chondroitinase, comprising:
   lysing a cell culture containing a recombinant chondroitinase having a terminal histidine tag, and
   passing the recombinant chondroitinase over a charged Ni 2+ column to isolate the recombinant chondroitinase,
   wherein the recombinant chondroitinase is a modified chondroitinase B having an amino acid sequence of the mature peptide of SEQ ID NO: 2 or conservative substitutions thereof, wherein at least one residue at a position selected from the group consisting of 116, 184, 213, 219, 245, 250, 271, 272, 296, 298, 318, 333, 363 and 364 of SEQ ID NO: 2 has been substituted or deleted.

2. The method of claim 1, wherein the recombinant chondroitinase is selected from the group consisting of chondroitinase AC, chondroitinase B or a modified chondroitinase B.

3. A method for purifying a recombinant chondroitinase, comprising:
   inducing a culture of cells containing a recombinant chondroitinase with an inducing agent for greater than four hours, and
   isolating the recombinant chondroitinase from the cells to produce a purified chondroitinase,
   wherein the recombinant chondroitinase is a modified chondroitinase B having an amino acid sequence of the mature peptide of SEQ ID NO: 2 or conservative substitutions thereof, wherein at least one residue at a position selected from the group consisting of 116, 184, 213, 219, 245, 250, 271, 272, 296, 298, 318, 333, 363 and 364 of SEQ ID NO: 2 has been substituted or deleted,
   and wherein the inducing agent is isopropyl-B-D-thiogalactopyranoside.

4. The method of claim 3, wherein the cells are incubated with the inducing agent at a temperature of between 20° and 26° C.

5. The method of claim 3, wherein the cells are incubated with the inducing agent for at least 8 hours.

6. The method of claim 4, wherein the cells are incubated with the inducing agent for at least 8 hours.

7. The method of claim 3, wherein the recombinant chondroitinase includes a terminal histidine tag.

8. The method of claim 7, wherein the method further comprises passing the recombinant chondroitinase over a charged Ni 2+ column to isolate the recombinant chondroitinase.

* * * * *

UNITED STATES PATENT AND TRADEMARK OFFICE
CERTIFICATE OF CORRECTION

| | | |
|---|---|---|
| PATENT NO. | : 7,129,335 B2 | Page 1 of 1 |
| APPLICATION NO. | : 10/966671 | |
| DATED | : October 31, 2006 | |
| INVENTOR(S) | : Kevin Pojasek et al. | |

It is certified that error appears in the above-identified patent and that said Letters Patent is hereby corrected as shown below:

In the Specification:

At column 1, lines 16-19, please delete

"Aspects of the invention may have been made using funding from National Institutes of Health Grant number Grant GM 57073. Accordingly, the Government may have rights in the invention."

and insert

-- This invention was made with government support under Grant No. R01 GM57073, awarded by the National Institutes of Health. The government has certain rights in this invention. --

Signed and Sealed this
Tenth Day of May, 2011

David J. Kappos
*Director of the United States Patent and Trademark Office*

SEQUENCE LISTING

<160> NUMBER OF SEQ ID NOS: 14

<210> SEQ ID NO 1
<211> LENGTH: 1521
<212> TYPE: DNA
<213> ORGANISM: Pedobacter heparinus

<400> SEQUENCE: 1

```
atgaagatgc tgaataaact agccggatac ttattgccga tcatggtgct gctgaatgtg      60
gcaccatgct taggtcaggt tgttgcttca aatgaaactt tataccaggt tgtaaaggag     120
gtaaaacccg gtggtctggt acagattgcc gatgggactt ataaagatgt tcagctgatt     180
gtcagcaatt caggaaaatc tggtttgccc atcactatta aagccctgaa cccgggtaag     240 gttttttta ccggagatgc taaagtagag ctgaggggcg agcacctgat actggaaggc     300
```

```
atctggttta aagacgggaa cagagctatt caggcatgga aatcacatgg acccggattg    360
gtggctatat atggtagcta taaccgcatt accgcatgtg tatttgattg ttttgatgaa    420
gccaattctg cttacattac tacttcgctt accgaagacg gaaaggtacc tcaacattgc    480
cgcatagacc attgcagttt taccgataag atcacttttg accaggtaat taacctgaac    540
aatacagcca gagctattaa agacggttcg gtgggaggac cggggatgta ccatcgtgtt    600
gatcactgtt ttttttccaa tccgcaaaaa ccgggtaatg ccggaggggg aatcaggatt    660
ggctattacc gtaatgatat aggccgttgt ctggtagact ctaacctgtt tatgcgtcag    720
gattcggaag cagagatcat caccagcaaa tcgcaggaaa atgtttatta tggtaatact    780
tacctgaatt gccagggcac catgaacttt cgtcacggtg atcatcaggt ggccattaac    840
aatttttata taggcaatga ccagcgattt ggatacgggg aatgtttgt ttggggaagc    900
aggcatgtca tagcctgtaa ttattttgag ctgtccgaaa ccataaagtc gaggggggaac    960
gccgcattgt atttaaaccc cggtgctatg gcttcggagc atgctcttgc tttcgatatg   1020
ttgatagcca acaacgcttt catcaatgta aatgggtatg ccatccattt taatccattg   1080
gatgagcgca gaaaagaata ttgtgcagcc aataggctta agttcgaaac cccgcaccag   1140
ctaatgttaa aggcaatct tttctttaag gataaacctt atgtttaccc atttttttaaa   1200
gatgattatt ttatagcagg gaaaaatagc tggactggta atgtagcctt aggtgtggaa   1260
aagggaatcc ctgttaacat ttcggccaat aggtctgcct ataagccggt aaaaattaaa   1320
gatatccagc ccatagaagg aatcgctctt gatctcaatg cgctgatcag caaaggcatt   1380
acaggaaagc cccttagctg ggatgaagta aggccctact ggttaaaaga aatgcccggg   1440
acgtatgctt taacggccag gctttctgca gatagggctg caaagtttaa agccgtaatt   1500
aaaagaaata aagagcactg a                                             1521
```

<210> SEQ ID NO 2
<211> LENGTH: 506
<212> TYPE: PRT
<213> ORGANISM: Pedobacter heparinus

<400> SEQUENCE: 2

```
Met Lys Met Leu Asn Lys Leu Ala Gly Tyr Leu Leu Pro Ile Met Val
1               5                   10                  15

Leu Leu Asn Val Ala Pro Cys Leu Gly Gln Val Ala Ser Asn Glu
            20                  25                  30

Thr Leu Tyr Gln Val Val Lys Glu Val Lys Pro Gly Gly Leu Val Gln
        35                  40                  45

Ile Ala Asp Gly Thr Tyr Lys Asp Val Gln Leu Ile Val Ser Asn Ser
    50                  55                  60

Gly Lys Ser Gly Leu Pro Ile Thr Ile Lys Ala Leu Asn Pro Gly Lys
65                  70                  75                  80

Val Phe Phe Thr Gly Asp Ala Lys Val Glu Leu Arg Gly Glu His Leu
                85                  90                  95

Ile Leu Glu Gly Ile Trp Phe Lys Asp Gly Asn Arg Ala Ile Gln Ala
            100                 105                 110

Trp Lys Ser His Gly Pro Gly Leu Val Ala Ile Tyr Gly Ser Tyr Asn
        115                 120                 125

Arg Ile Thr Ala Cys Val Phe Asp Cys Phe Asp Glu Ala Asn Ser Ala
    130                 135                 140

Tyr Ile Thr Thr Ser Leu Thr Glu Asp Gly Lys Val Pro Gln His Cys
```

-continued

```
            145                 150                 155                 160
        Arg Ile Asp His Cys Ser Phe Thr Asp Lys Ile Thr Phe Asp Gln Val
                        165                 170                 175
        Ile Asn Leu Asn Asn Thr Ala Arg Ala Ile Lys Asp Gly Ser Val Gly
                        180                 185                 190
        Gly Pro Gly Met Tyr His Arg Val Asp His Cys Phe Ser Asn Pro
                        195                 200                 205
        Gln Lys Pro Gly Asn Ala Gly Gly Ile Arg Ile Gly Tyr Tyr Arg
                        210                 215                 220
        Asn Asp Ile Gly Arg Cys Leu Val Asp Ser Asn Leu Phe Met Arg Gln
        225                 230                 235                 240
        Asp Ser Glu Ala Glu Ile Ile Thr Ser Lys Ser Gln Glu Asn Val Tyr
                        245                 250                 255
        Tyr Gly Asn Thr Tyr Leu Asn Cys Gln Gly Thr Met Asn Phe Arg His
                        260                 265                 270
        Gly Asp His Gln Val Ala Ile Asn Asn Phe Tyr Ile Gly Asn Asp Gln
                        275                 280                 285
        Arg Phe Gly Tyr Gly Gly Met Phe Val Trp Gly Ser Arg His Val Ile
                        290                 295                 300
        Ala Cys Asn Tyr Phe Glu Leu Ser Glu Thr Ile Lys Ser Arg Gly Asn
        305                 310                 315                 320
        Ala Ala Leu Tyr Leu Asn Pro Gly Ala Met Ala Ser Glu His Ala Leu
                        325                 330                 335
        Ala Phe Asp Met Leu Ile Ala Asn Asn Ala Phe Ile Asn Val Asn Gly
                        340                 345                 350
        Tyr Ala Ile His Phe Asn Pro Leu Asp Glu Arg Arg Lys Glu Tyr Cys
                        355                 360                 365
        Ala Ala Asn Arg Leu Lys Phe Glu Thr Pro His Gln Leu Met Leu Lys
                        370                 375                 380
        Gly Asn Leu Phe Phe Lys Asp Lys Pro Tyr Val Tyr Pro Phe Phe Lys
        385                 390                 395                 400
        Asp Asp Tyr Phe Ile Ala Gly Lys Asn Ser Trp Thr Gly Asn Val Ala
                        405                 410                 415
        Leu Gly Val Glu Lys Gly Ile Pro Val Asn Ile Ser Ala Asn Arg Ser
                        420                 425                 430
        Ala Tyr Lys Pro Val Lys Ile Lys Asp Ile Gln Pro Ile Glu Gly Ile
                        435                 440                 445
        Ala Leu Asp Leu Asn Ala Leu Ile Ser Lys Gly Ile Thr Gly Lys Pro
                        450                 455                 460
        Leu Ser Trp Asp Glu Val Arg Pro Tyr Trp Leu Lys Glu Met Pro Gly
        465                 470                 475                 480
        Thr Tyr Ala Leu Thr Ala Arg Leu Ser Ala Asp Arg Ala Ala Lys Phe
                        485                 490                 495
        Lys Ala Val Ile Lys Arg Asn Lys Glu His
                        500                 505

<210> SEQ ID NO 3
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 3
aactttcgtg ccggtgatca t                                              21
```

```
<210> SEQ ID NO 4
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 4
atgatcaccg gcacgaaagt t                                              21

<210> SEQ ID NO 5
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 5
atggcttcgg cgcatgctct t                                              21

<210> SEQ ID NO 6
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 6
aagagcatgc gccgaagcca t                                              21

<210> SEQ ID NO 7
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 7
atcaccagcg cgtcgcagga a                                              21

<210> SEQ ID NO 8
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 8
ttcctgcgaa gcgctggtga t                                              21

<210> SEQ ID NO 9
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 9
atgaactttg ctcacggtga t                                              21

<210> SEQ ID NO 10
<211> LENGTH: 21
<212> TYPE: DNA
<213> ORGANISM: artificial sequence
<220> FEATURE:
```

```
<223> OTHER INFORMATION: synthetic oligonucleotide

<400> SEQUENCE: 10
atcaccgtga gcaaagttca t                                              21

<210> SEQ ID NO 11
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 11
ttggatgagg ccagaaaaga a                                              21

<210> SEQ ID NO 12
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 12
ttcttttctg gcctcatcca a                                              21

<210> SEQ ID NO 13
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 13
gatgagcgcg caaaagaata t                                              21

<210> SEQ ID NO 14
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 14
atattctttt gcgcgctcat c                                              21
```